United States Patent
Rodgers et al.

(10) Patent No.: US 6,204,262 B1
(45) Date of Patent: Mar. 20, 2001

(54) 1,3-BENZODIAZEPIN-2-ONES AND 1,3-BENZOXAZEPIN-2-ONES USEFUL AS HIV REVERSE TRANSCRIPTASE INHIBITORS

(75) Inventors: James D. Rodgers, Landenberg, PA (US); Anthony J. Cocuzza; Donna M. Bilder, both of Wilmington, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/342,778

(22) Filed: Jun. 29, 1999

Related U.S. Application Data

(60) Provisional application No. 60/091,252, filed on Jun. 30, 1998.

(51) Int. Cl.[7] .................. C07D 243/04; A61K 31/55; A61P 31/18
(52) U.S. Cl. ........................... 514/221; 540/500
(58) Field of Search .............. 540/500; 514/221

(56) References Cited

U.S. PATENT DOCUMENTS

| | | | |
|---|---|---|---|
| 4,764,512 | * 8/1988 | Molino et al. | 514/183 |
| 5,519,021 | 5/1996 | Young et al. | 514/230.5 |
| 5,532,357 | 7/1996 | Rodgers et al. | 540/492 |

FOREIGN PATENT DOCUMENTS

| | | |
|---|---|---|
| 4320347 | 12/1994 | (DE). |
| 0530994 | 3/1993 | (EP). |
| 9512583 | 5/1995 | (WO). |

OTHER PUBLICATIONS

Taylor et al., Journla of Chem. Soc., Perkin Trans. 1 (1976), (12), 1331–8.*
Houpis et al., *Tetr. Lett.* 1994, 35(37), 6811–6814.
Tucker et al., *J. Med. Chem.* 1994, 37, 2437–2444.
Huffman et al., *J. Org. Chem.* 1995, 60, 1590–1594.

* cited by examiner

*Primary Examiner*—Bruck Kifle
(74) *Attorney, Agent, or Firm*—David H. Vance

(57) ABSTRACT

The present invention relates to 1,3-benzodiazepin-2-ones and 1,3-benzoxazepin-2-ones of formula I:

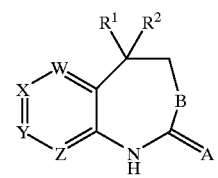

I or stereoisomeric forms, stereoisomeric mixtures, or pharmaceutically acceptable salt forms thereof, which are useful as inhibitors of HIV reverse transcriptase, and to pharmaceutical compositions and diagnostic kits comprising the same, and methods of using the same for treating viral infection or as an assay standard or reagent.

11 Claims, No Drawings ial Application No. 60/091,252, filed Jun. 30, 1998.

1,3-BENZODIAZEPIN-2-ONES AND 1,3-BENZOXAZEPIN-2-ONES USEFUL AS HIV REVERSE TRANSCRIPTASE INHIBITORS

This application claims the benefit of U.S. Provisional Application No. 60/091,252, filed Jun. 30, 1998.

FIELD OF THE INVENTION

This invention relates generally to 1,3-benzodiazepin-2-ones and 1,3-benzoxazepin-2-ones which are useful as inhibitors of HIV reverse transcriptase, pharmaceutical compositions and diagnostic kits comprising the same, methods of using the same for treating viral infection or as assay standards or reagents, and intermediates and processes for making the same.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

Inhibition of the virus at the second critical point, the viral RNA to viral DNA transcription process, has provided a number of the current therapies used in treading AIDS. This transcription must occur for the virion to reproduce because the virion's genes are encoded in RNA and the host cell reads only DNA. By introducing drugs that block the reverse transcriptase from completing the formation of viral DNA, HIV-1 replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in halting HIV replication at the reverse transcriptase (RT) stage.

An active area of research is in the discovery of non-nucleoside HIV reverse transcriptase inhibitors. As an example, it has been found that certain benzoxazinones and quinazolinones are active in the inhibition of HIV reverse transcriptase, the prevention or treatment of infection by HIV and the treatment of AIDS.

U.S. Pat. No. 5,519,021 describe reverse transcriptase inhibitors which are benzoxazinones of the formula:

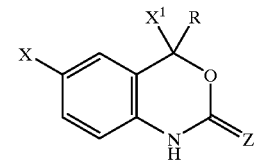

wherein X is a halogen, Z may be O.

EP 0,530,994 and WO 93/04047 describe HIV reverse transcriptase inhibitors which are quinazolinones of the formula A:

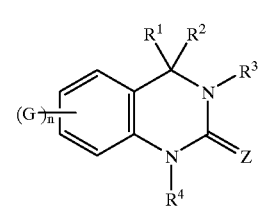

wherein G is a variety of groups, $R^3$ and $R^4$ may be H, Z may be O, $R^2$ may be unsubstituted alkyl, unsubstituted alkenyl, unsubstituted alkynyl, unsubstituted cycloalkyl, unsubstituted heterocycle, and optionally substituted aryl, and $R^1$ may be a variety of groups including substituted alkyl.

WO 95/12583 also describes HIV reverse transcriptase inhibitors of formula A. In this publication, G is a variety of groups, $R^3$ and $R^4$ may be H, Z may be O, $R^2$ is substituted alkenyl or substituted alkynyl, and $R^1$ is cycloalkyl, alkynyl, alkenyl, or cyano. WO 95/13273 illustrates the asymmetric synthesis of one of the compounds of WO 95/12583, (S)-(−)-6-chloro-4-cyclopropyl-3,4-dihydro-4((2-pyridy)ethynyl)-2(1H)-quinazolinone.

Synthetic procedures for making quinazolinones like those described above are detailed in the following references: Houpis et al, *Tetr. Lett.* 1994, 35(37), 6811–6814;

Tucker et al, *J. Med. Chem.* 1994, 37, 2437–2444; and, Huffman et al, *J. Org. Chem.* 1995, 60, 1590–1594.

DE 4,320,347 illustrates quinazolinones of the formula:

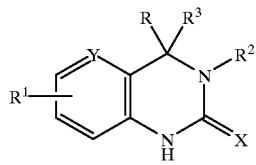

wherein R is a phenyl, carbocyclic ring, or a heterocyclic ring. Compounds of this sort are not considered to be part of the present invention.

Even with the current success of reverse transcriptase inhibitors, it has been found that HIV patients can become resistant to a single inhibitor. Thus, it is desirable to develop additional inhibitors to further combat HIV infection.

SUMMARY OF THE INVENTION

Accordingly, one object of the present invention is to provide novel reverse transcriptase inhibitors.

It is another object of the present invention to provide a novel method of treating HIV infection which comprises administering to a host in need of such treatment a therapeutically effective amount of at least one of the compounds of the present invention or a pharmaceutically acceptable salt form thereof.

It is another object of the present invention to provide a novel method of treating HIV infection which comprises administering to a host in need thereof a therapeutically effective combination of (a) one of the compounds of the present invention and (b) one or more compounds selected form the group consisting of HIV reverse transcriptase inhibitors and HIV protease inhibitors.

It is another object of the present invention to provide pharmaceutical compositions with reverse transcriptase inhibiting activity comprising a pharmaceutically acceptable carrier and a therapeutically effective amount of at least one of the compounds of the present invention or a pharmaceutically acceptable salt form thereof.

It is another object of the present invention to provide a method of inhibiting HIV present in a body fluid sample which comprises treating the body fluid sample with an effective amount of a compound of the present invention.

It is another object of the present invention to provide a kit or container containing at least one of the compounds of the present invention in an amount effective for use as a standard or reagent in a test or assay for determining the ability of a potential pharmaceutical to inhibit HIV reverse transcriptase, HIV growth, or both.

It is another object of the present invention to provide novel compounds for use in therapy.

It is another object of the present invention to provide the use of novel compounds for the manufacture of a medicament for the treatment of HIV.

These and other objects, which will become apparent during the following detailed description, have been achieved by the inventors' discovery that compounds of formula (I):

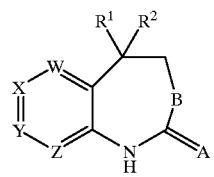

wherein $R^1$, $R^2$, $R^3$, X, and Y are defined below, stereoisomeric forms, mixtures of stereoisomeric forms, or pharmaceutically acceptable salt forms thereof, are effective reverse transcriptase inhibitors.

DETAILED DESCRIPTION OF PREFERRED EMBODIMENTS

[1] Thus, in an embodiment, the present invention provides a novel compound of formula I:

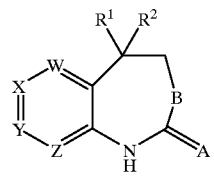

or a stereoisomer or pharmaceutically acceptable salt form thereof, wherein:

A is O or S;

B is selected from O, S, and $NR^8$;

W is N or $CR^3$;

X is N or $CR^{3a}$;

Y is N or $CR^{3b}$;

Z is N or $CR^{3c}$;

provided that if two of W, X, Y, and Z are N, then the remaining are other than N;

$R^1$ is selected from the group $C_{1-3}$ alkyl substituted with 0–7 halogen and cyclopropyl;

$R^2$ is selected from the group —$R^{2c}$, —$OR^{2c}$, —$OCHR^{2a}R^{2b}$, —$OCH_2CHR^{2a}R^{2b}$, —$O(CH_2)_2CHR^{2a}R^{2b}$, —$OCHR^{2a}C=C—R^{2b}$, —$OCHR^{2a}C=R^{2c}$, —$OCHR^{2a}C\equiv C—R^{2b}$, —$SR^{2c}$, —$SCHR^{2a}R^{2b}$, —$SCH_2CHR^{2a}R^{2b}$, —$S(CH_2)_2CHR^{2a}R^{2b}$, —$SCHR^{2a}C=C—R^{2b}$, —$SCHR^{2a}C=R^{2c}$, —$SCHR^{2a}C\equiv C—R^{2b}$, —$NR^{2a}R^{2c}$, —$NHCHR^{2a}R^{2b}$, —$NHCH_2CHR^{2a}R^{2b}$, —$NH(CH_2)_2CHR^{2a}R^{2b}$, —$NHCHR^{2a}C=C—R^{2b}$, —$NHCHR^{2a}C=R^{2c}$, and —$NHCHR^{2a}C\equiv C—R^{2b}$;

$R^{2a}$ is selected from the group H, $CH_3$, $CH_2CH_3$, $CH(CH_3)_2$, and $CH_2CH_2CH_3$;

$R^{2b}$ is H or $R^{2c}$;

$R^{2c}$ is selected from the group $C_{1-6}$ alkyl substituted with 0–2 $R^4$, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, phenyl substituted with 0–2 $R^{3d}$, and 3–6 membered heterocyclic group containing 1–3 heteroatoms selected from the group O, N, and S, substituted with 0–2 $R^{3d}$;

alternatively, the group —$NR^{2a}R^{2c}$ represents a 4–7 membered cyclic amine, wherein 0–1 carbon atoms are replaced by O or $NR^5$;

$R^3$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, and a 5–6 membered heteroaromatic ring containing 1–4 heteroatoms selected from the group O, N, and S;

R$^{3a}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$ and —SO$_2$NR$^5$R$^{5a}$;

alternatively, R$^{3a}$ and R$^{3b}$ together form —OCH$_2$O—;

R$^{3c}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3b}$ and R$^{3c}$ together form —OCH$_2$O—;

R$^{3d}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)NR$^7$, —NHC(O)NR$^5$R$^{5a}$, —NHSO$_2$R$^{10}$, and —SO$_2$NR$^5$R$^{5a}$;

R$^{3e}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3f}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3g}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, C$_{3-10}$ carbocycle substituted with 0–3 R$^{3f}$ and a 5–10 membered heterocyclic group containing 1–3 heteroatoms selected from the group O, N, and S, substituted with 0–3 R$^{3f}$; and, R$^4$ is selected from the group F, Cl, Br, I, C$_{1-6}$ alkyl substituted with 0–2 R$^{3e}$, C$_{3-10}$ carbocycle substituted with 0–2 R$^{3e}$, phenyl substituted with 0–5 R$^{3e}$, and a 5–10 membered heterocyclic group containing 1–3 heteroatoms selected from the group O, N, and S, substituted with 0–2 R$^{3e}$;

R$^5$ and R$^{5a}$ are independently selected from the group H and C$_{1-4}$ alkyl;

alternatively, R$^5$ and R$^{5a}$, together with the nitrogen to which they are attached, combine to form a 5–6 membered ring containing 0–1 O or N atoms;

R$^6$ is selected from the group H, OH, C$_{1-4}$ alkyl, C$_{1-4}$ alkoxy, and NR$^5$R$^{5a}$;

R$^7$ is selected from the group C$_{1-3}$ alkyl and C$_{1-3}$ alkoxy;

R$^8$ is selected from the group H, OR$^9$, SR$^9$, NR$^5$R$^9$, C$_{1-6}$ alkyl substituted with 0–3 R$^{3g}$, C$_{2-6}$ alkenyl substituted with 0–3 R$^{3g}$, C$_{2-6}$ alkynyl substituted with 0–3 R$^{3g}$, C$_{3-5}$ cycloalkyl substituted with 0–2 R$^{3f}$, phenyl substituted with 0–5 R$^{3f}$, and a 5–6 membered heterocyclic group containing 1–3 heteroatoms selected from the group O, N, and S, substituted with 0–2 R$^{3f}$;

R$^9$ is selected from the group C$_{3-10}$ carbocycle substituted with 0–5 R$^{3f}$ and a 5–10 membered heterocyclic group containing 1–3 heteroatoms selected from the group O, N, and S, substituted with 0–2 R$^{3f}$; and, R$^{10}$ is selected from the group C$_{1-4}$ alkyl and phenyl.

[2] In a preferred embodiment, the present invention provides a novel compound of formula I, wherein:

B is NR$^8$;

R$^1$ is selected from the group C$_{1-3}$ alkyl substituted with 1–7 halogen and cyclopropyl;

R$^2$ is selected from the group —R$^{2c}$, —OR$^{2c}$, —OCHR$^{2a}$R$^{2b}$, —OCH$_2$CHR$^{2a}$R$^{2b}$, —O(CH$_2$)$_2$CHR$^{2a}$R$^{2b}$, —OCHR$^{2a}$C=C—R$^{2b}$, —OCHR$^{2a}$C=R$^{2c}$, —OCHR$^{2a}$C≡C—R$^{2b}$, —SR$^{2c}$, —SCHR$^{2a}$R$^{2b}$, —SCH$_2$CHR$^{2a}$R$^{2b}$, —S(CH$_2$)$_2$CHR$^{2a}$R$^{2b}$, —SCHR$^{2a}$C=C—R$^{2b}$, —SCHR$^{2a}$C=R$^{2c}$, and —SCHR$^{2a}$C≡C—R$^{2b}$;

R$^{2a}$ is selected from the group H, CH$_3$, CH$_2$CH$_3$, CH(CH$_3$)$_2$, and CH$_2$CH$_2$CH$_3$;

R$^{2b}$ is H or R$^{2c}$;

R$^{2c}$ is selected from the group C$_{1-5}$ alkyl substituted with 0–2 R$^4$, C$_{2-5}$ alkenyl substituted with 0–2 R$^4$, C$_{2-5}$ alkynyl substituted with 0–1 R$^4$, C$_{3-6}$ cycloalkyl substituted with 0–2 R$^{3d}$, and phenyl substituted with 0–2 R$^{3d}$;

R$^3$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

R$^{3a}$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, and NHC(O)NR$^5$R$^{5a}$;

alternatively, R$^{3a}$ and R$^{3b}$ together form —OCH$_2$O—;

R$^4$ is selected from the group Cl, F, C$_{1-4}$ alkyl substituted with 0–2 R$^{3e}$, C$_{3-5}$ carbocycle substituted with 0–2 R$^{3e}$, phenyl substituted with 0–5 R$^{3e}$, and a 5–6 membered heterocyclic group containing 1–3 heteroatoms selected from the group O, N, and S, substituted with 0–2 R$^{3e}$;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$;

R$^7$ is selected from the group CH$_3$, C$_2$H$_5$, CH(CH$_3$)$_2$, OCH$_3$, OC$_2$H$_5$, and OCH(CH$_3$)$_2$; and, R$^8$ is selected from the group H, cyclopropyl, CH$_3$, C$_2$H$_5$, and CH(CH$_3$)$_2$.

[3] In a more preferred embodiment, the present invention provides a novel compound of formula I, wherein:

R$^1$ is selected from the group CF$_3$, C$_2$F$_5$, and cyclopropyl;

R$^2$ is selected from the group —R$^{2c}$, —OR$^{2c}$, —OCHR$^{2a}$R$^{2b}$, —OCH$_2$CHR$^{2a}$R$^{2b}$, —OCHR$^{2a}$C=C—R$^{2b}$, —OCHR$^{2a}$C=R$^{2c}$, —OCHR$^{2a}$C≡C—R$^{2b}$, —SR$^{2c}$, —SCHR$^{2a}$R$^{2b}$, —SCH$_2$CHR$^{2a}$R$^{2b}$, —SCHR$^{2a}$C=C—R$^{2b}$, —SCHR$^{2a}$C=R$^{2c}$, and —SCHR$^{2a}$C≡C—R$^{2b}$;

R$^{2a}$ is selected from the group H, CH$_3$, CH$_2$CH$_3$, CH(CH$_3$)$_2$, and CH$_2$CH$_2$CH$_3$;

R$^{2b}$ is H or R$^{2c}$;

R$^{2c}$ is selected from the group C$_{1-3}$ alkyl substituted with 0–2 R$^4$, C$_{2-3}$ alkenyl substituted with 0–2 R$^4$, C$_{2-3}$ alkynyl substituted with 0–1 R$^4$, and C$_{3-6}$ cycloalkyl substituted with 0–2 R$^{3d}$;

R$^3$, at each occurrence, is independently selected from the group H, C$_{1-3}$ alkyl, OH, C$_{1-3}$ alkoxy, F, Cl, Br, I, NR$^5$R$^{5a}$, NO$_2$, —CN, C(O)R$^6$, NHC(O)R$^7$, and NHC(O)NR$^5$R$^{5a}$;

alternatively, R$^3$ and R$^{3a}$ together form —OCH$_2$O—;

R$^{3b}$ is H;

R$^{3c}$ is H;

R$^{3e}$, at each occurrence, is independently selected from the group H, C$_{1-4}$ alkyl, —OH, C$_{1-4}$ alkoxy, OCF$_3$, F, Cl, —NR$^5$R$^{5a}$, —C(O)R$^6$, and —SO$_2$NR$^5$R$^{5a}$;

R$^4$ is selected from the group Cl, F, C$_{1-4}$ alkyl substituted with 0–1 R$^{3e}$, C$_{3-5}$ carbocycle substituted with 0–2 R$^{3e}$, phenyl substituted with 0–2 R$^{3e}$, and a 5–6 membered heterocyclic group containing 1–3 heteroatoms selected from the group O, N, and S, substituted with 0–1 R$^{3e}$;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$;

R$^7$ is selected from the group CH$_3$, C$_2$H$_5$, OCH$_3$, and OC$_2$H$_5$; and, R$^8$ is selected from the group H, cyclopropyl, CH$_3$, and C$_2$H$_5$.

[4] In an even more preferred embodiment, the present invention provides a novel compound of formula I, wherein:

R$^1$ is CF$_3$;

R$^2$ is selected from the group —R$^{2c}$, —OR$^{2c}$, —OCH$_2$R$^{2b}$, —OCH$_2$CH$_2$R$^{2b}$, —OCH$_2$C=C—R$^{2b}$, —OCH$_2$C≡C—R$^{2b}$, —SR$^{2c}$, —SCH$_2$R$^{2b}$, —SCH$_2$CH$_2$R$^{2b}$, —SCH$_2$C=C—R$^{2b}$, and —SCH$_2$C≡C—R$^{2b}$;

R$^{2b}$ is H or R$^{2c}$;

R$^{2c}$ is selected from the group methyl substituted with 0–2 R$^4$, ethyl substituted with 0–2 R$^4$, propyl substituted with 0–2 R$^4$, ethenyl substituted with 0–2 R$^4$, 1-propenyl substituted with 0–2 R$^4$, 2-propenyl substituted with 0–2 R$^4$, ethynyl substituted with 0–2 R$^4$, 1-propynyl substituted with 0–2 R$^4$, 2-propynyl substituted with 0–2 R$^4$, and cyclopropyl substituted with 0–1 R$^{3d}$;

R$^3$, at each occurrence, is independently selected from the group C$_{1-3}$ alkyl, OH, C$_{1-3}$ alkoxy, F, Cl, NR$^5$R$^{5a}$, NO$_2$, —CN, and C(O)R$^6$;

alternatively, R$^3$ and R$^{3a}$ together form —OCH$_2$O—;

R$^{3d}$, at each occurrence, is independently selected from the group CH$_3$, —OH, OCH$_3$, OCF$_3$, F, Cl, and —NR$^5$R$^{5a}$;

R$^{3e}$, at each occurrence, is independently selected from the group CH$_3$, —OH, OCH$_3$, OCF$_3$, F, Cl, and NR$^5$R$^{5a}$;

R$^4$ is selected from the group Cl, F, CH$_3$, CH$_2$CH$_3$, cyclopropyl substituted with 0–1 R$^{3e}$, 1-methylcyclopropyl substituted with 0–1 R$^{3e}$, cyclobutyl substituted with 0–1 R$^{3e}$, phenyl substituted with 0–2 R$^{3e}$, and a 5–6 membered heterocyclic group containing 1–3 heteroatoms selected from the group O, N, and S, substituted with 0–1 R$^{3e}$, wherein the heterocyclic group is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$;

R$^7$ is selected from the group CH$_3$, C$_2$H$_5$, OCH$_3$, and OC$_2$H$_5$; and, R$^8$ is selected from the group H, cyclopropyl, and C$_2$H$_5$.

[5] In a further preferred embodiment, wherein the compound is of formula Ia:

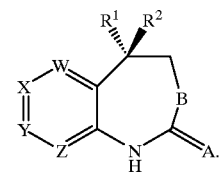

Ia

[6] In a further preferred embodiment, wherein the compound is of formula Ib:

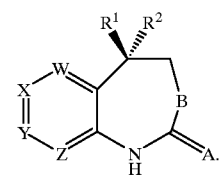

Ib

[7] In a further preferred embodiment, the compound of formula I is selected from the group:

7-Chloro-5-(2-cyclopropylethynyl)-1,5-dihydro-5-(trifluoromethyl)-1,3-benzodiazepin-2-one;

6,7-difluoro-5-(2-cyclopropylethynyl)-1,5-dihydro-5-(trifluoromethyl)-1,3-benzodiazepin-2-one;

7-Chloro-5-(2-cyclopropylethenyl)-1,5-dihydro-5-(trifluoromethyl)-1,3-benzodiazepin-2-one;

7-Chloro-5-(2-cyclopropylethynyl)-1,5-dihydro-5-(trifluoromethyl)-1,3-benzodiazepin-2-thione;

7-Chloro-5-(2-n-butyl)-1,5-dihydro-5-(trifluoromethyl)-1,3-benzodiazepin-2-one;

7-Chloro-5-(2-cyclopropylethynyl)-1,5-dihydro-3-methyl-5-(trifluoromethyl)-1,3-benzodiazepin-2-one;

7-Chloro-5-(2-cyclopropylethynyl)-1,5-dihydro-3-ethyl-5-(trifluoromethyl)-1,3-benzodiazepin-2-one;

7-Chloro-5-(2-cyclopropylethynyl)-1,5-dihydro-3-cyclopropyl-5-(trifluoromethyl)-1,3-benzodiazepin-2-one;

7-Chloro-5-cyclopropylmethyloxy-1,5-dihydro-3-methyl-5-(trifluoromethyl)-1,3-benzodiazepin-2-one;

7-Chloro-5-(3-methyl-2-butenyloxy)-1,5-dihydro-3-methyl-5-(trifluoromethyl)-1,3-benzodiazepin-2-one;

7-Chloro-5-(3-allyloxy)-1,5-dihydro-3-methyl-5-(trifluoromethyl)-1,3-benzodiazepin-2-one;

7-Chloro-5-(3,3-dichloro-2-propenyloxy)-1,5-dihydro-3-methyl-5-(trifluoromethyl)-1,3-benzodiazepin-2-one;

7-Chloro-5-(2-propynyloxy)-1,5-dihydro-3-methyl-5-(trifluoromethyl)-1,3-benzodiazepin-2-one;

7-Chloro-5-(2-fluoro-6-methoxybenzyloxy)-1,5-dihydro-3-methyl-5-(trifluoromethyl)-1,3-benzodiazepin-2-one;

7-Chloro-5-(cyclopropylmethyloxy)-1,5-dihydro-5-(trifluoromethyl)-1,3-benzodiazepin-2-one;

(S)-7-Chloro-5-(cyclopropylmethyloxy)-1,5-dihydro-5-(trifluoromethyl)-1,3-benzodiazepin-2-one;

7-Chloro-3-cyclopropyl-5-(cyclopropylmethoxy)-1,5-dihydro-5-(trifluoromethyl)-1,3-benzodiazepin-2-one;

(S)-7-Chloro-3-cyclopropyl-5-(cyclopropylmethoxy)-1,5-dihydro-5-(trifluoromethyl)-1,3-benzodiazepin-2-one;

7-Chloro-3-cyclopropyl-5-propyloxy-1,5-dihydro-5-(trifluoromethyl)-1,3-benzodiazepin-2-one;

7-Chloro-3-cyclopropyl-5-propylthio-1,5-dihydro-5-(trifluoromethyl)-1,3-benzodiazepin-2-one;

7-Chloro-3-cyclopropyl-5-allylthio-1,5-dihydro-5-(trifluoromethyl)-1,3-benzodiazepin-2-one;

7-Chloro-3-cyclopropyl-5-allyloxy-1,5-dihydro-5-(trifluoromethyl)-1,3-benzodiazepin-2-one;

7-Chloro-3-cyclopropyl-5-(3-methyl-2-butenyloxy)-1,5-dihydro-5-(trifluoromethyl)-1,3-benzodiazepin-2-one;

7-Chloro-3-cyclopropyl-5-cyclobutylmethyloxy-1,5-dihydro-5-(trifluoromethyl)-1,3-benzodiazepin-2-one;

7-Chloro-3-cyclopropyl-5-(1-methylcyclopropyl)methyloxy-1,5-dihydro-5-(trifluoromethyl)-1,3-benzodiazepin-2-one;

7-Chloro-3-cyclopropyl-5-(2-pyridyl)methyloxy-1,5-dihydro-5-(trifluoromethyl)-1,3-benzodiazepin-2-one;

7-Chloro-3-isopropyl-5-cyclopropylmethyloxy-1,5-dihydro-5-(trifluoromethyl)-1,3-benzodiazepin-2-one;

7-Chloro-3-cyclobutyl-5-cyclopropylmethyloxy-1,5-dihydro-5-(trifluoromethyl)-1,3-benzodiazepin-2-one;

7-Chloro-5-(cyclopropylmethoxy)-1,5-dihydro-3-ethyl-5-(trifluoromethyl)-1,3-benzodiazepin-2-one;

(S)-7-Chloro-5-(cyclopropylmethyloxy)-1,5-dihydro-3-ethyl-5-(trifluoromethyl)-1,3-benzodiazepin-2-one;

7-Chloro-3-ethyl-5-(3-methyl-2-butenyloxy)-1,5-dihydro-5-(trifluoromethyl)-1,3-benzodiazepin-2-one;

7-Chloro-3-ethyl-5-allylthio-1,5-dihydro-5-(trifluoromethyl)-1,3-benzodiazepin-2-one;

7-Chloro-3-ethyl-5-cyclobutylmethyloxy-1,5-dihydro-5-(trifluoromethyl)-1,3-benzodiazepin-2-one;

7-Chloro-3-ethyl-5-cyclopropylmethylthio-1,5-dihydro-5-(trifluoromethyl)-1,3-benzodiazepin-2-one;

7-Chloro-3-ethyl-5-(1-methylcyclopropyl)methyloxy-1,5-dihydro-5-(trifluoromethyl)-1,3-benzodiazepin-2-one;

7-Chloro-3-propyl-5-cyclopropylmethyloxy-1,5-dihydro-5-(trifluoromethyl)-1,3-benzodiazepin-2-one;

7-Fluoro-5-(cyclopropylmethoxy)-1,5-dihydro-5-(trifluoromethyl)-1,3-benzodiazepin-2-one;

7-Fluoro-3-ethyl-5-cyclopropylmethyloxy-1,5-dihydro-5-(trifluoromethyl)-1,3-benzodiazepin-2-one;

7-Fluoro-5-(cyclobutylmethoxy)-1,5-dihydro-5-(trifluoromethyl)-1,3-benzodiazepin-2-one;

7-Fluoro-3-ethyl-5-cyclobutylmethyloxy-1,5-dihydro-5-(trifluoromethyl)-1,3-benzodiazepin-2-one;

7-Chloro-5-[2-(1-methylcyclopropyl)ethynyl]-1,5-dihydro-5-(trifluoromethyl)-1,3-benzodiazepin-2-one;

7-Chloro-5-cyclobutylmethyloxy-1,5-dihydro-5-(trifluoromethyl)-1,3-benzodiazepin-2-one;

7-Chloro-5-(3-methyl-2-butenyloxy)-1,5-dihydro-5-(trifluoromethyl)-1,3-benzodiazepin-2-one;

7-Chloro-5-(phenylmethyloxy)-1,5-dihydro-5-(trifluoromethyl)-1,3-benzodiazepin-2-one;

7-Chloro-5-[(2-pyridyl)methyloxy]-1,5-dihydro-5-(trifluoromethyl)-1,3-benzodiazepin-2-one;

7-Chloro-5-[(1-methylcyclopropyl)methyoxy]-1,5-dihydro-5-(trifluoromethyl)-1,3-benzodiazepin-2-one;

7-Chloro-5-(3-methylphenyloxy)-1,5-dihydro-5-(trifluoromethyl)-1,3-benzodiazepin-2-one;

7-Chloro-5-(cyclopropylmethylthio)-1,5-dihydro-5-(trifluoromethyl)-1,3-benzodiazepin-2-one;

7-Chloro-5-(propylthio)-1,5-dihydro-5-(trifluoromethyl)-1,3-benzodiazepin-2-one; and, 7-Chloro-5-(2-propenylthio)-1,5-dihydro-5-(trifluoromethyl)-1,3-benzodiazepin-2-one;

or a pharmaceutically acceptable salt form thereof.

[8] In another further preferred embodiment, the compound of formula I is selected from the group:

(S)-7-Chloro-5-(2-cyclopropylethynyl)-1,5-dihydro-5-(trifluoromethyl)-1,3-benzodiazepin-2-one;

(S)-6,7-difluoro-5-(2-cyclopropylethynyl)-1,5-dihydro-5-(trifluoromethyl)-1,3-benzodiazepin-2-one;

(S)-7-Chloro-5-(2-cyclopropylethenyl)-1,5-dihydro-5-(trifluoromethyl)-1,3 -benzodiazepin-2-one;

(S)-7-Chloro-5-(2-cyclopropylethynyl)-1,5-dihydro-5-(trifluoromethyl)-1,3-benzodiazepin-2-thione;

(S)-7-Chloro-5-(2-n-butyl)-1,5-dihydro-5-(trifluoromethyl)-1,3-benzodiazepin-2-one;

(S)-7-Chloro-5-(2-cyclopropylethynyl)-1,5-dihydro-3-methyl-5-(trifluoromethyl)-1,3-benzodiazepin-2-one;

(S)-7-Chloro-5-(2-cyclopropylethynyl)-1,5-dihydro-3-ethyl-5-(trifluoromethyl)-1,3-benzodiazepin-2-one;

(S)-7-Chloro-5-(2-cyclopropylethynyl)-1,5-dihydro-3-cyclopropyl-5-(trifluoromethyl)-1,3-benzodiazepin-2-one;

(S)-7-Chloro-5-cyclopropylmethyloxy-1,5-dihydro-3-methyl-5-(trifluoromethyl)-1,3-benzodiazepin-2-one;

(S)-7-Chloro-5-(3-methyl-2-butenyloxy)-1,5-dihydro-3-methyl-5-(trifluoromethyl)-1,3-benzodiazepin-2-one;

(S)-7-Chloro-5-(3-allyloxy)-1,5-dihydro-3-methyl-5-(trifluoromethyl)-1,3-benzodiazepin-2-one;

(S)-7-Chloro-5-(3,3-dichloro-2-propenyloxy)-1,5-dihydro-3-methyl-5-(trifluoromethyl)-1,3-benzodiazepin-2-one;

(S)-7-Chloro-5-(2-propynyloxy)-1,5-dihydro-3-methyl-5-(trifluoromethyl)-1,3-benzodiazepin-2-one;

(S)-7-Chloro-5-(2-fluoro-6-methoxybenzyloxy)-1,5-dihydro-3-methyl-5-(trifluoromethyl)-1,3-benzodiazepin-2-one;

(S)-7-Chloro-5-(cyclopropylmethyloxy)-1,5-dihydro-5-(trifluoromethyl)-1,3-benzodiazepin-2-one;

(S)-7-Chloro-5-(cyclopropylmethyloxy)-1,5-dihydro-5-(trifluoromethyl)-1,3-benzodiazepin-2-one;

(S)-7-Chloro-3-cyclopropyl-5-(cyclopropylmethoxy)-1,5-dihydro-5-(trifluoromethyl)-1,3-benzodiazepin-2-one;

(S)-7-Chloro-3-cyclopropyl-5-(cyclopropylmethoxy)-1,5-dihydro-5-(trifluoromethyl)-1,3-benzodiazepin-2-one;

(S)-7-Chloro-3-cyclopropyl-5-propyloxy-1,5-dihydro-5-(trifluoromethyl)-1,3-benzodiazepin-2-one;

(S)-7-Chloro-3-cyclopropyl-5-propylthio-1,5-dihydro-5-(trifluoromethyl)-1,3-benzodiazepin-2-one;

(S)-7-Chloro-3-cyclopropyl-5-allylthio-1,5-dihydro-5-(trifluoromethyl)-1,3-benzodiazepin-2-one;

(S)-7-Chloro-3-cyclopropyl-5-allyloxy-1,5-dihydro-5-(trifluoromethyl)-1,3-benzodiazepin-2-one;

(S)-7-Chloro-3-cyclopropyl-5-(3-methyl-2-butenyloxy)-1,5-dihydro-5-(trifluoromethyl)-1,3-benzodiazepin-2-one;

(S)-7-Chloro-3-cyclopropyl-5-cyclobutylmethyloxy-1,5-dihydro-5-(trifluoromethyl)-1,3-benzodiazepin-2-one;

(S)-7-Chloro-3-cyclopropyl-5-(1-methylcyclopropyl)methyloxy-1,5-dihydro-5-(trifluoromethyl)-1,3-benzodiazepin-2-one;

(S)-7-Chloro-3-cyclopropyl-5-(2-pyridyl)methyloxy-1,5-dihydro-5-(trifluoromethyl)-1,3-benzodiazepin-2-one;

(S)-7-Chloro-3-isopropyl-5-cyclopropylmethyloxy-1,5-dihydro-5-(trifluoromethyl)-1,3-benzodiazepin-2-one;

(S)-7-Chloro-3-cyclobutyl-5-cyclopropylmethyloxy-1,5-dihydro-5-(trifluoromethyl)-1,3-benzodiazepin-2-one;
(S)-7-Chloro-5-(cyclopropylmethoxy)-1,5-dihydro-3-ethyl-5-(trifluoromethyl)-1,3-benzodiazepin-2-one;
(S)-7-Chloro-5-(cyclopropylmethyloxy)-1,5-dihydro-3-ethyl-5-(trifluoromethyl)-1,3-benzodiazepin-2-one;
(S)-7-Chloro-3-ethyl-5-(3-methyl-2-butenyloxy)-1,5-dihydro-5-(trifluoromethyl)-1,3-benzodiazepin-2-one;
(S)-7-Chloro-3-ethyl-5-allylthio-1,5-dihydro-5-(trifluoromethyl)-1,3-benzodiazepin-2-one;
(S)-7-Chloro-3-ethyl-5-cyclobutylmethyloxy-1,5-dihydro-5-(trifluoromethyl)-1,3-benzodiazepin-2-one;
(S)-7-Chloro-3-ethyl-5-cyclopropylmethylthio-1,5-dihydro-5-(trifluoromethyl)-1,3-benzodiazepin-2-one;
(S)-7-Chloro-3-ethyl-5-(1-methylcyclopropyl)methyloxy-1,5-dihydro-5-(trifluoromethyl)-1,3-benzodiazepin-2-one;
(S)-7-Chloro-3-propyl-5-cyclopropylmethyloxy-1,5-dihydro-5-(trifluoromethyl)-1,3-benzodiazepin-2-one;
(S)-7-Fluoro-5-(cyclopropylmethoxy)-1,5-dihydro-5-(trifluoromethyl)-1,3-benzodiazepin-2-one;
(S)-7-Fluoro-3-ethyl-5-cyclopropylmethyloxy-1,5-dihydro-5-(trifluoromethyl)-1,3-benzodiazepin-2-one;
(S)-7-Fluoro-5-(cyclobutylmethoxy)-1,5-dihydro-5-(trifluoromethyl)-1,3-benzodiazepin-2-one;
(S)-7-Fluoro-3-ethyl-5-cyclobutylmethyloxy-1,5-dihydro-5-(trifluoromethyl)-1,3-benzodiazepin-2-one;
(S)-7-Chloro-5-[2-(1-methylcyclopropyl)ethynyl]-1,5-dihydro-5-(trifluoromethyl)-1,3-benzodiazepin-2-one;
(S)-7-Chloro-5-cyclobutylmethyloxy-1,5-dihydro-5-(trifluoromethyl)-1,3-benzodiazepin-2-one;
(S)-7-Chloro-5-(3-methyl-2-butenyloxy)-1,5-dihydro-5-(trifluoromethyl)-1,3-benzodiazepin-2-one;
(S)-7-Chloro-5-(phenylmethyloxy)-1,5-dihydro-5-(trifluoromethyl)-1,3-benzodiazepin-2-one;
(S)-7-Chloro-5-[(2-pyridyl)methyloxy]-1,5-dihydro-5-(trifluoromethyl)-1,3-benzodiazepin-2-one;
(S)-7-Chloro-5-[(1-methylcyclopropyl)methyoxy]-1,5-dihydro-5-(trifluoromethyl)-1,3-benzodiazepin-2-one;
(S)-7-Chloro-5-(3-methylphenyloxy)-1,5-dihydro-5-(trifluoromethyl)-1,3-benzodiazepin-2-one;
(S)-7-Chloro-5-(cyclopropylmethylthio)-1,5-dihydro-5-(trifluoromethyl)-1,3-benzodiazepin-2-one;
(S)-7-Chloro-5-(propylthio)-1,5-dihydro-5-(trifluoromethyl)-1,3-benzodiazepin-2-one; and,
(S)-7-Chloro-5-(2-propenylthio)-1,5-dihydro-5-(trifluoromethyl)-1,3-benzodiazepin-2-one;
or a pharmaceutically acceptable salt form thereof.

[9] In another further preferred embodiment, the compound of formula I is selected from the group:
(R)-7-Chloro-5-(2-cyclopropylethynyl)-1,5-dihydro-5-(trifluoromethyl)-1,3-benzodiazepin-2-one;
(R)-6,7-difluoro-5-(2-cyclopropylethynyl)-1,5-dihydro-5-(trifluoromethyl)-1,3-benzodiazepin-2-one;
(R)-7-Chloro-5-(2-cyclopropylethenyl)-1,5-dihydro-5-(trifluoromethyl)-1,3-benzodiazepin-2-one;
(R)-7-Chloro-5-(2-cyclopropylethynyl)-1,5-dihydro-5-(trifluoromethyl)-1,3-benzodiazepin-2-thione;
(R)-7-Chloro-5-(2-n-butyl)-1,5-dihydro-5-(trifluoromethyl)-1,3-benzodiazepin-2-one;
(R)-7-Chloro-5-(2-cyclopropylethynyl)-1,5-dihydro-3-methyl-5-(trifluoromethyl)-1,3-benzodiazepin-2-one;
(R)-7-Chloro-5-(2-cyclopropylethynyl)-1,5-dihydro-3-ethyl-5-(trifluoromethyl)-1,3-benzodiazepin-2-one;
(R)-7-Chloro-5-(2-cyclopropylethynyl)-1,S-dihydro-3-cyclopropyl-5-(trifluoromethyl)-1,3-benzodiazepin-2-one;
(R)-7-Chloro-5-cyclopropylmethyloxy-1,5-dihydro-3-methyl-5-(trifluoromethyl)-1,3-benzodiazepin-2-one;
(R)-7-Chloro-5-(3-methyl-2-butenyloxy)-1,5-dihydro-3-methyl-5-(trifluoromethyl)-1,3-benzodiazepin-2-one;
(R)-7-Chloro-5-(3-allyloxy)-1,5-dihydro-3-methyl-5-(trifluoromethyl)-1,3-benzodiazepin-2-one;
(R)-7-Chloro-5-(3,3-dichloro-2-propenyloxy)-1,5-dihydro-3-methyl-5-(trifluoromethyl)-1,3-benzodiazepin-2-one;
(R)-7-Chloro-5-(2-propynyloxy)-1,5-dihydro-3-methyl-5-(trifluoromethyl)-1,3-benzodiazepin-2-one;
(R)-7-Chloro-5-(2-fluoro-6-methoxybenzyloxy)-1,5-dihydro-3-methyl-5-(trifluoromethyl)-1,3-benzodiazepin-2-one;
(R)-7-Chloro-5-(cyclopropylmethyloxy)-1,5-dihydro-5-(trifluoromethyl)-1,3-benzodiazepin-2-one;
(R)-7-Chloro-5-(cyclopropylmethyloxy)-1,5-dihydro-5-(trifluoromethyl)-1,3-benzodiazepin-2-one;
(R)-7-Chloro-3-cyclopropyl-5-(cyclopropylmethoxy)-1,5-dihydro-5-(trifluoromethyl)-1,3-benzodiazepin-2-one;
(R)-7-Chloro-3-cyclopropyl-5-(cyclopropylmethoxy)-1,5-dihydro-5-(trifluoromethyl)-1,3-benzodiazepin-2-one;
(R)-7-Chloro-3-cyclopropyl-5-propyloxy-1,5-dihydro-5-(trifluoromethyl)-1,3-benzodiazepin-2-one;
(R)-7-Chloro-3-cyclopropyl-5-propylthio-1,5-dihydro-5-(trifluoromethyl)-1,3-benzodiazepin-2-one;
(R)-7-Chloro-3-cyclopropyl-5-allylthio-1,5-dihydro-5-(trifluoromethyl)-1,3-benzodiazepin-2-one;
(R)-7-Chloro-3-cyclopropyl-5-allyloxy-1,5-dihydro-5-(trifluoromethyl)-1,3-benzodiazepin-2-one;
(R)-7-Chloro-3-cyclopropyl-5-(3-methyl-2-butenyloxy)-1,5-dihydro-5-(trifluoromethyl)-1,3-benzodiazepin-2-one;
(R)-7-Chloro-3-cyclopropyl-5-cyclobutylmethyloxy-1,5-dihydro-5-(trifluoromethyl)-1,3-benzodiazepin-2-one;
(R)-7-Chloro-3-cyclopropyl-5-(1-methylcyclopropyl)methyloxy-1,5-dihydro-5-(trifluoromethyl)-1,3-benzodiazepin-2-one;
(R)-7-Chloro-3-cyclopropyl-5-(2-pyridyl)methyloxy-1,5-dihydro-5-(trifluoromethyl)-1,3-benzodiazepin-2-one;
(R)-7-Chloro-3-isopropyl-5-cyclopropylmethyloxy-1,5-dihydro-5-(trifluoromethyl)-1,3-benzodiazepin-2-one;
(R)-7-Chloro-3-cyclobutyl-5-cyclopropylmethyloxy-1,5-dihydro-5-(trifluoromethyl)-1,3-benzodiazepin-2-one;
(R)-7-Chloro-5-(cyclopropylmethoxy)-1,5-dihydro-3-ethyl-5-(trifluoromethyl)-1,3-benzodiazepin-2-one;
(R)-7-Chloro-5-(cyclopropylmethyloxy)-1,5-dihydro-3-ethyl-5-(trifluoromethyl)-1,3-benzodiazepin-2-one;
(R)-7-Chloro-3-ethyl-5-(3-methyl-2-butenyloxy)-1,5-dihydro-5-(trifluoromethyl)-1,3-benzodiazepin-2-one;
(R)-7-Chloro-3-ethyl-5-allylthio-1,5-dihydro-5-(trifluoromethyl)-1,3-benzodiazepin-2-one;
(R)-7-Chloro-3-ethyl-5-cyclobutylmethyloxy-1,5-dihydro-5-(trifluoromethyl)-1,3-benzodiazepin-2-one;
(R)-7-Chloro-3-ethyl-5-cyclopropylmethylthio-1,5-dihydro-5-(trifluoromethyl)-1,3-benzodiazepin-2-one;
(R)-7-Chloro-3-ethyl-5-(1-methylcyclopropyl)methyloxy-1,5-dihydro-5-(trifluoromethyl)-1,3-benzodiazepin-2-one;
(R)-7-Chloro-3-propyl-5-cyclopropylmethyloxy-1,5-dihydro-5-(trifluoromethyl)-1,3-benzodiazepin-2-one;
(R)-7-Fluoro-5-(cyclopropylmethoxy)-1,5-dihydro-5-(trifluoromethyl)-1,3-benzodiazepin-2-one;
(R)-7-Fluoro-3-ethyl-5-cyclopropylmethyloxy-1,5-dihydro-5-(trifluoromethyl)-1,3-benzodiazepin-2-one;
(R)-7-Fluoro-5-(cyclobutylmethoxy)-1,5-dihydro-5-(trifluoromethyl)-1,3-benzodiazepin-2-one;
(R)-7-Fluoro-3-ethyl-5-cyclobutylmethyloxy-1,5-dihydro-5-(trifluoromethyl)-1,3-benzodiazepin-2-one;
(R)-7-Chloro-5-[2-(1-methylcyclopropyl)ethynyl]-1,5-dihydro-5-(trifluoromethyl)-1,3-benzodiazepin-2-one;

(R)-7-Chloro-5-cyclobutylmethyloxy-1,5-dihydro-5-(trifluoromethyl)-1,3-benzodiazepin-2-one;
(R)-7-Chloro-5-(3-methyl-2-butenyloxy)-1,5-dihydro-5-(trifluoromethyl)-1,3-benzodiazepin-2-one;
(R)-7-Chloro-5-(phenylmethyloxy)-1,5-dihydro-5-(trifluoromethyl)-1,3-benzodiazepin-2-one;
(R)-7-Chloro-5-[(2-pyridyl)methyloxy]-1,5-dihydro-5-(trifluoromethyl)-1,3-benzodiazepin-2-one;
(R)-7-Chloro-5-[(1-methylcyclopropyl)methyoxy]-1,5-dihydro-5-(trifluoromethyl)-1,3-benzodiazepin-2-one;
(R)-7-Chloro-5-(3-methylphenyloxy)-1,5-dihydro-5-(trifluoromethyl)-1,3-benzodiazepin-2-one;
(R)-7-Chloro-5-(cyclopropylmethylthio)-1,5-dihydro-5-(trifluoromethyl)-1,3-benzodiazepin-2-one;
(R)-7-Chloro-5-(propylthio)-1,5-dihydro-5-(trifluoromethyl)-1,3-benzodiazepin-2-one; and,
(R)-7-Chloro-5-(2-propenylthio)-1,5-dihydro-5-(trifluoromethyl)-1,3-benzodiazepin-2-one;
or a pharmaceutically acceptable salt form thereof.

In another embodiment, the present invention provides a novel pharmaceutical composition comprising a pharmaceutically acceptable carrier and a therapeutically effective amount of a compound of formula I or pharmaceutically acceptable salt form thereof.

In another embodiment, the present invention provides a novel method of treating HIV infection which comprises administering to a host in need of such treatment a therapeutically effective amount of a compound of formula I or pharmaceutically acceptable salt form thereof.

In another embodiment, the present invention provides a novel method of treating HIV infection which comprises administering, in combination, to a host in need thereof a therapeutically effective amount of:
(a) a compound of formula I; and,
(b) at least one compound selected from the group consisting of HIV reverse transcriptase inhibitors and HIV protease inhibitors.

In another preferred embodiment, the reverse transcriptase inhibitor is selected from the group AZT, ddC, ddI, d4T, 3TC, DPC082, DPC083, DPC961, DPC963, AG1549 delavirdine, efavirenz, nevirapine, Ro 18,893, trovirdine, MKC-442, HBY 097, ACT, UC-781, UC-782, RD4-2025, and MEN 10979, and the protease inhibitor is selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, and ABT-378.

In an even more preferred embodiment, the reverse transcriptase inhibitor is selected from the group AZT, efavirenz, and 3TC and the protease inhibitor is selected from the group saquinavir, ritonavir, nelfinavir, and indinavir.

In a still further preferred embodiment, the reverse transcriptase inhibitor is AZT.

In another still further preferred embodiment, the protease inhibitor is indinavir.

In another embodiment, the present invention provides a pharmaceutical kit useful for the treatment of HIV infection, which comprises a therapeutically effective amount of:
(a) a compound of formula I or a pharmaceutically acceptable salt form thereof; and,
(b) at least one compound selected from the group consisting of HIV reverse transcriptase inhibitors and HIV protease inhibitors, in one or more sterile containers.

In another embodiment, the present invention provides novel compounds of formula I or pharmaceutically acceptable salt forms thereof for use in therapy.

In another embodiment, the present invention provides the use of novel compounds of formula I or pharmaceutically acceptable salt forms thereof for the manufacture of a medicament for the treatment of HIV.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-6}$ alkyl (or alkylene), is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl"

is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-10}$ cycloalkyl, is intended to include $C_3$, $C_4$, $C_5$, $C_6$, $C_7$, $C_8$, $C_9$, and $C_{10}$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-6}$ alkenyl (or alkenylene), is intended to include $C_2$, $C_3$, $C_4$, $C_5$, and $C_6$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-6}$ alkynyl (or alkynylene), is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic group" is intended to mean any stable 3, 4, 5, 6, or 7-membered monocyclic or bicyclic or 7, 8, 9, or 10-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benztriazolyl, benzisoxazolyl, oxindolyl, benzoxazolinyl, and isatinoyl. Also included are fused ring and spiro compounds containing, for example, the above heterocycles.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Also included is Glaxo's combination of AZT and 3TC. Examples of non-nucleoside RT inhibitors include, but are no limited to, DPC082 (DuPont, (+)-4-Cyclopropylethenyl-5,6-difluoro-4-trifluoromethyl-3,4-dihydro-2(1H)-quinazolinone), DPC083 (DuPont, (−)-6-chloro- 4-E-cyclopropylethenyl-4-trifluoromethyl-3,4-dihydro-2(1H)-quinazolinone), DPC961 (DuPont, (−)-6-chloro-4-cyclopropylethynyl-4-trifluoromethyl-3,4-dihydro-2(1H)-quinazolinone), DPC963 (DuPont, (+)-4-Cyclopropylethynyl-5,6-difluoro-4-trifluoromethyl-3,4-dihydro-2(1H)-quinazolinone), AG1549 (Warner Lambert/Shionogi), delavirdine (Pharmacia and Upjohn U90152S), efavirenz (DuPont), nevirapine (Boehringer Ingelheim), Ro 18,893 (Roche), trovirdine (Lilly), MKC-442 (Triangle), HBY 097 (Hoechst), ACT (Korean Research Institute), UC-781 (Rega Institute), UC-782 (Rega Institute), RD4-2025 (Tosoh Co. Ltd.), and MEN 10979 (Menarini Farmaceutici).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject.

Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference. In the Schemes which follow, $R^1$ is shown as a $CF_3$ group, but could be any one of the presently described $R^1$ groups.

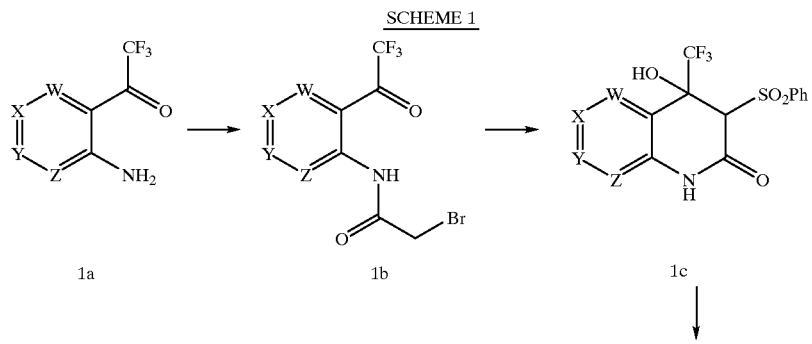

SCHEME 1

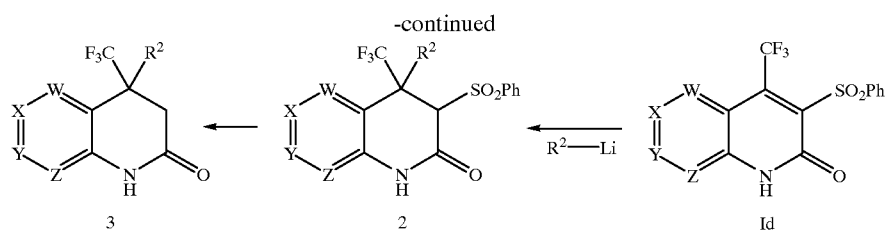

Scheme 1 illustrates a method of making tetrahydroquinolinone intermediates. An appropriately substituted aminoketone is acylated and the resulting amide cyclized in the presence of benzenesulfinate to give alcohol 1c. Dehydration with base provides the α,β-unsaturated ketone 1d which can be modified via a lithium or grignard reagent to give 2. Sulfone reduction can be achieved with Al/Hg or other known methods of reduction to leave intermediate 3.

Scheme 2 depicts modification of intermediate 3 into a 1,3-benzodiazepin-2-one. Compound 3 is protected as amide 4 using Boc-anhydride and ring opened to hydroxamide 5. Lossen rearrangement and deprotection can then be accomplished with tosyl chloride and based followed by trifluoracetic acid to give the desired 1,3-benzodiazepin-2-one 6.

Scheme 3 illustrates a method of reducing acetylene 6 to cis-olefin 7 using $NH_2OSO_3H$ and DIEA. Other methods known to reduce alkynes to alkenes could also be used. In Scheme 3 and the Schemes which follow, G can be $R^3$, $R^4$, $R^5$, $R^6$ or a combination of two or more of these groups.

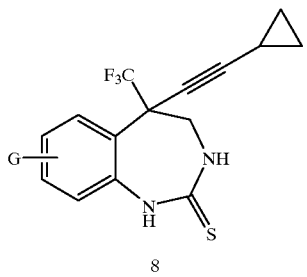

Thioureas of the present invention can be formed as shown in Scheme 4 from their corresponding ureas. Urea 6 is initially converted into a halo-imine via a chlorinating agent such as $POCL_3$ which is then further transformed into thiourea 8 with $NH_2C(S)NH_2$.

An alternative method of preparing compounds of the present invention is shown below in Scheme 5 and proceeds through a nitro-olefin intermediate.

SCHEME 5

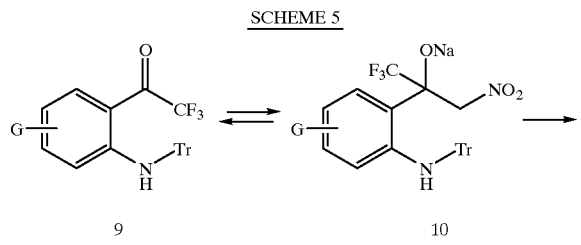

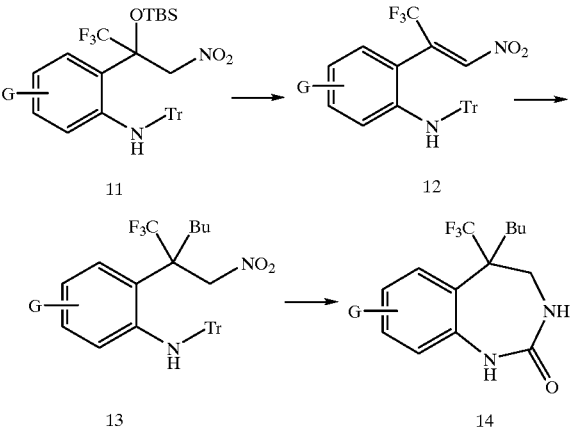

Starting from appropriately substituted ketone 9, nitromethane is added and alkoxide 10 is quenched with a protecting group like TBS-Cl to provide silyl ether 11. Nitro-olefin 12 can be formed by heating 11 in the presence of a base (e.g., $K_2CO_3$). $R^2$ (e.g., butyl) can be attached via grignard addition (e.g., BuMgCl), $(R^2)_3Al$ addition (e.g., (cyclopropylethyl)$_3$Al) or other known methods of addition to nitro-olefins. Modification to 14 can be achieved by reduction of the nitro group to an amino group, deprotection of the aniline amine and finally cyclization with a carbonyl reagent like CDI.

SCHEME 6

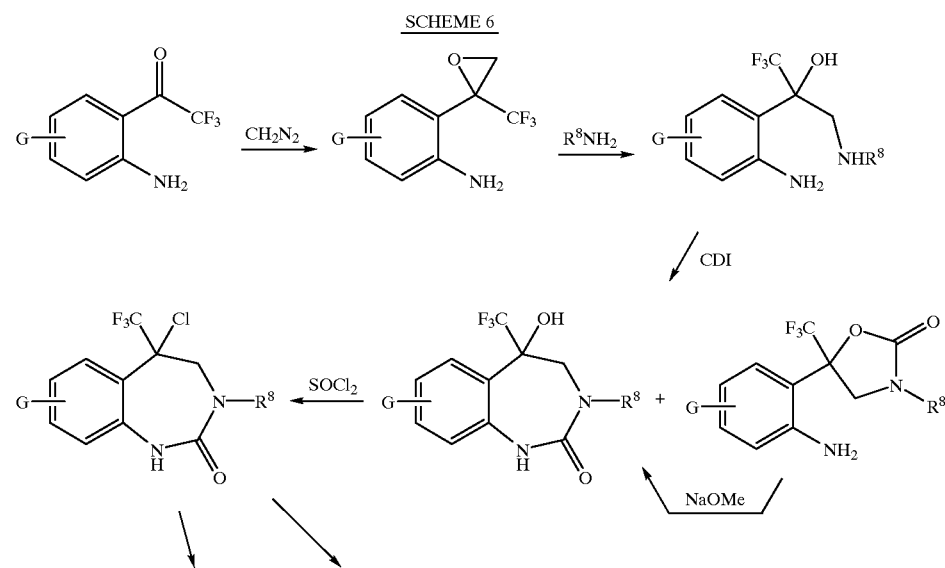

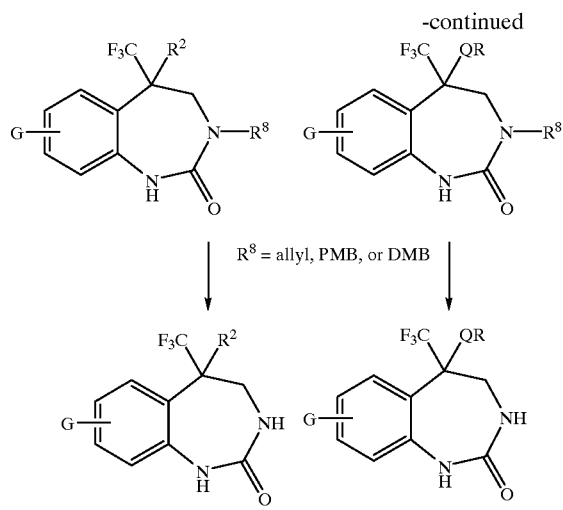

R⁸ = allyl, PMB, or DMB

An alternate means of preparing compounds of the present invention is presented in Scheme 6. The trifluoromethyl ketone is treated with diazomethane, dimethylsulfonium methylide, or dimethylsulfoxonium methylide to give the epoxide. The epoxide is then reacted with a primary amine to give the ring opened alcohol which on treatment with N,N'-carbonyldiimidazole affords a mixture of 5- and 7-membered cyclic amides. Treatment of this mixture with sodium methoxide or triethylamine in ethanol converts it to the desired 7-membered cyclic urea. In addition to N,N'-carbonyldiimidazole, conversion to the cyclic urea can also be accomplished with phosgene, triphosgene, methylchloroformate or a number of similar reagents well-known to practitioners of the art. Treatment of the cyclic urea with thionyl chloride gives the chloride, a compound which when treated with a lithium reagent or a Grignard reagent affords the $R^2$ substituted compound ($R^2$=alkyl, aryl, alkynyl, or alkenyl). Reaction of the chloride with an amine, an alkoxide, or a thioalkoxide gives the QR substituted compound (Q=O, S, NH). For the synthesis of compounds of the invention in which $R^8$=H, it is preferred to open the epoxide with an amine ($R^8NH_2$) whose alkyl group ($R^8$) can be removed in the final synthetic step. Several such removable alkyl groups are well known to practitioners of the art, preferred examples of which are allyl, p-methoxybenzyl (PMB) and 2,4-dimethoxybenzyl (DMB). The allyl group can be removed by treatment with rhodium chloride followed by aqueous acid. The PMB and DMB groups can be removed by catalytic hydrogenation, treatment with a strong acid such as trifluoroacetic acid, or by treatment with an oxidizing agent such as ceric ammonium nitrate, DDQ, or sodium persulfate.

SCHEME 7

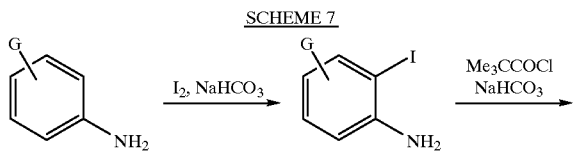

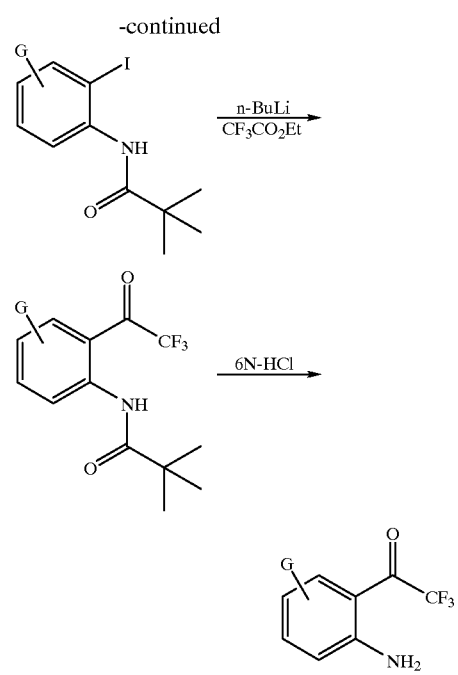

Scheme 7 describes a means of obtaining an aminoketone useful in the previous schemes. After iodination of an appropriate aniline, the trifluoromethyl group can be introduced using a strong base and ethyl trifluoroacetate.

SCHEME 8

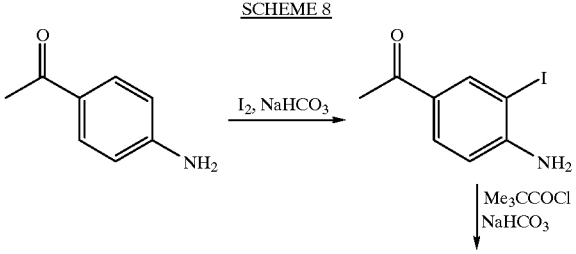

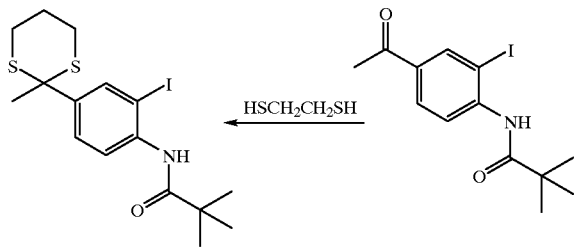

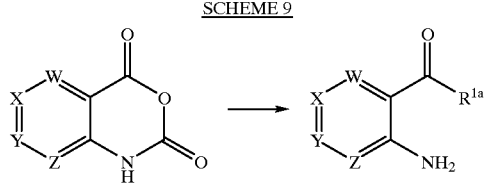

SCHEME 9

Because certain benzo-substituents are incompatible with the methods of the previous schemes, it may be necessary to protect these groups before forming the desired product. In Scheme 8 there is shown a means of obtaining carbonyl-substituted iodo-anilines which can be modified as shown in Scheme 7. After iodination of an acetyl-aniline, the acetyl group is protected by means well known to those of skill in the art, such as using 1,3-propanedithiol. Deprotection of the ketone can then be achieved using $HgCl_2$ and HgO or other means well known to those of skill in the art.

In addition to the methods of obtaining keto-anilines described previously, nucleophilic opening of isatoic anhydrides can also be used as shown in Scheme 9. This reaction is accomplished by using an anionic nucleophile of the group $R^{1a}$. See Mack et al, *J. Heterocyclic Chem.* 1987, 24, 1733–1739; Coppola et al, *J. Org. Chem.* 1976, 41(6), 825–831; Takimoto et al, *Fukuoka Univ. Sci. Reports* 1985, 15(1), 37–38; Kadin et al, *Synthesis* 1977, 500–501; Staiger et al, *J. Org. Chem.* 1959, 24, 1214–1219.

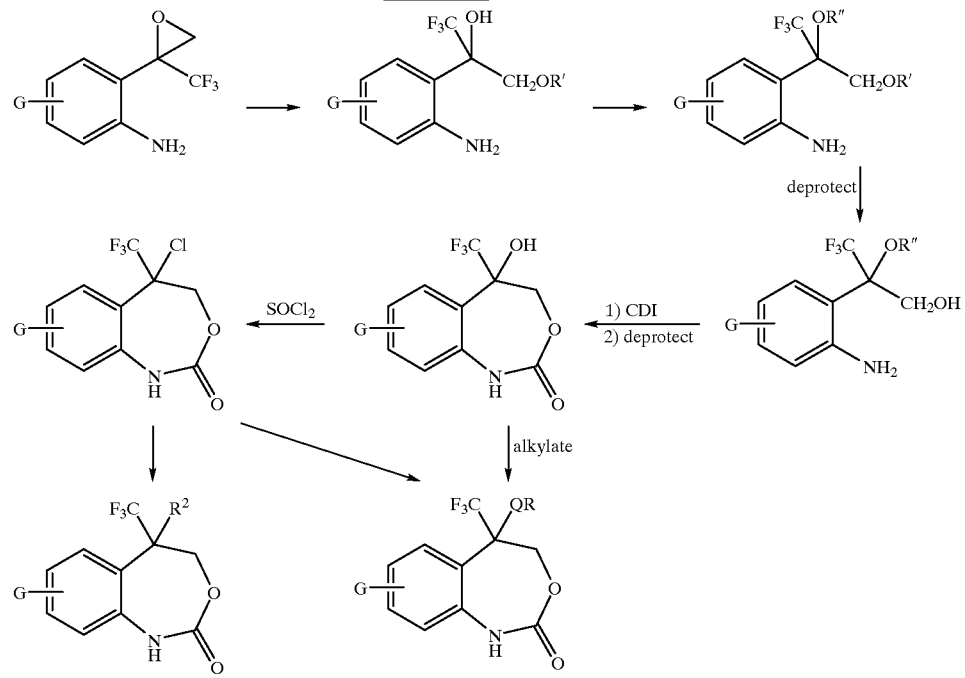

SCHEME 10

The 1,3-benzoxazepinones of this invention can be synthesized as described in Scheme 10. The starting epoxide can be ring-opened with an alkoxide (NaOR', or KOR') in which R' is a protecting group which can be removed later in the synthesis. There are many such removable groups known to practitioners of the art. These include the allyl group, as well as substituted ethyl groups such as 2-trimethylsilylethyl or 2,2,2-trichloroethyl, or substituted benzyl groups such as 3,4-dimethoxybenzyl, p-nitrobenzyl, and diphenylmethyl. The next step is to protect the tertiary alcohol with a second protecting group (R") which is stable to the conditions for the removal of the first protecting group (R'). This second protecting group can be one of the allyl, substituted ethyl, or substituted benzyl groups as described above, or it can be a silyl group (such as triethylsilyl, t-butyldimethylsilyl, or t-butyldiphenylsilyl). There are many combinations of two selectively removable protecting groups which are well known to practitioners of the art. Removal of the first protecting group affords the primary alcohol which upon treatment with N,N'-carbonyldiimidazole or phosgene followed by removal of the second protecting group affords the cyclic carbamate. Treatment of the cyclic carbamate with thionyl chloride converts the tertiary alcohol to a chloride. This compound when treated with a lithium reagent or a Grignard reagent affords the $R^2$ substituted compound ($R^2$=alkyl, aryl, alkynyl, or alkenyl). Reaction of the chloride with an amine, an alkoxide, or a thioalkoxide gives the QR substituted compound (Q=O, S, NH). Additionally, compounds of this invention in which Q=O can also be prepared by direct alkylation of the tertiary alcohol.

One enantiomer of a compound of Formula I may display superior activity compared with the other. Thus, the following stereochemistries are considered to be a part of the present invention.

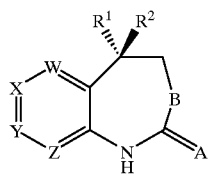

Ia

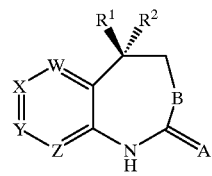

Ib

When required, separation of the racemic material can be achieved by HPLC using a chiral column as exemplified in Examples 27–34 (Scheme 4) or by a resolution using a resolving agent such as camphonic chloride as in Thomas J. Tucker, et al, *J. Med. Chem.* 1994, 37, 2437–2444. A chiral compound of Formula I may also be directly synthesized using a chiral catalyst or a chiral ligand, e.g. Mark A. Huffman, et al, *J. Org. Chem.* 1995, 60, 1590–1594.

Other features of the invention will become apparent in the course of the following descriptions of exemplary embodiments which are given for illustration of the invention and are not intended to be limiting thereof.

EXAMPLES

Abbreviations used in the Examples are defined as follows: "° C." for degrees Celsius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography, "ACN" for acetic anhydride, "CDI" for carbonyl diimidazole, "DIEA" for diisopropylethylamine, "DIPEA" for diisopropylethylamine, "DMAP" for dimethylaminopyridine, "DME" for dimethoxyethane, "EDAC" for 1-(3-dimethylaminopropyl)-3-ethylcarbodiimide hydrochloride, "LAH" for lithium aluminum hydride, "TBAF" for tetrabutylammonium fluoride, "TBS-Cl" for t-butyldimethylsilyl chloride, and "TEA" for triethylamine.

Example 1

Preparation of 7-chloro-5-(2-cyclopropylethynyl)-1,5-dihydro-5-(trifluoromethyl)-1,3-benzodiazepin-2-one

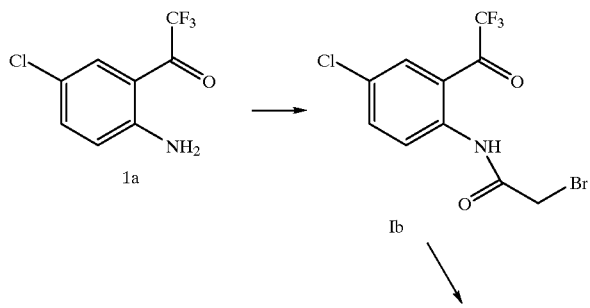

-continued

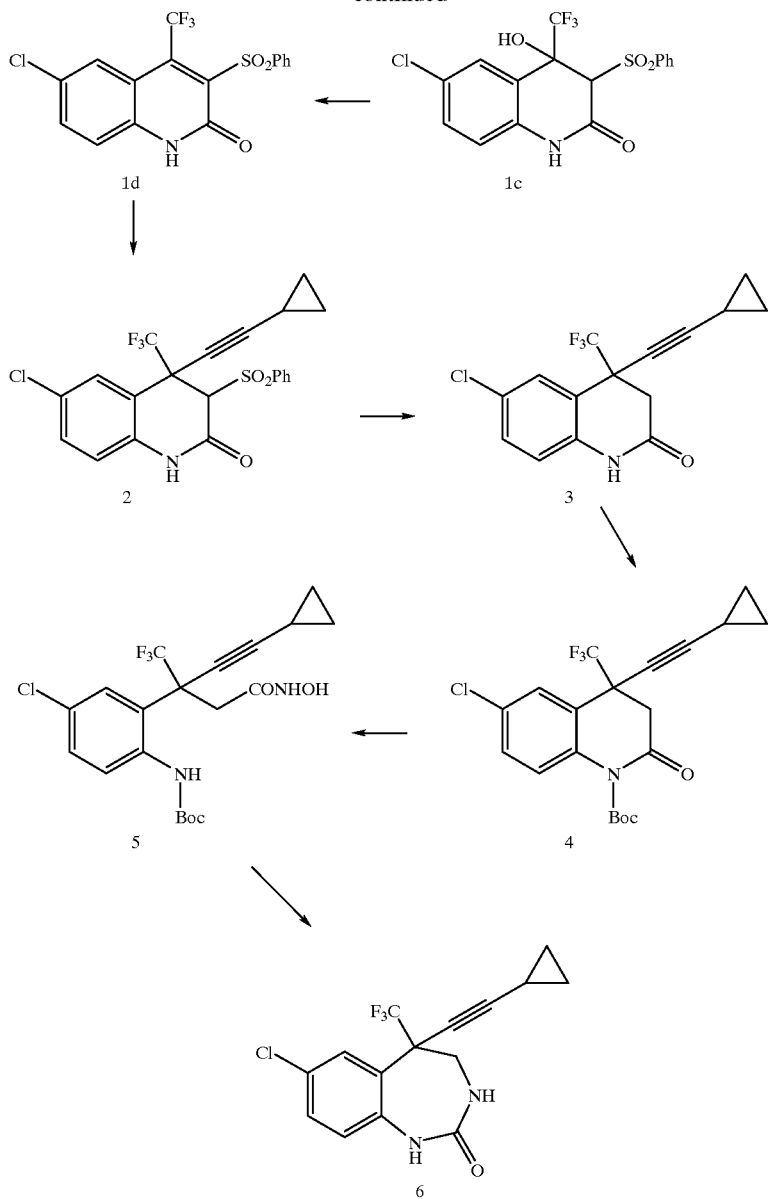

To a solution of amino ketone 1a (3.02 g, 13.54 mmol) in THF (55 mL) at room temperature was added potassium carbonate (4.67 g, 33.85 mmol) followed by bromoacetyl bromide (1.5 mL, 16.93 mmol) and the resulting reaction mixture was allowed to stir at room temperature for 3 hours. The reaction mixture was poured onto water and extracted with ethyl acetate (3×100 mL). The combined ethyl acetate extracts were dried over anhydrous $Na_2SO_4$ and concentrated in vacuo to give a yellow oil 1b. This product was used in the next step of the synthetic sequence without further purification.

To a solution of bromide 1b (crude product, 13.54 mmol) in DMF (55 mL) at room temperature was added sodium benzenesulfinate (4.44 g, 27.08 mmol) and the resulting reaction mixture was allowed to stir at room temperature for 18 hours. The reaction mixture was poured onto water and extracted with ethyl acetate (3×100 mL). The combined ethyl acetate extracts were dried over anhydrous $Na_2SO_4$ and concentrated in vacuo. The group is triturated with hexanes (1 L) and dried in vacuo to give 4.88 g an off-white solid 1c (5.49 g theoretical, 89%). $^1$H NMR (300 MHz, DMSO-$d_6$) δ 11.0(br s, 1H), 7.96(s, 1H), 7.76(d, 2H, J=8 Hz), 7.66(m, 1H), 7.51(m, 2H), 7.44(s, 1H), 7.33(m, 1H), 6.82(d, 1H, J=8 Hz), 4.47(s, 1H). $^{19}$F NMR (282 MHz, DMSO-$d_6$) δ −80.99(s, 3F). High resolution mass spec: calculated for $C_{16}H_{11}NO_4F_3ClS(M+H)+$: 405.0042, found 405.0049.

To a slurry of the tertiary alcohol 1c (6.815 g, 16.83 mmol) in methylene chloride (100 mL) at room temperature was added 4-(dimethylamino)pyridine (4.11 g, 33.65 mmol) followed by acetic anhydride (3.5 mL, 37.03 mmol) and the resulting reaction mixture is allowed to stir at room temperature for 18 hours. The reaction mixture was poured onto water and extracted with ethyl acetate (3×100 mL). The ethyl acetate extracts were washed with saturated $NaHCO_3$ and dried over anhydrous $Na_2SO_4$ and concentrated in vacuo. The group is triturated with hexanes (1 L) and dried in vacuo to give 6.06 g an off-white solid 1d (93%). Anal.

($C_{16}H_9NO_3F_3ClS$) calcd: C, 49.56; H, 2.35; N, 3.61; Cl, 9.14; F, 14.70; S, 8.28. Found: C, 49.26; H, 2.68; N, 3.30; Cl, 9.23; F, 14.49; S, 8.13.

To a 0° C. solution of cyclopropyl acetylene (48% purity, 14.6 mL, 80.9 mmol) in THF (95 mL) was syringed 1.6 M BuLi in hexane (46 mL, 73.5 mmol). After the reaction was stirred for 15–30 min. at 0° C., 1 ( 9.5 g, 24.5 mmol) was added as a solid and stirred for 2 h. The reaction was quenched with saturated $NH_4Cl$. The reaction was partitioned between EtOAc and saturated $NH_4Cl$, washed with brine, dried ($Na_2SO_4$) and evaporated to give a solid. Flash chromatography (50% EtOAc/hexane) gave a white solid 2 (6.6 g, 60% yield).

A mixture of 2 (6.6 g, 14.5 mmol), Al/Hg in THF (90 mL) and water (10 mL) was refluxed for 1 h. The reaction was filtered through celite, partitioned between EtOAc and water, washed with brine, dried ($Na_2SO_4$) and evaporated to give a solid 3 (4 g, 90% yield). $MH^+=314.0559$.

A solution of 3 (4 g, 12.8 mmol), $(Boc)_2O$ (3.06 g 14 mmol) and DMAP (1.56 g, 12.8 mmol) in ACN (60 mL) was stirred for 1 h. TLC indicated that the ratio of the desired product to starting material was about 3 to 2. More $(Boc)_2O$ (0.6 g, 2.8 mmol) was added and the reaction was stirred for 10 min. TLC showed trace of starting material. The reaction was partitioned between EtOAc and 1N HCl, washed with water, saturated $NaHCO_3$ and brine, dried ($Na_2SO_4$) and evaporated to give an orange solid 4 (4.93 g, 93% yield).

A mixture of 4 (4.63 g, 11.2 mmol), $H_2NOH \cdot HCl$ (3.11 g, 44.8 mmol) and DIEA (7.8 mL, 44.8 mmol) in EtOH (65 mL) was stirred for 2 h. The reaction was diluted with EtOAc, washed with dilute HCl (6×), water, saturated $NaHCO_3$, brine and dried ($Na_2SO_4$) and evaporated to give a thick orange oil 5 (5.3 g, 95% yield).

A solution of 5 (4.94 g, 11 mmol), TsCl (5.32 g, 27.9 mmo) and 1N NaOH (53.2 mL, 53.2 mmol) in dioxane (240 mL) was stirred for 1.5 h. The reaction was partitioned between EtOAc and saturated $NaHCO_3$, washed with brine, and evaporated to give a semi-solid. A solution of the semi-solid in TFA (20 mL) and $CH_2Cl_2$ (200 mL) was stirred for 2 h and evaporated to give a thick oil. The oil was partitioned between EtOAc and saturated $NaHCO_3$ and brine, dried ($Na_2SO_4$) and evaporated to give a thick dark orange oil. Crystallized from dichloroethane to give a white crystalline solid 6 (1.25 g, 40% yield, mp 240–242° C.).

Example 2

Preparation of 6,7-difluoro-5-(2-cyclopropylethynyl)-1,5-dihydro-5-(trifluoromethyl)-1,3-benzodiazepin-2-one

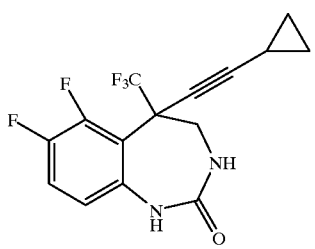

6a

The 6,7-diF analog 6a was prepared using the same sequence as Example 1, but starting from the difluoro analog 1a, mp=232–233° C.

Example 3

Preparation of 7-chloro-5-(2-cyclopropylethenyl)-1,5-dihydro-5-(trifluoromethyl)-1,3-benzodiazepin-2-one

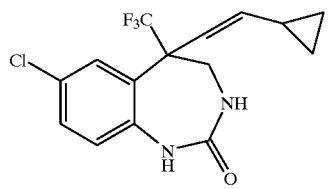

7

A suspension of 6 (60 mg), $NH_2OSO_3H$ (1.5 g) and DIEA (3 mL) in THF (5 mL) was refluxed for 48 h. The reaction was diluted with EtOAc, washed with 1 N HCl (2×), water, brine and dried ($Na_2SO_4$) and evaporated to give a solid which crystallized from dichloroethane to provide a white crystalline solid 7 (30 mg, mp 221–223° C.).

Example 4

Preparation of 7-Chloro-5-(2-cyclopropylethynyl)-1,5-dihydro-5-(trifluoromethyl)-1,3-benzodiazepin-2-thione

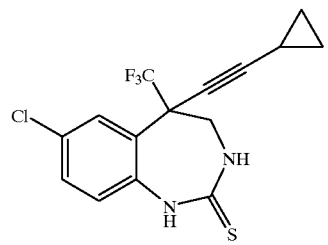

8

A suspension of 6 (50 mg) and $Na_2CO_3$ (24 mg) in $POCl_3$ (1 mL) was heated at 95° C. for 24 h and evaporated to give a semi-solid. The solid and $NH_2CSNH_2$ (63 mg) in EtOH (4 mL) was refluxed over weekend. The reaction was diluted with EtOAc, washed with water and brine, dried ($Na_2SO_4$) and evaporated to give a solid. Flash chromatography (25–50% EtOAc/hexane) gave a white solid (22 mg). Crystallized from dichloroethane gave a white crystalline solid 8 (13 mg, mp 230° C. dec.).

Example 5

Preparation of 7-Chloro-5-(2-n-butyl)-1,5-dihydro-5-(trifluoromethyl)-1,3-benzodiazepin-2-one

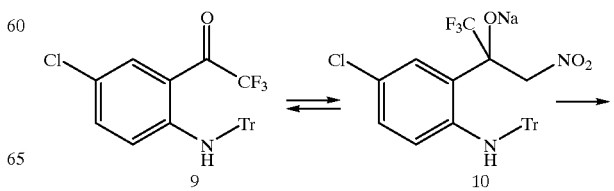

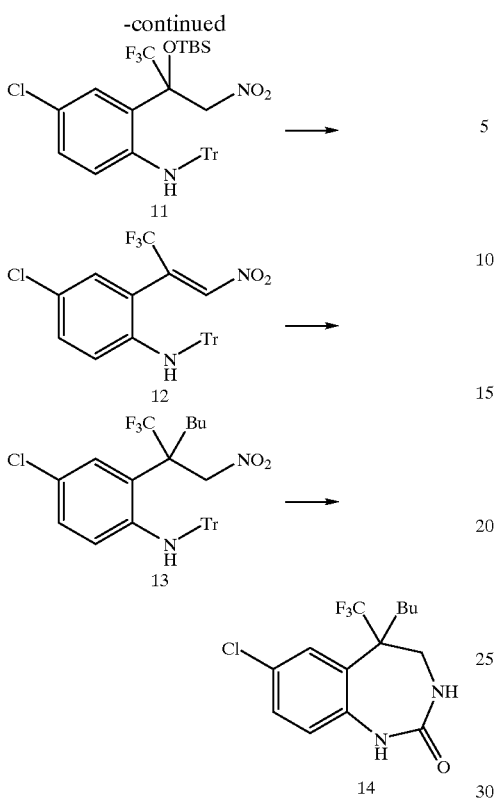

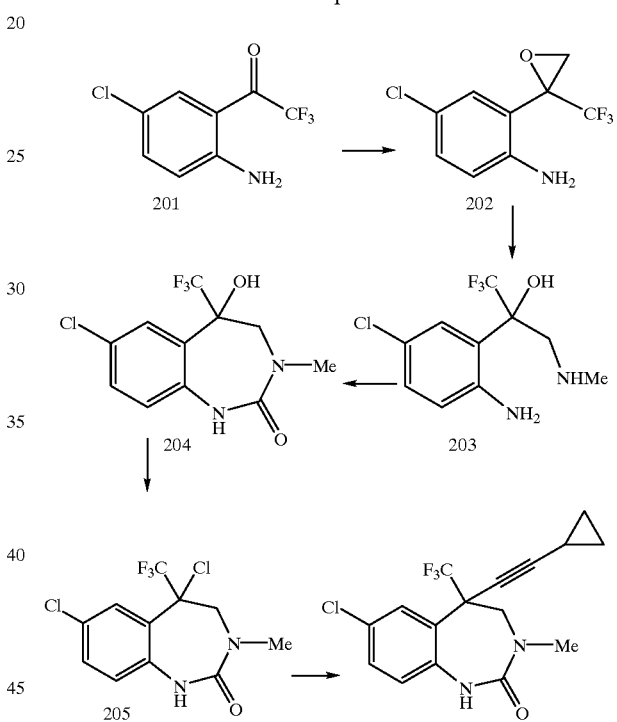

To a solution of 9 (8.48 g, 18.2 mmol) and nitromethane (1.97 mL, 36.4 mmol) in DME (85 mL) was added 60% NaH (2.55 g, 63.8 mmol). After stirring for 1.5 h, TLC indicated that the ratio of the alcohol intermediate 10 to starting material was about 2 to 3. TBS-Cl (13.7 g, 91 mmol) was added and the reaction was stirred for 0.5 h. TLC indicated that the ratio of the desired product 11 to 10 was about 4 to 1. The reaction was stirred for another 2 h. The reaction was diluted with EtOAc and partitioned between EtOAc and saturated NaHCO$_3$ The reaction was filtered and the organic phase was washed with brine, dried (Na$_2$SO$_4$) and evaporated to give an orange oil (22.3 g). The oil was triturated with hexane and washed with same solvent two times to provide a yellow solid 11 (8.2 g, 75% yield).

A mixture of 11 (8.2 g, 13.8 mmol) and K$_2$CO$_3$ (2.2 g) in toluene (80 mL) was refluxed for 0.5 h. The reaction was diluted with EtOAc and washed with water and brine, dried (Na$_2$SO$_4$) and evaporated to give an dark orange oil (7.4 g). The oil was triturated with hot hexane and washed with same solvent two times to provide a brown solid 12 (5 g, 71.5% yield).

To a −78° C. solution of 12 (204 mg, 0.4 mmol) in THF (2 mL) was added 2M BuMgCl in ether (0.6 mL, 1.2 mmol), TLC showed no starting material. The reaction was quenched with saturated NH$_4$Cl and partitioned between EtOAc and saturated NH$_4$Cl, washed with brine, dried (Na$_2$SO$_4$) and evaporated to give an orange oil (240 mg). Flash chromatography (3% EtOAc/hexane) gave a pale yellow glass 13 (94 mg).

A mixture 13 (75 mg), a slurry of Raney nickel (2 mL) and hydrazine monohydrate (0.1 mL) in ethnol (4 mL) was stirred for 2 h. The reaction was filtered with celite and partitioned between EtOAc and water and brine, dried (Na$_2$SO$_4$) and evaporated to give an orange oil (85 mg). Flash chromatography (20% EtOAc/hexane) gave a pale yellow glass (46 mg). A solution of the glass (46 mg) in MeOH (1 30 mL) and concentrated HCl (0.1 mL) was stirred for 15 min. and filtered off. The filtrate was partitioned between EtOAc and 1N NaOH and brine, dried (Na$_2$SO$_4$) and evaporated to give an orange oil (20 mg). A solution of the oil (20 mg) and carbonyl diimidazole (33 mg) in THF (1 mL) was stirred overnight. The solvent was evaporated to give an oil which was triturated with Et$_2$O/hexane/CH$_2$Cl$_2$ to provide a fine powder 14 (5.6 mg, mp 174–176° C.).

An alternative means of converting 12 to 13 is as follows. To a −78° C. solution of 12 (100 mg, 0.2 mmol) in toluene (2 mL) was added 1M (i-Bu)$_3$Al in toluene (0.4 mL, 0.4 mmol), TLC showed no starting material. The reaction was quenched with 0.1M HCl and partitioned between EtOAc and 0.1M HCl, washed with brine, dried (Na$_2$SO$_4$) and evaporated to give an orange oil 13 (121 mg).

Example 6

Preparation of 7-chloro-5-(2-cyclopropylethynyl)-1, 5-dihydro-3-methyl-5-(trifluoromethyl)-1,3-benzodiazepin-2-one A solution of approximately 15 mmoles of diazomethane in 40 mL of ether was generated from 5 g of Diazald® following the directions provided by the vender (Aldrich Chemical Company). This solution was added to a solution of 201 (2.6 g, 11.6 mmoles) in 10 mL of ether and the reaction mixture was stirred for 3 hr at room temperature at which time the showed complete conversion to epoxide 202. Excess diazomethane was quenched by the addition of acetic acid, 10 mL of ethanol was added, and the solution was concentrated to a volume of approximately 10 mL on a rotary evaporator. To this solution was added 20 mL of a solution of 33% methylamine in ethanol and the mixture was stirred at room temperature overnight. Evaporation of the solvent under reduced pressure afforded 203 (3.4 g) a semisolid product which was used without purification in the next reaction.

To a solution of 203 (2.9 g, 10.8 mmol) in 50 mL of dry THF was added N,N'-carbonyldiimidazole (2.6 g, 16.2 mmol) and the reaction mixture was stirred for 1.75 h at ambient temperature. An additional 500 mg of N,N'- carbonyldiimidazole was added and the reaction was allowed to procede for an additional 30 min. Sodium methoxide in methanol (10 mL of a 3.24M solution) was added and the mixture was refluxed for 30 min. The cooled mixture was poured onto aqueous ammonium chloride, and this mixture was extracted twice with ethyl acetate. The combined extracts were dried over sodium sulfate and evaporated to an orange oil. Flash chromatography (50–70% EtOAc/hexane) gave after washing with methylene chloride a white solid 204 (1.5 g, 42.5% yield).

To a solution of 204 (1.17 g, 3.97 mmol) in 50 mL of dry THF was added triethylamine (2.3 mL,16.67 mmol) and thionyl chloride (1.2 mL, 15.88 mmol). After stirring 15 min at ambient temperature, 25 mL of methanol was added and this mixture was stirred for 15 min before being poured onto aqueous sodium bicarbonate. The mixture was extracted with ether and the extract was dried over magnesium sulfate and concentrated to a yellow solid 205 (1.18 g, 95% yield) which was used without purification.

To a 0° C. solution of cyclopropylacetylene (35% purity, 0.45 mL) in THF (3 mL) was syringed 1.6 M BuLi in hexane (0.625 mL, 1.0 mmol). After the reaction was stirred for 30 min. at 0° C., the reaction mixture was cooled to −50° C., 205 (85 mg, 0.27 mmol) in THF (0.7 mL) was added and the reaction mixture was allowed to warm to room temperature over 2 h. The reaction was poured onto saturated ammonium chloride and was extracted with ether. The extracts were washed with brine, dried over magnesium sulfate and evaporated to give an oil. Flash chromatography (50% EtOAc/hexane) gave after crystallization from ethyl acetate/hexane colorless crystals of the title compound (27 mg, mp 177–178° C.).

Example 7

Preparation of 7-chloro-5-(2-cyclopropylethynyl)-1, 5-dihydro-3-ethyl-5-(trifluoromethyl)-1,3-benzodiazepin-2-one

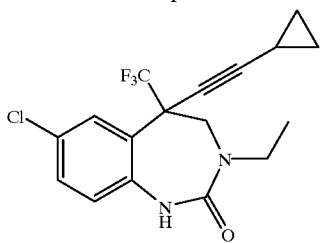

The title compound (mp 186–188° C.) is prepared according to the method of Example 6 by substituting ethylamine for methylamine.

Example 8

Preparation of 7-chloro-5-(2-cyclopropylethynyl)-1, 5-dihydro-3-cyclopropyl-5-(trifluoromethyl)-1,3-benzodiazepin-2-one

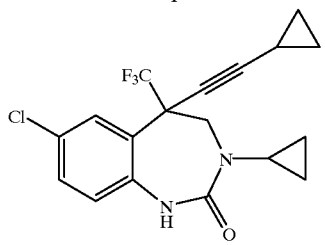

The title compound (mp 195–196° C.) is prepared according to the method of Example 6 by substituting cyclopropylamine for methylamine.

Example 9

Preparation of 7-chloro-5-cyclopropylmethyloxy-1, 5-dihydro-3-methyl-5-(trifluoromethyl)-1,3-benzodiazepin-2-one

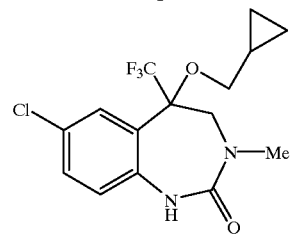

To a solution of cyclopropylcarbinol (250 mg, 3.5 mmol) in 5 mL of dry THF at room temperature was added sodium hydride (50 mg, 2.1 mmol). After 30 min, 205 (150 mg, 0.48 mmol) was added and the reaction mixture was stirred at ambient temperature for 30 min. The reaction was poured onto saturated ammonium chloride and was extracted with ether. The extracts were washed with brine, dried over magnesium sulfate and evaporated to give an oil. Flash chromatography (50% EtOAc/hexane) gave 49 mg of a solid which was recrystallized from ethyl acetate/hexane to afford colorless crystals of the title compound (20 mg, mp 192–193° C.).

Example 10

Preparation of 7-chloro-5-(3-methyl-2-butenyloxy)-1,5-dihydro-3-methyl-5-(trifluoromethyl)-1,3-benzodiazepin-2-one

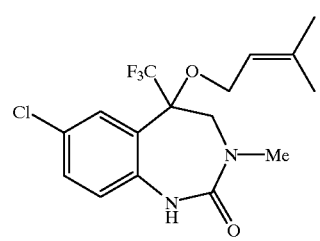

To a solution of 3-methyl-2-buten-1-ol (310 mg, 3.6 mmol) in 5 mL of dry THF at room temperature was added sodium hydride (80 mg, 3.33 mmol). After 30 min, 205 (160 mg, 0.51 mmol) was added and the reaction mixture was stirred at ambient temperature for 30 min. The reaction was poured onto saturated ammonium chloride and was extracted with ethyl acetate. The extracts were washed with brine, dried over magnesium sulfate and evaporated to give an oil. Flash chromatography (30–50% EtOAc/hexane) gave 90 mg of a solid which was recrystallized from ethyl acetate/hexane to afford colorless crystals of the title compound (mp 181–182° C.).

Example 11

Preparation of 7-chloro-5-(3-allyloxy)-1, 5-dihydro-3-methyl-5-(trifluoromethyl)-1,3-benzodiazepin-2-one

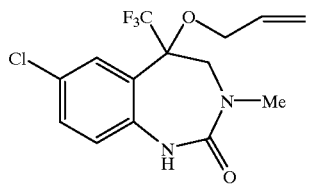

To a solution of allyl alcohol (243 mL, 3.57 mmol) in 5 mL of dry THF at room temperature was added sodium hydride (82 mg, 3.41 mmol). After 30 min, 205 (160 mg, 0.51 mmol) in THF (3 mL) was added and the reaction mixture was stirred at ambient temperature for 35 min. The reaction was poured onto saturated ammonium chloride and was extracted with ethyl acetate. The extracts were washed with brine, dried over magnesium sulfate and evaporated to give an oil. Flash chromatography (40–60% EtOAc/hexane) gave 99 mg of a solid which was recrystallized from ethyl acetate/hexane to afford colorless crystals of the title compound (mp 163–165° C.).

Example 12

Preparation of 7-chloro-5-(3,3-dichloro-2-propenyloxy)-1,5-dihydro-3-methyl-5-(trifluoromethyl)-1,3-benzodiazepin-2-one

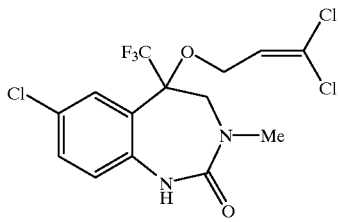

The title compound (mp 148.6–149.9° C.) is prepared according to the method of Example 11 by substituting 3,3-dichloro-2-propenol for allyl alcohol.

Example 13

Preparation of 7-chloro-5-(2-propynyloxy)-1,5-dihydro-3-methyl-5-(trifluoromethyl)-1,3-benzodiazepin-2-one

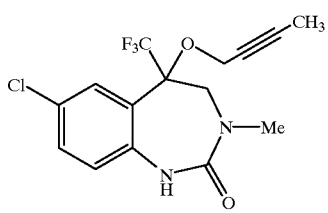

The title compound (mp 229.7–232.1° C.) is prepared according to the method of Example 11 by substituting 2-propyn-1-ol for allyl alcohol.

Example 14

Preparation of 7-chloro-5-(2-fluoro-6-methoxybenzyloxy)-1,5-dihydro-3-methyl-5-(trifluoromethyl)-1,3-benzodiazepin-2-one

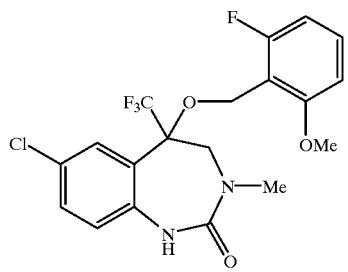

The title compound (mp 172.1–173.8° C.) is prepared according to the method of Example 11 by substituting 2-fluoro-6-methoxybenzyl alcohol for allyl alcohol.

Example 15

Preparation of 7-chloro-5-(cyclopropylmethyloxy)-1,5-dihydro-5-(trifluoromethyl)-1,3-benzodiazepin-2-one

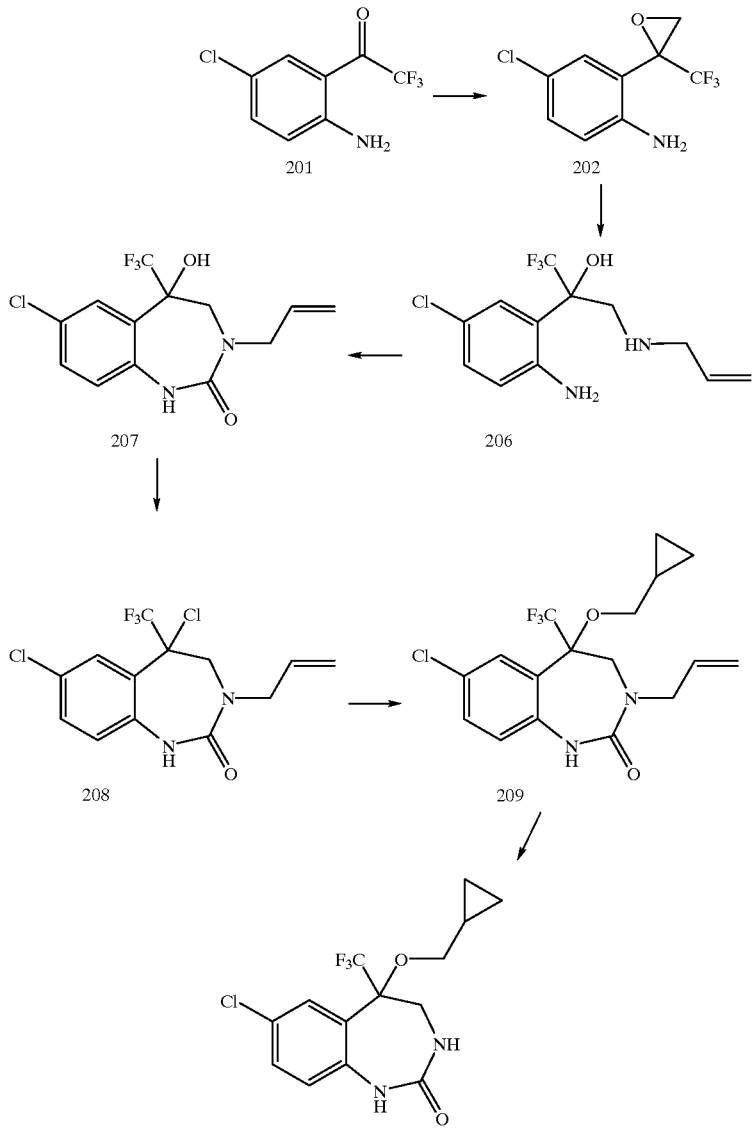

To a solid mixture of 95% sodium hydride (650 mg, 25.7 mmol) and trimethylsulfoxonium iodide (6.0 g, 27 mmol) was added dropwise with stirring over 15 min, 35 mL of dry DMSO. After an additional 20 min of stirring at ambient temperature, hydrogen evolution had ceased, and a solution of 201 (3.35 g, 15 mmol) in dry THF (65 mL) was run in over 3 min. After an additional 2 min, the reaction was quenched with water. The reaction mixture was poured onto water and extracted with ether. The ether layer was washed twice with brine and was dried over magnesium sulfate. Ethanol (15 mL) was added to this ethereal solution and this was concentrated at 20° under reduced pressure to a volume of 15 mL. Allylamine (4.6 g, 81 mmol) was added and the solution was stirred overnight at ambient temperature after which time it was concentrated at 40° to 206 as an oily product.

To a solution of 206 in 65 mL of dry THF was added N,N'-carbonyldiimidazole (2.5 g, 15 mmol) and triethylamine (6.3 mL, 45 mmol) and the reaction mixture was stirred overnight at ambient temperature. Ethanol (25 mL) was added and the mixture was refluxed for 2 h and then evaporated to a small volume. This was taken up in ethyl acetate, and this solution was washed with water, aqueous citric acid, and brine, dried over sodium sulfate and concentrated to an oil. Addition of methylene chloride precipitated the product and 207 was collected as colorless crystals (3.05 g, 63%).

To a solution of 207 (4.6 g, 14.38 mmol) and pyridine (1.393 mL, 17.25 mmol) in 55 mL of dry THF at 0° was added dropwise thionyl chloride (1.865 g, 15.8 mmol). After addition was complete, the cooling bath was removed, and stirring was continued at ambient temperature for 1 h. The reaction mixture was partitioned between water and ethyl acetate, and the organic layer was washed with brine, dried and evaporated to 208 as a crystalline product (4.4 g).

To a solution of cyclopropylmethanol (9 mL) in 45 mL of dry DMSO was added 100% sodium hydride (1.8 g). This was stirred for 3 h at ambient temperature until hydrogen evolution ceased after which time 208 (4.4 g, 13 mmol) was added in one portion. After stirring at ambient temperature for 1 h, the reaction mixture was partitioned between ethyl acetate and aqueous citric acid, and the organic layer was washed with brine, dried (sodium sulfate) and evaporated to an oily product. Flash chromatography (25% EtOAc/hexane) gave after crystallization from hexane 209 (3.0 g).

A solution of 209 (1.2 g) and rhodium trichloride hydrate (60 mg) in ethanol (100 mL) was refluxed for 2 h. The mixture was cooled to 60°, 1N hydrochloric acid (20 mL) was added, and the mixture was stirred at 60° for 2 h. The cooled mixture was partitioned between water and ethyl acetate, and the organic layer was washed with aqueous sodium bicarbonate and brine, dried and evaporated to a solid. Flash chromatography (50–75% ether/hexane) followed by crystallization from methylene chloride-hexane afforded the title compound (840 mg, 78%, mp 185–186° C.) as colorless crystals.

Example 16
Preparation of (S)-7-chloro-5-(cyclopropylmethyloxy)-1,5-dihydro-5-(trifluoromethyl)-1,3-benzodiazepin-2-one

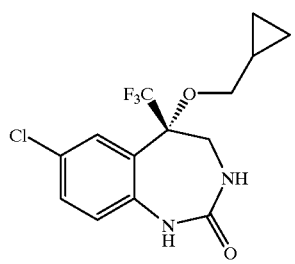

Racemic 7-chloro-5-(cyclopropylmethyloxy)-1,5-dihydro-5-(trifluoromethyl)-1,3-benzodiazepin-2-one (1.2 g) was separated into its constituent enantiomers on a Chiralcel-OD-AMB liquid chromatography column (10% EtOH-hexane). The faster eluting enantiomer was crystallized from ethyl acetate-hexane to give the title compound (335 mg, mp 190–191° C.) which has been assigned the (S) absolute configuration.

Example 17
Preparation of 7-chloro-3-cyclopropyl-5-(cyclopropylmethoxy)-1,5-dihydro-5-(trifluoromethyl)-1,3-benzodiazepin-2-one

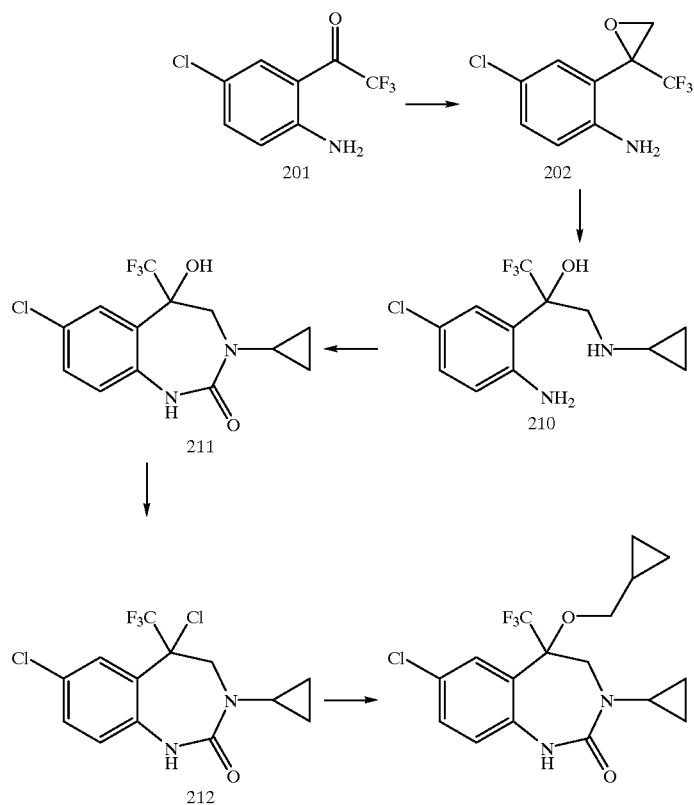

To a solid mixture of 95% sodium hydride (1.94 g, 81 mmol) and trimethylsulfoxonium iodide (17.8 g, 81 mmol) was added dropwise with stirring over 20 min, 100 mL of dry DMSO. After an additional 20 min of stirring at ambient temperature, hydrogen evolution had ceased, and a solution of 201 (10 g, 44.7 mmol) in dry THF (200 mL) was run in over 5 min. After an additional 2 min, the reaction was quenched with water. The reaction mixture was poured onto water and extracted with ether. The ether layer was washed twice with brine and was dried over magnesium sulfate. Ethanol (35 mL) was added to this ethereal solution and this was concentrated at 20° under reduced pressure to a volume of 35 mL. Cyclopropylamine (12.4 mL, 179 mmol) was added and the solution was stirred overnight at ambient temperature and then 2 h at 50° after which time it was concentrated at 40° to 210 (9.4 g) as an oily product.

To a solution of 210 (9.4 g, 31.9 mmol) in 250 mL of dry THF was added N,N'-carbonyldiimidazole (9.3 g, 57.4 mmol) and the reaction mixture was stirred overnight at ambient temperature and evaporated to a solid. Ethanol (150 mL), and triethylamine (13 mL) was added and the mixture was refluxed for 4 h and then evaporated to a small volume. This was taken up in ethyl acetate, and this solution was washed with water, aqueous citric acid, and brine, dried over sodium sulfate and concentrated to an oil. Crystallization from ethyl acetate hexane afforded 2.6 g of a crystalline product. Flash chromatography of the mother liquor on silica gel (40–50% ethyl acetate-hexane) afforded an additional 1.7 g for a total of 4.3 g (42%) of 211 as colorless crystals.

To a solution of 211 (4.3 g, 13.4 mmol) and pyridine (1.6 mL, 20.1 mmol) in 48 mL of dry THF at 0° was added dropwise thionyl chloride (2.0 mL). After addition was complete, the cooling bath was removed, and stirring was continued at ambient temperature for 20 min. The reaction mixture was partitioned between water and ethyl acetate, and the organic layer was washed with brine, dried and evaporated to 212 as a crystalline product (4.2 g).

To a solution of cyclopropylmethanol (9 mL) in 75 mL of dry DMSO was added 100% sodium hydride (840 mg). This was stirred for 1 h at ambient temperature until hydrogen evolution ceased after which time 212 (4.0 g, 11.8 mmol) in DMSO (25 mL) was added. After stirring at ambient temperature for 1 h, the reaction mixture was partitioned between ethyl ether and aqueous citric acid, and the organic layer was washed with brine, dried (sodium sulfate) and evaporated to an oily product. Flash chromatography on silica gel (10–60% EtOAc-hexane) gave after crystallization from ethyl acetate -hexane the title compound (2.15 g, 49%, mp 153.5–155° C.) as colorless crystals.

Example 18

Preparation of (S)-7-chloro-3-cyclopropyl-5-(cyclopropylnethoxy)-1,5-dihydro-5-(trifluoromethyl)-1,3-benzodiazepin-2-one

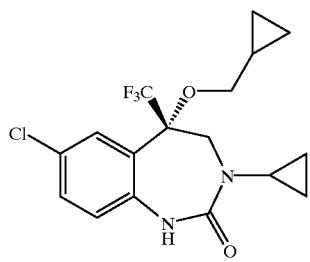

Racemic 7-chloro-3-cyclopropyl-5-(cyclopropylmethoxy)-1,5-dihydro-5-(trifluoromethyl)-1,3-benzodiazepin-2-one (1.1 g) was separated into its constituent enantiomers on a Chiralcel OD-H liquid chromatography column (10% EtOH-supercritical carbon dioxide). The faster eluting enantiomer was crystallized from hexane to give the title compound (320 mg, mp 66–68°) which has been assigned the (S) absolute configuration.

Example 19

Preparation of 7-chloro-3-cyclopropyl-5-propyloxy-1,5-dihydro-5-(trifluoromethyl)-1,3-benzodiazepin-2-one

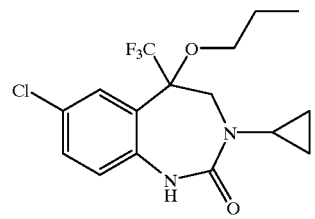

The title compound (mp 153–154°) is prepared according to the method of Example 17 by substituting propanol for cyclopropylmethanol.

Example 20

Preparation of 7-chloro-3-cyclopropyl-5-propylthio-1,5-dihydro-5-(trifluoromethyl)-1,3-benzodiazepin-2-one

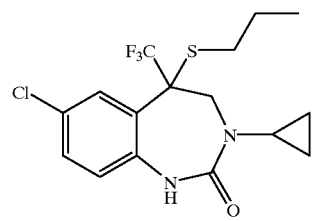

The title compound (mp 150–151° C.) is prepared according to the method of Example 17 by substituting propanethiol for cyclopropylmethanol.

Example 21

Preparation of 7-chloro-3-cyclopropyl-5-allylthio-1,5-dihydro-5-(trifluoromethyl)-1,3-benzodiazepin-2-one

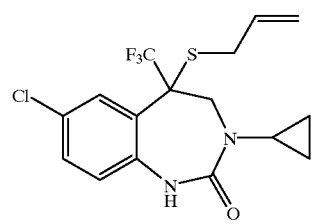

The title compound (mp 144–145.5° C.) is prepared according to the method of Example 17 by substituting allyl mercaptan for cyclopropylmethanol.

Example 22

Preparation of 7-chloro-3-cyclopropyl-5-allyloxy-1,5-dihydro-5-(trifluoromethyl)-1,3-benzodiazepin-2-one

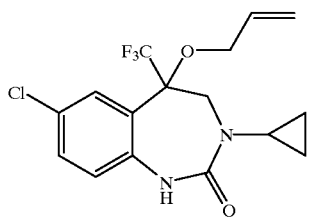

The title compound (mp 120–121° C.) is prepared according to the method of Example 17 by substituting allyl alcohol for cyclopropylmethanol.

Example 23

Preparation of 7-chloro-3-cyclopropyl-5-(3-methyl-2-butenyloxy)-1,5-dihydro-5-(trifluoromethyl)-1,3-benzodiazepin-2-one

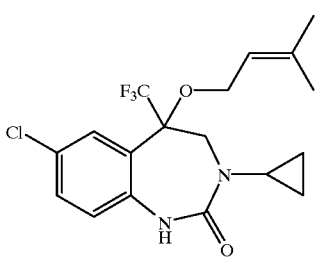

The title compound (mp 130–131° C.) is prepared according to the method of Example 17 by substituting 3-methyl-2-butenol for cyclopropylmethanol.

Example 24

Preparation of 7-chloro-3-cyclopropyl-5-cyclobutylmethyloxy-1,5-dihydro-5-(trifluoramethyl)-1,3-benzodiazepin-2-one

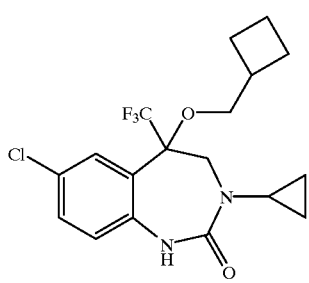

The title compound (mp 158–159° C.) is prepared according to the method of Example 17 by substituting cyclobutylmethanol for cyclopropylmethanol.

Example 25

Preparation of 7-chloro-3-cyclopropyl-5-(1-methylcyclopropyl)methyloxy-1,5-dihydro-5-(trifluoromethyl)-1,3-benzodiazepin-2-one

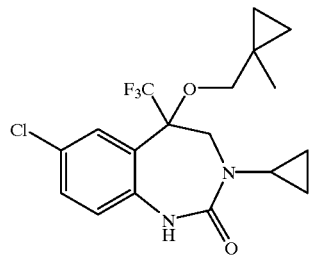

The title compound (mp 166–167° C.) is prepared according to the method of Example 17 by substituting (1-methylcyclopropyl)methanol for cyclopropylmethanol.

Example 26

Preparation of 7-chloro-3-cyclopropyl-5-(2-pyridyl)methyloxy-1,5-dihydro-5-(trifluoromethyl)-1,3-benzodiazepin-2-one

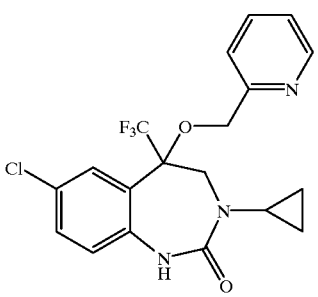

The title compound is (mp 170–171.5° C.) prepared according to the method of Example 17 by substituting 2-(hydroxymethyl)pyridine for cyclopropylmethanol

Example 27

Preparation of 7-chloro-3-isopropyl-5-cyclopropylmethyloxy-1,5-dihydro-5-(trifluoromethyl)-1,3-benzodiazepin-2-one

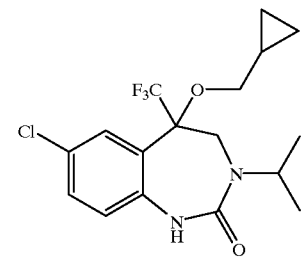

The title compound (mp 169.5–170.5° C.) is prepared according to the method of Example 17 by substituting isopropylamine for cyclopropylamine.

Example 28

Preparation of 7-chloro-3-cyclobutyl-5-cyclopropylmethyloxy-1,5-dihydro-5-(trifluoromethyl)-1,3-benzodiazepin-2-one

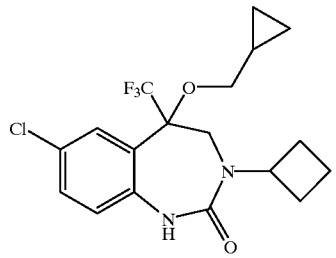

The title compound (mp 156° C.) is prepared according to the method of Example 17 by substituting cyclobutylamine for cyclopropylamine.

Example 29

Preparation of 7-chloro-5-(cyclopropy ethoxy)-1,5-dihydro-3-ethyl-5-(trifluoromethyl)-1,3-benzodiazepin-2-one

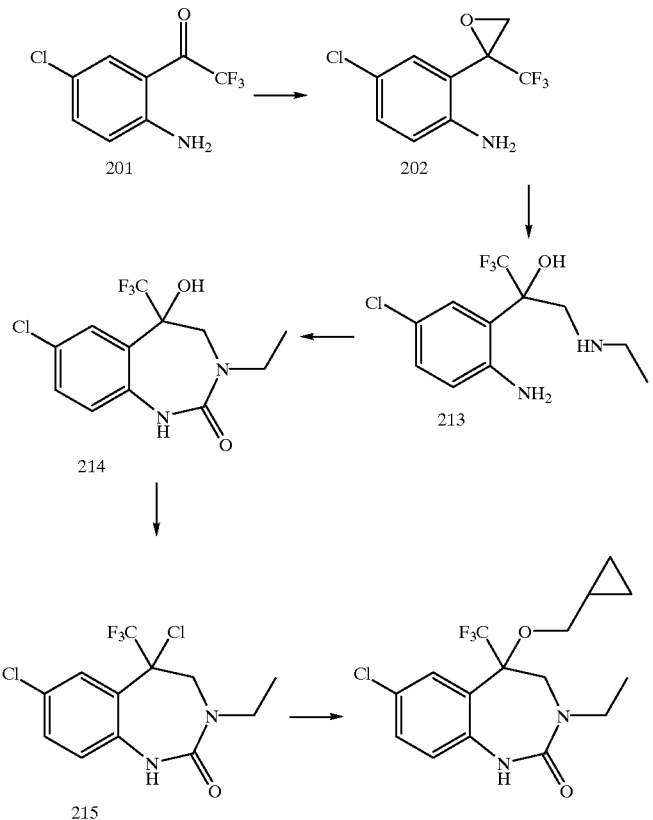

A solution of approximately 28 mmoles of diazomethane in 100 mL of ether was generated from 10 g of Diazald® following the directions provided by the vender (Aldrich Chemical Company). This solution was added to a solution of 201 (5.2 g, 23.2 mmoles) in 20 mL of ether and the reaction mixture was stirred for 3 hr at room temperature at which time the showed complete conversion to epoxide 202. Excess diazomethane was quenched by the addition of acetic acid, 20 mL of ethanol was added, and the solution was concentrated to a volume of approximately 20 mL on a rotary evaporator. To this solution was added 20 mL of a solution of 2M ethylamine in THF and the mixture was stirred in a stoppered flask at 50° for 5 h. Evaporation of the solvent under reduced pressure afforded after purification by flash chromatography on silica gel (20% ethylacetate-hexane) 213 (2.7 g) as an oil.

To a solution of 213 (2.7 g) in 45 mL of dry THF was added N,N'-carbonyldiimidazole (1.8 g), and triethylamine (4.2 mL) and the reaction mixture was stirred overnight at ambient temperature. Ethanol (15 mL) was added and the mixture was refluxed for 3 h, then evaporated to a small volume. This was taken up in ethyl acetate, and this solution was washed eith water, aqueous citric acid, and brine, dried over sodium sulfate and concentrated to an oil. Addition of methylene chloride precipitated the product and 214 was collected as colorless crystals (1.73 g).

To a solution of 214 (1.54 g) and pyridine (0.50 mL) in 20 mL of dry THF at 0° was added dropwise thionyl chloride (0.400 mL) After addition was complete, the cooling bath was removed, and stirring was continued at ambient temperature for 1 h. The reaction mixture was partitioned between water and ethyl acetate, and the organic layer which contained both dissolved and undissolved product was evaporated to 215 as a crystalline product (1.43 g).

To a solution of cyclopropylmethanol (0.20 mL) in 3 mL of dry DMSO was added 100% sodium hydride (36 mg). This was stirred for 30 min at ambient temperature until hydrogen evolution ceased after which time 215 (150 mg) was added in one portion. After stirring at ambient temperature for 20 min, the reaction mixture was partitioned between ethyl acetate and aqueous citric acid, and the organic layer was washed with brine, dried (sodium sulfate) and evaporated to a solid product. This was recrystallized from ethyl acetate-hexane to afford the title compound (85 mg, mp 157–159°) as colorless crystals.

Example 30

Preparation of (S)-7-chloro-5-(cyclopropylmethyloxy)-1,5-dihydro-3-ethyl-5-(trifluoromethyl)-1,3-benzodiazepin-2-one

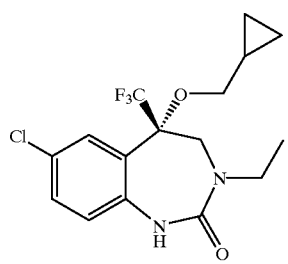

Racemic 7-chloro-5-(cyclopropylmethyloxy)-1,5-dihydro-5-(trifluoromethyl)-1,3-benzodiazepin-2-one (1.7 g) was separated into its constituent enantiomers on a Chiralcel-OD-H liquid chromatography column (10% EtOH-supercritical carbon dioxide). The faster eluting enantiomer was the title compound (603 mg, Mass Spec. (M+H)$^+$ Calc. for $C_{16}H_{19}F_3N_2O_2Cl$: 363.17076; Fd: 363.17088) as an amorphous solid which has been assigned the (S) absolute configuration.

Example 31

Preparation of 7-chloro-3-ethyl-5-(3-methyl-2-butenyloxy)-1,5-dihydro-5-(trifluoromethyl)-1,3-benzodiazepin-2-one

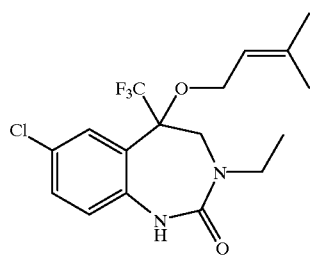

The title compound (mp 158–160° C.) is prepared according to the method of Example 29 by substituting 3-methyl-2-butenol for cyclopropylmethanol.

Example 32

Preparation of 7-chloro-3-ethyl-5-allylthio-1,5-dihydro-5-(trifluoromethyl)-1,3-benzodiazepin-2-one

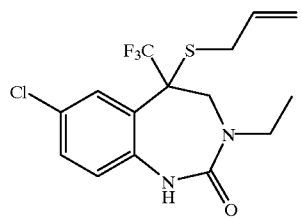

The title compound (mp 138.1–141.8° C.) is prepared according to the method of Example 29 by substituting allyl mercaptan for cyclopropylmethanol.

Example 33

Preparation of 7-chloro-3-ethyl-5-cyclobutylmethyloxy-1,5-dihydro-5-(trifluoromethyl)-1,3-benzodiazepin-2-one

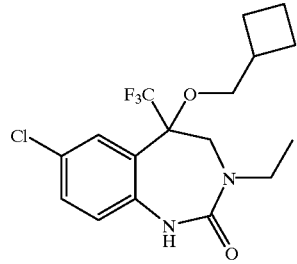

The title compound (Mass Spec. (M+H)$^+$ Calc. for $C_{17}H_{21}F_3N_2O_2Cl$: 377.1244; Fd: 377.1262) is prepared according to the method of Example 29 by substituting cyclobutylmethanol for cyclopropylmethanol.

Example 34

Preparation of 7-chloro-3-ethyl-5-cyclopropylmethylthio-1,5-dihydro-5-(trifluoromethyl)-1,3-benzodiazepin-2-one

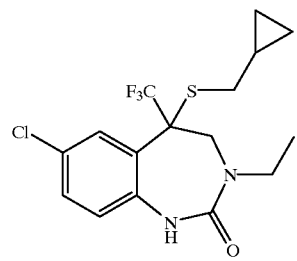

The title compound (mp 152.3–156° C.) is prepared according to the method of Example 29 by substituting cyclopropylmethyl mercaptan for cyclopropylmethanol.

Example 35

Preparation of 7-chloro-3-ethyl-5-(1-methylcyclopropyl)methyloxy-1,5-dihydro-5-(trifluoromethyl)-1,3-benzodiazepin-2-one

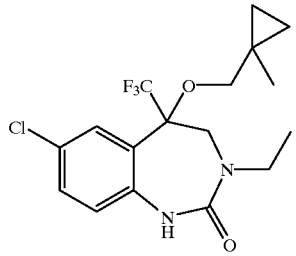

The title compound (mp 171–172.5° C.) is prepared according to the method of Example 29 by substituting (1-methylcyclopropyl)methanol for cyclopropylmethanol.

Example 36

Preparation of 7-chloro-3-propyl-5-cyclopropylmethyloxy-1,5-dihydro-5-(trifluoromethyl)-1,3-benzodiazepin-2-one

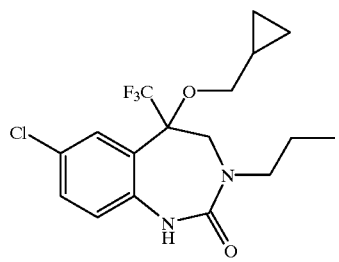

The title compound (mp 155.5–157.5° C.) is prepared according to the method of Example 29 by substituting n-propylamine for ethylamine.

Example 37

Preparation of 7-Fluoro-5-(cyclopropylmethoxy)-1,5-dihydro-5-(trifluoromethyl)-1,3-benzodiazepin-2-one

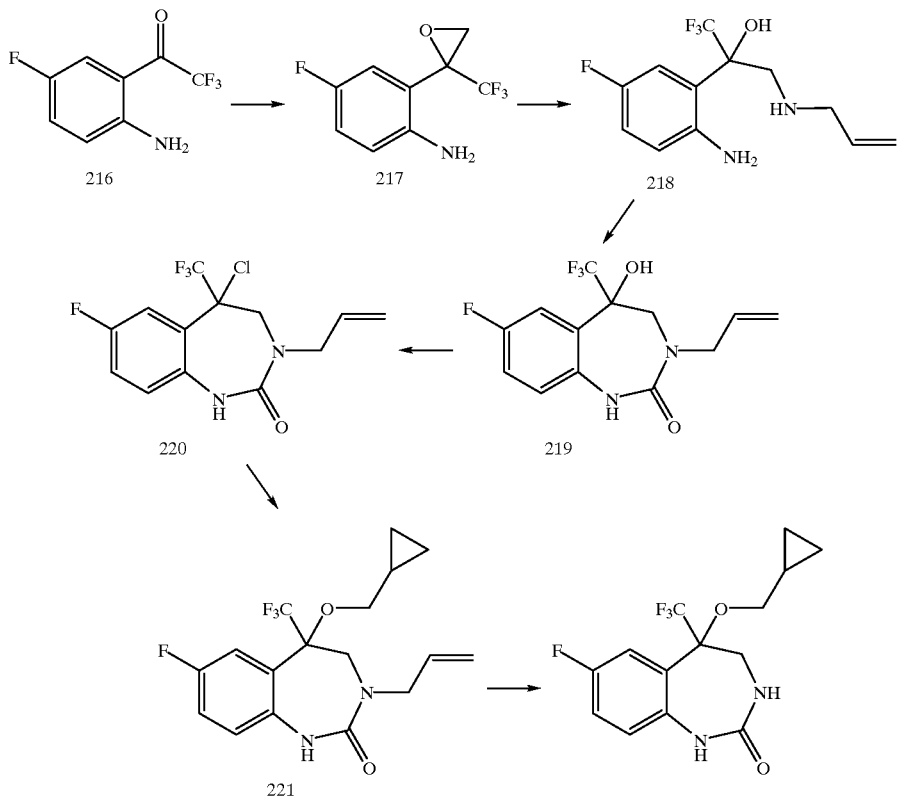

To a 0° solution of N-pivaloyl-4-fluoroaniline (10 g) in 150 mL of dry THF was added dropwise over 20 min 1.6M butyllithium in hexane (77 mL). After stirring at 0° for 1 h, ethyltrifluoroacetate (14.0 mL) was added and the the reaction mixture was allowed to warm to room temperature over 1.5 h. The reaction was quenched by the addition of aqueous ammonium chloride and the mixture was partitioned between water and ether. The ether layer was dried and concentrated to a brown oil (18.3 g) which was used directly in the next reaction.

This oil was dissolved in 15 mL of ethylene glycol dimethyl ether, 75 mL of concentrated aqueous hydrochloric acid was added and the mixture was refluxed for 1.5 h. The cooled reaction mixtured was diluted with water and made basic with solid sodium carbonate. This was extracted with ether, and the extractsa were dried and evaporated to an oil which was purified by flash chromatography on silica gel (10–20% ethyl acetate-hexane) to afford after recrystalization from ethyl acetate-hexane, 2.65 g of 2-amino-5-fluoro-1',1',1'-trifluoroacetophenone 216.

A solution of approximately 15 mmoles of diazomethane in 40 mL of ether was generated from 5 g of Diazald® following the directions provided by the vender (Aldrich Chemical Company) This solution was added to a solution of 2-amino-5-fluoro-1',1',1'-trifluoroacetophenone 216 (2.65 g, 12.8 mmoles) in 10 mL of ether and the reaction mixture was stirred for 5 hr at room temperature at which time the showed complete conversion to epoxide 217. Excess diazomethane was quenched by the addition of acetic acid. To one-half of this solution (containing approximately 6.5 mmol of epoxide) 10 mL of ethanol was added, and the solution was concentrated to a volume of approximately 10 mL on a rotary evaporator. To this solution was added 1.69 mL of allylamine and the mixture was stirred at room temperature overnight. Evaporation of the solvent under reduced pressure afforded a crude product which was purified by flash chromatography on silica gel (10-50% ethyl acetate-hexane) affording 1.05 g of the product 218 as an oil.

To a solution of 218 (1.05 g, 3.77 mmol) in 20 mL of dry THF was added N,N'-carbonyldiimidazole (856 mg) and triethylamine (2.6 mL) and the reaction mixture was stirred overnight at ambient temperature. Ethanol (7 mL) was added and the mixture was refluxed for 6 h. The cooled mixture was poured onto water, and this mixture was extracted twice with ethyl acetate. The combined extracts were dried over sodium sulfate and evaporated. Flash chromatography (20–50% EtOAc/hexane) gave 219 as a white solid (858 mg, 75%).

To a solution of 219 (850 mg) and pyridine (0.339 mL) in 12 mL of dry THF at 0° was added dropwise thionyl chloride (0.407 mL) After addition was complete, the cooling bath was removed, and stirring was continued at ambient temperature for 30 min. The reaction mixture was partitioned between water and ethyl acetate, and the organic layer which contained both dissolved and undissolved product was evaporated to 220 as a crystalline product (785 mg, 87%).

To a solution of cyclopropylmethanol (0.624 mL) in 5 mL of dry DMSO was added 100% sodium hydride (55 mg). This was stirred for 30 min at ambient temperature until hydrogen evolution ceased after which time 220 (250 mg) in DMSO (3.5 mL) was added in one portion. After stirring at ambient temperature for 2 h, the reaction mixture was partitioned between ether and aqueous citric acid, and the organic layer was washed with brine, dried (sodium sulfate) and evaporated to 221 (240 mg) as a solid.

A solution of 221 (135 mg) and rhodium trichloride hydrate (8 mg) in ethanol (10 mL) was refluxed for 1.5 h. The mixture was cooled to 60°, 1N hydrochloric acid (2.5 ML) was added, and the mixture was stirred at 600 for 1 h. The cooled mixture was partitioned between water and ethyl acetate, and the organic layer was washed with aqueous sodium bicarbonate and brine, dried and evaporated to an oil. Crystallization from ethyl acetate-hexane afforded the title compound (55 mg, mp 198–199° C.) as a colorless solid.

Example 38

Preparation of 7-Fluoro-3-ethyl-5-cyclopropylmethyloxy-1,5-dihydro-5-(trifluoromethyl)-1,3-benzodiazepin-2-one

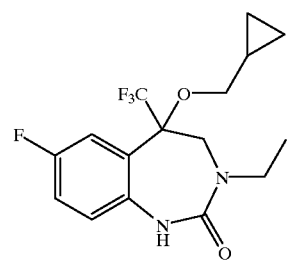

The title compound (mp 156° C.) is prepared according to the method of Example 37 by substituting ethylamine for allylamine, and eliminating the final deprotection step.

Example 39

Preparation of 7-Fluoro-5-(cyclobutylmethoxy)-1,5-dihydro-5-(trifluoromethyl)-1,3-benzodiazepin-2-one

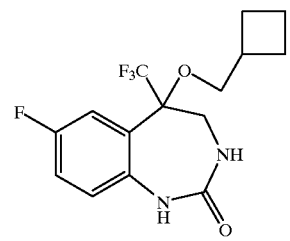

To a solution of cyclobutylmethanol (0.821 mL) in 5 mL of dry DMSO was added 100% sodium hydride (63 mg). This was stirred for 30 min at ambient temperature until hydrogen evolution ceased after which time 220 (280 mg) in DMSO (2 mL) was added in one portion. After stirring at ambient temperature for 2 h, the reaction mixture was partitioned between ether and aqueous citric acid, and the organic layer was washed with brine, dried (sodium sulfate) and evaporated to a crude product which was purified by flash chromatography on silica gel to give a solid (190 mg).

This solid and rhodium trichloride hydrate (10 mg) in ethanol (13 mL) was refluxed for 1.5 h. The mixture was cooled to 60°, 1N hydrochloric acid (3.5 mL) was added, and the mixture was stirred at 60° for 1 h. The cooled mixture was partitioned between water and ethyl acetate, and the organic layer was washed with aqueous sodium bicarbonate and brine, dried and evaporated to an oil. Crystallization from methylene chloride-hexane afforded the title compound (55 mg, mp 190–191° C.) as colorless crystals.

Example 40

Preparation of 7-Fluoro-3-ethyl-5-cyclobutylmethyloxy-1,5-dihydro-5-(trifluoromethyl)-1,3-benzodiazepin-2-one

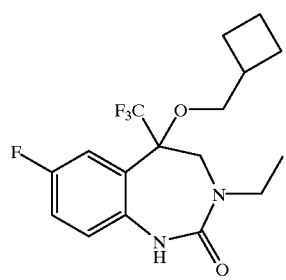

The title compound (mp 137–138° C.) is prepared according to the method of Example 39 by substituting ethylamine for allylamine, and eliminating the final deprotection step.

Example 41

Preparation of 7-chloro-5-[2-(1-methylcyclopropyl)ethynyl]-1,5-dihydro-5-(trifluoromethyl)-1,3-benzodiazepin-2-one

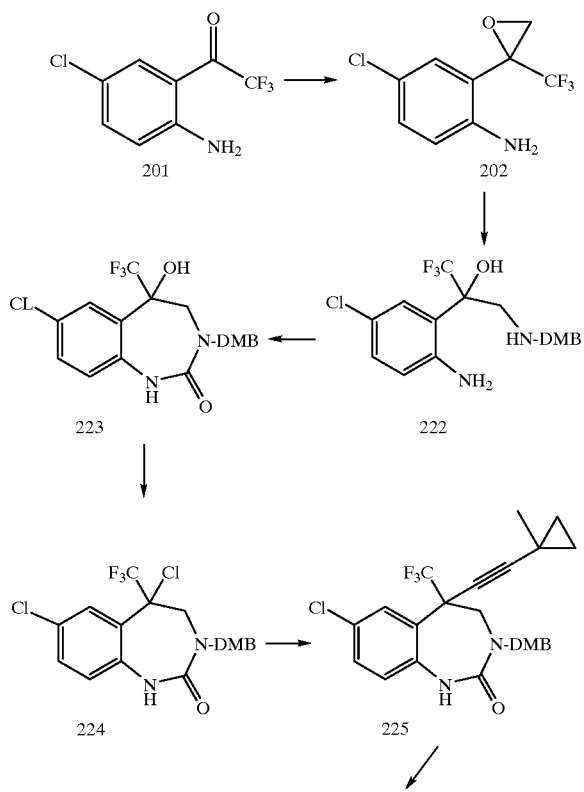

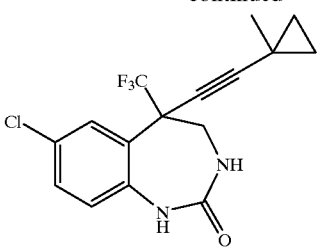

A solution of approximately 60 mmoles of diazomethane in 200 mL of ether was generated from 10 g of Diazald® following the directions provided by the vender (Aldrich Chemical Company). This solution was added to a solution of 201 (11.15 g, 50 mmoles) in 30 mL of ether and the reaction mixture was stirred for 5 hr at room temperature at which time tlc showed complete conversion to epoxide 202. Excess diazomethane was quenched by the addition of acetic acid, 2,4-dimethoxybenzylamine (12 g), and 50 mL of ethanol was added, and the solution was concentrated to a volume of approximately 60 mL on a rotary evaporator. The mixture was stirred overnight at ambient temperature and then for 4 h at 50°. After evaporation of the solvent under reduced pressure, the crude product was dissolved in ether and this solution was washed twice with water. The ether layer was extracted twice with 1N HCl, and the combined extracts were made basic with 1N NaOH and then extracted with ether. The ether extracts were dried and evaporated and the crude product was redissolved in methylene chloride and this solution was washed with 1% aqeous acetic acid, and brine, dried and evaporated to 222 (13.2 g, 65%).

To a solution of 222 (13.0 g) in 150 mL of dry THF was added N,N'-carbonyldiimidazole (6.5 g), and triethylamine (13 mL) and the reaction mixture was stirred 4 h at ambient temperature. Ethanol (75 mL) was added and the mixture was refluxed overnight, then evaporated to a small volume. This was diluted with water and extracted twice with ethyl acetate. The combined extracts were dried and evaporated to a solid which upon trituration with methylene chloride afforded 223 as colorless crystals (10.1 g, 73%).

To a solution of 223 (2.92 g, 6.75 mmol) and pyridine (0.685 mL, 1.2 equiv) in 30 mL of dry THF at 0° was added dropwise thionyl chloride (0.540 mL, 1.1 equiv). After addition was complete, the cooling bath was removed, and stirring was continued at ambient temperature for 1 h. The reaction mixture was partitioned between water and ethyl acetate, and the organic layer which contained both dissolved and undissolved product was evaporated to 224 as a crystalline product (2.4 g, 79%).

To a solution of (1-methylcyclopropyl)acetylene (144 mg, 1.8 mmol) in dry THF (4 mL) at 0° was added 1.6 M butyllithium in hexane (0.99 mL, 1.58 mmol). After 30 min at 0°, the mixture was cooled to −30° and 224 (200 mg, 0.45 mmol) in THF (2 mL) was added dropwise. The reaction mixture was allowed to warm to 0° over 30 min after which time it was poured onto aqueous citric acid and extracted twice with ether. The combined extracts were washed with brine, dried and evaporated to 260 mg of 225 as a solid which was used directly in the next reaction.

A solution of 225 (250 mg) in trifluoroacetic acid (1.5 mL) was stirred at room temperature for 30 min then poured onto aqueous sodium bicarbonate and extracted with ethyl acetate. The combined extracts were washed with brine, dried and evaporated to an impure solid which was purified by flash chromatography on silica gel (20–80% ethyl acetate-hexane) followed by recrystallization from ether-ethyl acetate-hexane to afford the title compound (6 mg, mp 196–198°) as colorless crystals.

Example 42

Preparation of 7-chloro-5-cyclobutylmethyloxy-1,5-dihydro-5-(trifluoromethyl)-1,3-benzodiazepin-2-one

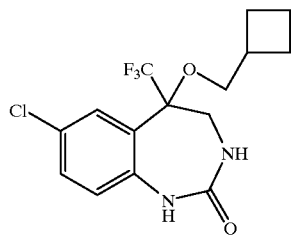

To a solution of cyclobutylmethanol (0.456 mL) in 7 mL of dry THF at room temperature was added sodium hydride (110 mg). After 30 min, chloride 224 (300 mg) in THF (3.5 mL) was added and the reaction mixture was stirred at ambient temperature for 1 h. The reaction was poured onto saturated ammonium chloride and was extracted with ethyl acetate. The extracts dried over magnesium sulfate and evaporated to give a crude product which was purified by flash chromatography (20–40% EtOAc/hexane) gave 124 mg solid product.

A solution of this material in 2.5 mL of trifluoroacetic acid was stirred at room temperature for 30 min and then partitioned between ethyl acetate and aqueous sodium bicarbonate. The organic phase was dried and evaporated to a crude product which was purified by flash chromatography on silica gel (50% ethyl acetate-hexane) to afford the title compound (74 mg, mp 201.6–202.9° C.) as colorless crystals.

Example 43

Preparation of 7-chloro-5-(3-methyl-2-butenyloxy)-1,5-dihydro-5-(trifluoromethyl)-1,3-benzodiazepin-2-one

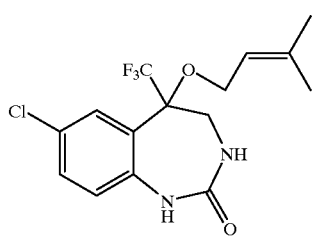

The title compound ($^{19}$F NMR: δ –75.638 ppm) is prepared according to the method of Example 42 by substituting 3-methyl-2-buten-1-ol for cyclobutylmethanol.

Example 44

Preparation of 7-chloro-5-(phenylmethyloxy)-1,5-dihydro-5-(trifluoromethyl)-1,3-benzodiazepin-2-one

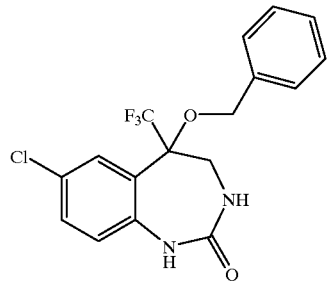

The title compound (mp 177–178° C.) is prepared according to the method of Example 42 by substituting benzyl alcohol for cyclobutylmethanol.

Example 45

Preparation of 7-chloro-5-[(2-pyridyl)methyloxy]-1,5-dihydro-5-(trifluoromethyl)-1,3-benzodiazepin-2-one

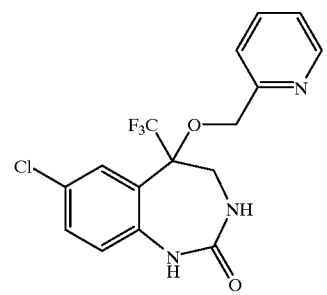

The title compound (mp 233–235° C.) is prepared according to the method of Example 42 by substituting pyridine-2-methanol for cyclobutylmethanol.

Example 46

Preparation of 7-chloro-5-[(1-methylcyclopropyl)methyoxy]-1,5-dihydro-5-(trifluoromethyl)-1,3-benzodiazepin-2-one

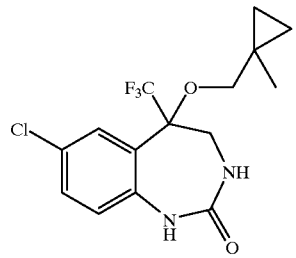

The title compound (mp 211–212° C.) is prepared according to the method of Example 42 by substituting (1-methylcyclopropy)methanol for cyclobutylmethanol.

Example 47

Preparation of 7-chloro-5-(3-methylphenyloxy)-1,5-dihydro-5-(trifluoromethyl)-1,3-benzodiazepin-2-one

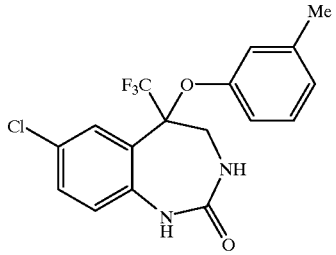

To a solution of m-cresol (0.259 mL) in 5 mL of dry THF at room temperature was added sodium hydride (41 mg). After 10 min, chloride 224 (300 mg) in THF (3.5 mL) was added and the reaction mixture was stirred at ambient temperature for 1 h. The reaction was poured onto saturated ammonium chloride and was extracted with ethyl acetate. The extracts dried over magnesium sulfate and evaporated to give a white solid.

A solution of this material in 3 mL of trifluoroacetic acid was stirred at room temperature for 2 h and then partitioned between ethyl acetate and aqueous sodium bicarbonate. The organic phase was dried and evaporated to a crude product which was purified by flash chromatography on silica gel (35–50% ethyl acetate-hexane). Crystallization from chloroform and recrystallization from 10% ethyl acetate hexane afforded the title compound (25 mg, mp 137.1–140° C.) as colorless crystals.

Example 48

Preparation of 7-chloro-5-(cyclopropylmethylthio)-1,5-dihydro-5-(trifluoromethyl)-1,3-benzodiazepin-2-one

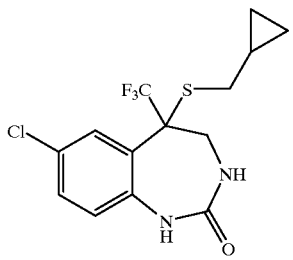

To a solution of cyclopropylmethyl mercaptan (532 mg) in 2.3 mL of dry THF at room temperature was added sodium hydride (41 mg). After 10 min, chloride 224 (200 mg) was added and the reaction mixture was stirred at ambient temperature for 1.5 h. The reaction was poured onto saturated ammonium chloride and was extracted with ethyl acetate. The extracts dried over magnesium sulfate and evaporated to give a white solid.

A solution of this material in 3 mL of trifluoroacetic acid was stirred at room temperature for 2 h and then partitioned between ethyl acetate and aqueous sodium bicarbonate. The organic phase was dried and evaporated to a solid product which was twice from methylene chloride-hexane to afford the title compound (mp 175–177° C.) as a colorless solid.

Example 49

Preparation of 7-chloro-5-(propylthio)-1,5-dihydro-5-(trifluoromethyl)-1,3-benzodiazepin-2-one

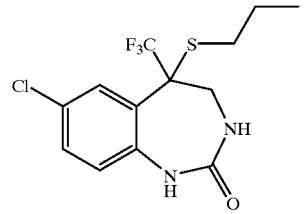

The title compound (mp 156–157° C.) is prepared according to the method of Example 48 by substituting propanethiol for cyclopropylmethyl mercaptan.

Example 50

Preparation of 7-chloro-5-(2-propenylthio)-1,5-dihydro-5-(trifluoromethyl)-1,3-benzodiazepin-2-one

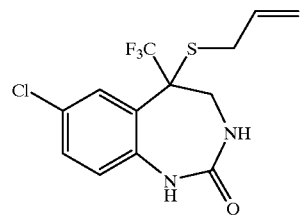

The title compound (mp 147.3–149° C.) is prepared according to the method of Example 48 by substituting allyl mercaptan for cyclopropylmethyl mercaptan.

TABLE 1*

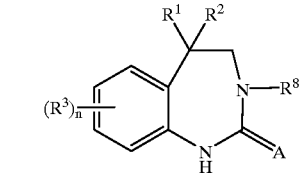

| Ex. # | $R^3$ | $R^1$ | $R^2$ | A | $R^8$ | m.p. (° C.) |
|---|---|---|---|---|---|---|
| 1 | 7-Cl | $CF_3$ | C≡C-cycPr | O | H | 240–242 |
| 2 | 6,7-diF | $CF_3$ | C≡C-cycPr | O | H | 232–233 |
| 3 | 7-Cl | $CF_3$ | C≡C-cycPr | O | H | 221–223 |
| 4 | 7-Cl | $CF_3$ | C≡C-cycPr | S | H | 230 dec. |
| 5 | 7-Cl | $CF_3$ | n-Bu | O | H | 174–176 |
| 6 | 7-Cl | $CF_3$ | C≡C-cycPr | O | $CH_3$ | 177–178 |
| 7 | 7-Cl | $CF_3$ | C≡C-cycPr | O | Et | 186–188 |
| 8 | 7-Cl | $CF_3$ | C≡C-cycPr | O | CyPr | 195–196 |
| 9 | 7-Cl | $CF_3$ | C≡C-cycPr | O | Et | 192–193 |
| 10 | 7-Cl | $CF_3$ | C≡C-cycPr | O | CyPr | 181–182 |
| 11 | 7-Cl | $CF_3$ | $OCH_2$-cycPr | O | $CH_3$ | 163–165 |
| 12 | 7-Cl | $CF_3$ | $OCH_2$—C═C(Cl)$_2$ | O | $CH_3$ | 148.6–149.9 |
| 13 | 7-Cl | $CF_3$ | $OCH_2$—C≡$CH_3$ | O | $CH_3$ | 229.7–232.1 |
| 14 | 7-Cl | $CF_3$ | $OCH_2$-(2-F-6-$CH_3$O-phenyl) | O | $CH_3$ | 172.1–173.8 |
| 15 | 7-Cl | $CF_3$ | $OCH_2$-cycPr | O | H | 185–186 |
| 16(s) | 7-Cl | $CF_3$ | $OCH_2$-cycPr | O | H | 190–191 |

TABLE 1*-continued

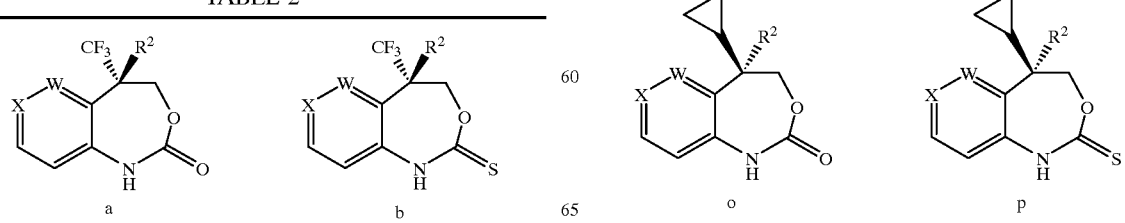

| Ex. # | R³ | R¹ | R² | A | R⁸ | m.p. (° C.) |
|---|---|---|---|---|---|---|
| 17 | 7-Cl | CF₃ | OCH₂-cycPr | O | CyPr | 153.5–155 |
| 18(s) | 7-Cl | CF₃ | OCH₂-cycPr | O | CyPr | 66–68 |
| 19 | 7-Cl | CF₃ | OCH₂CH₂CH₃ | O | CyPr | 153–154 |
| 20 | 7-Cl | CF₃ | SCH₂CH₂CH₃ | O | CyPr | 150–151 |
| 21 | 7-Cl | CF₃ | SCH₂C=CH₂ | O | CyPr | 144–145.5 |
| 22 | 7-Cl | CF₃ | OCH₂C=CH₂ | O | CyPr | 120–121 |
| 23 | 7-Cl | CF₃ | OCH₂C=C(CH₃)₂ | O | CyPr | 130–131 |
| 24 | 7-Cl | CF₃ | OCH₂cycBu | O | CyPr | 158–159 |
| 25 | 7-Cl | CF₃ | OCH₂-(1-CH₃-cycPr) | O | CyPr | 166–167 |
| 26 | 7-Cl | CF₃ | OCH₂-pyrid-2-yl | O | CyPr | 170–171.5 |
| 27 | 7-Cl | CF₃ | OCH₂-cycPr | O | i-Pr | 169.5–170.5 |
| 28 | 7-Cl | CF₃ | OCH₂-cycPr | O | CyBu | 156 |
| 29 | 7-Cl | CF₃ | OCH₂-cycPr | O | Et | 157–159 |
| 30(s) | 7-Cl | CF₃ | OCH₂-cycPr | O | Et | |
| 31 | 7-Cl | CF₃ | OCH₂C=C(CH₃)₂ | O | Et | 158–160 |
| 32 | 7-Cl | CF₃ | SCH₂C=CH₂ | O | Et | 138.1–141.8 |
| 33 | 7-Cl | CF₃ | OCH₂cycBu | O | Et | |
| 34 | 7-Cl | CF₃ | SCH₂-cycPr | O | Et | 152.3–156 |
| 35 | 7-Cl | CF₃ | OCH₂-(1-CH₃-cycPr) | O | Et | 171–172.5 |
| 36 | 7-Cl | CF₃ | OCH₂-cycPr | O | n-Pr | 155.5–157.5 |
| 37 | 7-F | CF₃ | OCH₂-cycPr | O | H | 198–199 |
| 38 | 7-F | CF₃ | OCH₂-cycPr | O | Et | 156 |
| 39 | 7-F | CF₃ | OCH₂-cycBu | O | H | 190–191 |
| 40 | 7-F | CF₃ | OCH₂-cycBu | O | Et | 137–138 |
| 41 | 7-Cl | CF₃ | C≡C-(1-CH₃-cycPr) | O | H | 196–198 |
| 42 | 7-Cl | CF₃ | OCH₂cycBu | O | H | 201.6–202.9 |
| 43 | 7-Cl | CF₃ | OCH₂C=C(CH₃)₂ | O | H | |
| 44 | 7-Cl | CF₃ | OCH₂-phenyl | O | H | 177–178 |
| 45 | 7-Cl | CF₃ | OCH₂-pyrid-2-yl | O | H | 233–235 |
| 46 | 7-Cl | CF₃ | OCH₂-(1-CH₃-cycPr) | O | H | 211–212 |
| 47 | 7-Cl | CF₃ | O-(3-CH₃-phenyl) | O | H | 137.1–140 |
| 48 | 7-Cl | CF₃ | SCH₂-cycPr | O | H | 175–177 |
| 49 | 7-Cl | CF₃ | SCH₂CH₂CH₃ | O | H | 156–157 |
| 50 | 7-Cl | CF₃ | SCH₂C=CH₂ | O | H | 147.3–149 |

*Unless otherwise indicated, stereochemisty is (+/−).

TABLE 2*

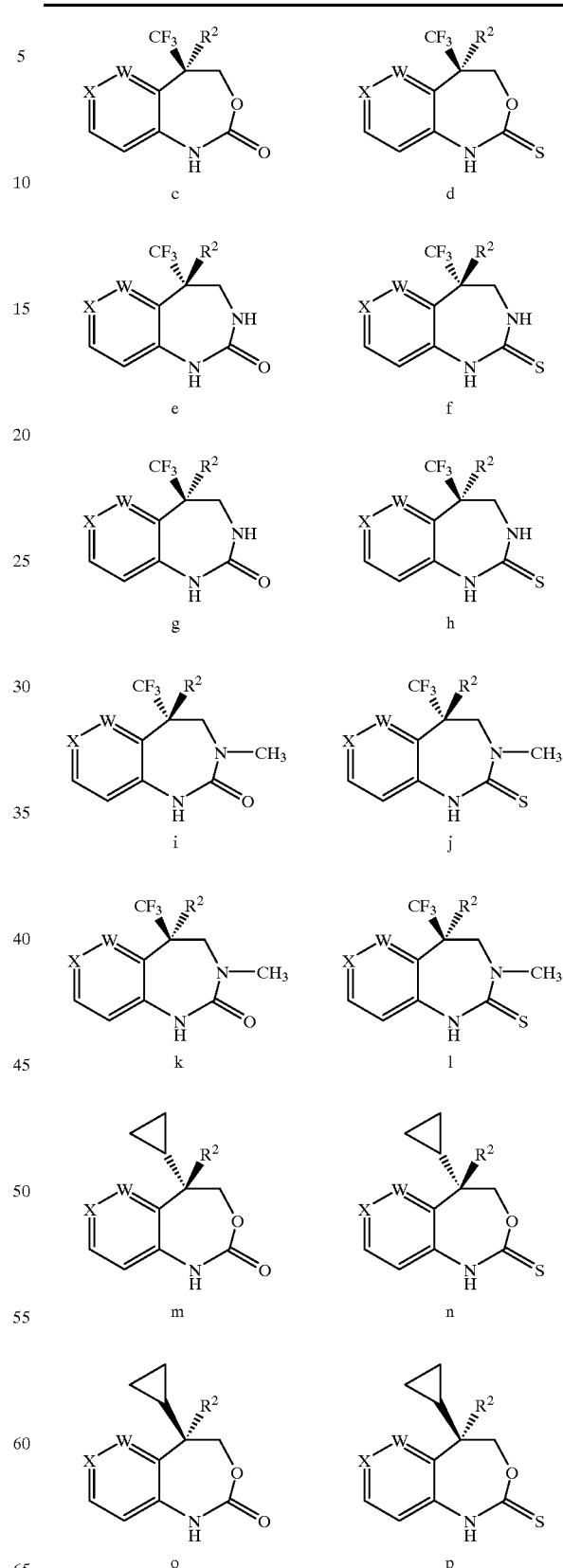

TABLE 2*-continued
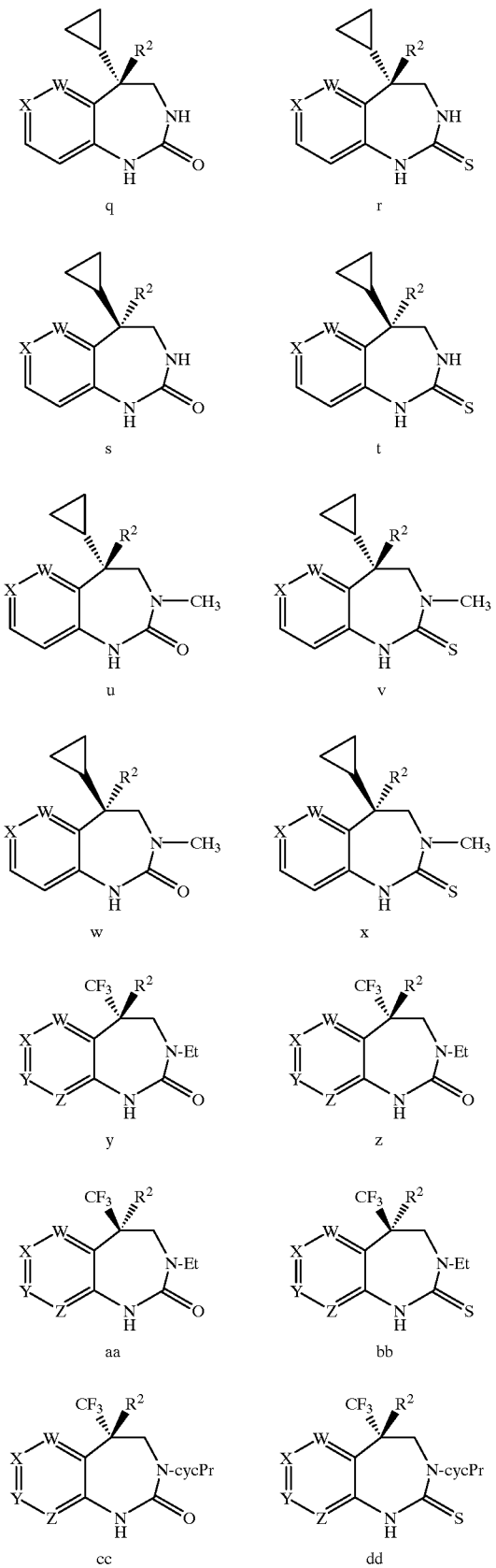
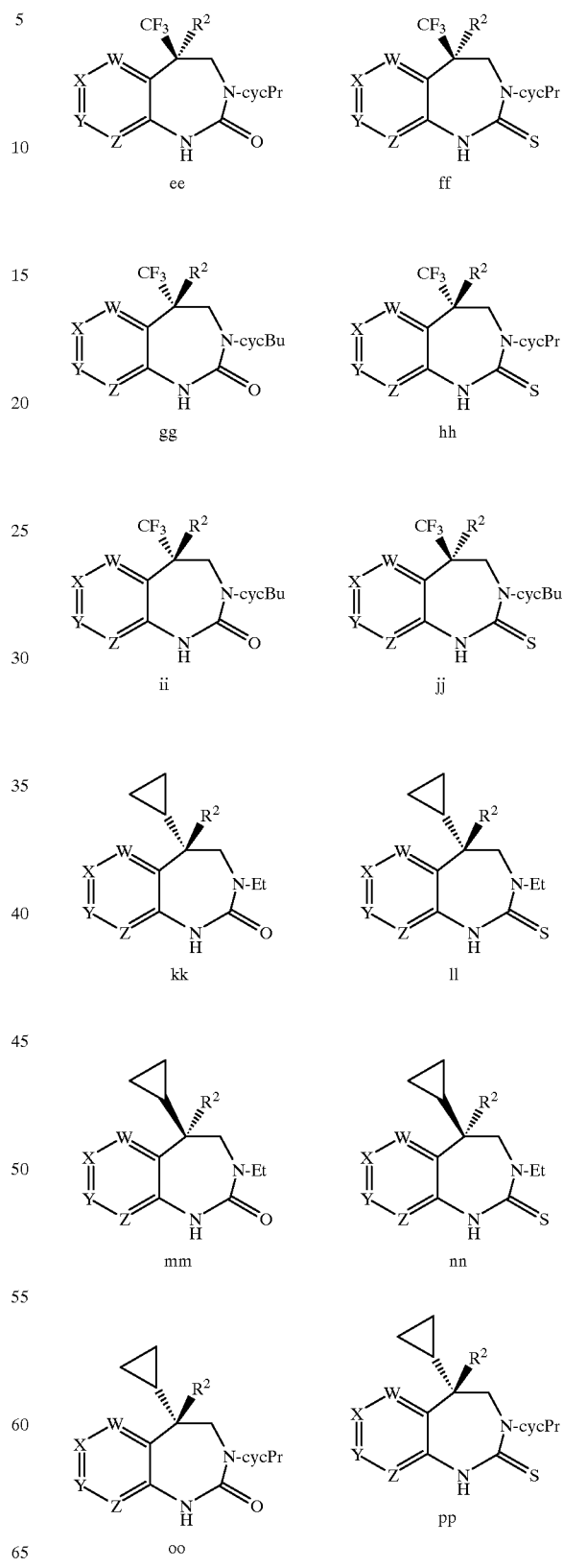

TABLE 2*-continued

Structures qq, rr, ss, tt, uu, vv (cyclopropyl-substituted bicyclic diazepine cores with variations: qq = N-cycPr, O; rr = N-cycPr, S; ss = N-cycBu, O; tt = N-cycBu, S; uu = N-cycBu, O; vv = N-cycBu, S)

| Ex. # | W | X | R² |
|---|---|---|---|
| 1. | CH | CH | C≡C-cycPr |
| 2. | CH | CH | C≡C-(1-CH₃-cycPr) |
| 3. | CH | CH | C≡C—iPr |
| 4. | CH | CH | C≡C—nPr |
| 5. | CH | CH | C≡C—Bu |
| 6. | CH | CH | C≡C—iBu |
| 7. | CH | CH | C≡C—tBu |
| 8. | CH | CH | C≡C—Et |
| 9. | CH | CH | C≡C—Me |
| 10. | CH | CH | C≡C—Ph |
| 11. | CH | CH | C≡C-2-Pyridyl |
| 12. | CH | CH | C≡C-3-Pyridyl |
| 13. | CH | CH | C≡C-4-Pyridyl |
| 14. | CH | CH | C≡C-2-furanyl |
| 15. | CH | CH | C≡C-3-furanyl |
| 16. | CH | CH | C≡C-2-thienyl |
| 17. | CH | CH | C≡C-3-thienyl |
| 18. | CH | CH | CH=CH-cycPr |
| 19. | CH | CH | CH=CH—iPr |
| 20. | CH | CH | CH=CH—nPr |
| 21. | CH | CH | CH=CH—Bu |
| 22. | CH | CH | CH=CH—iBu |
| 23. | CH | CH | CH=CH—tBu |
| 24. | CH | CH | CH=CH—Et |
| 25. | CH | CH | CH=CH—Me |
| 26. | CH | CH | CH=CH—Ph |
| 27. | CH | CH | CH=CH-2-Pyridyl |
| 28. | CH | CH | CH=CH-3-Pyridyl |
| 29. | CH | CH | CH=CH-4-Pyridyl |
| 30. | CH | CH | CH=CH-2-furanyl |
| 31. | CH | CH | CH=CH-3-furanyl |
| 32. | CH | CH | CH=CH-2-thienyl |
| 33. | CH | CH | CH=CH-3-thienyl |
| 34. | CH | CH | CH₂CH₂CH₂CH₂CH₃ |
| 35. | CH | CH | CH₂CH₂CH(CH₃)₂ |
| 36. | CH | CH | CH₂CH₂CH₂CH₃ |
| 37. | CH | CH | CH₂CH₂CH₃ |
| 38. | CH | CH | CH₂CH₂-cycPr |
| 39. | CH | CH | CH₂CH₂-(1-CH₃-cycPr) |
| 40. | CH | CH | CH₂CH₂-tBu |
| 41. | CH | CH | CH₂CH₂-cycBu |
| 42. | CH | CH | CH₂CH₂-(1-CH₃-cycBu) |
| 43. | CH | CH | CH₂CH₂-2-Pyridyl |
| 44. | CH | CH | CH₂CH₂-3-Pyridyl |
| 45. | CH | CH | CH₂CH₂-4-Pyridyl |
| 46. | CH | CH | CH₂CH₂-2-furanyl |
| 47. | CH | CH | CH₂CH₂-3-furanyl |
| 48. | CH | CH | CH₂CH₂-2-thienyl |
| 49. | CH | CH | CH₂CH₂-3-thienyl |
| 50. | CH | CH | CH₂C≡C-cycPr |
| 51. | CH | CH | CH₂C≡C-2-furanyl |
| 52. | CH | CH | CH₂CH=CH-cycPr |
| 53. | CH | CH | CH₂CH=CH-2-furanyl |
| 54. | CH | CH | CH=CHCH₂-cycPr |
| 55. | CH | CH | CH=CHCH₂-2-furanyl |
| 56. | CH | CH | OCH₂C=C(CH₃)₂ |
| 57. | CH | CH | E-OCH₂C=CHCH₃ |
| 58. | CH | CH | Z-OCH₂C=CHCH₃ |
| 59. | CH | CH | OCH₂CH₃ |
| 60. | CH | CH | OCH₂CH₂CH₃ |
| 61. | CH | CH | OCH₂C=C(Cl)₂ |
| 62. | CH | CH | OCH₂C=CH₂ |
| 63. | CH | CH | OCH₂C≡CCH₃ |
| 64. | CH | CH | OCH₂CH₂CH₃ |
| 65. | CH | CH | OCH₂-cycPr |
| 66. | CH | CH | OCH₂-(1-CH₃-cycPr) |
| 67. | CH | CH | OCH₂-cycBu |
| 68. | CH | CH | OCH₂-(1-CH₃-cycBu) |
| 69. | CH | CH | OCH₂-Phenyl |
| 70. | CH | CH | OCH₂CH₂-cycPr |
| 71. | CH | CH | OCH₂CH=cycPr |
| 72. | CCl | CH | C≡C-cycPr |
| 73. | CCl | CH | C≡C-(1-CH₃-cycPr) |
| 74. | CCl | CH | C≡C—iPr |
| 75. | CCl | CH | C≡C—nPr |
| 76. | CCl | CH | C≡C—Bu |
| 77. | CCl | CH | C≡C—iBu |
| 78. | CCl | CH | C≡C—tBu |
| 79. | CCl | CH | C≡C—Et |
| 80. | CCl | CH | C≡C—Me |
| 81. | CCl | CH | C≡C—Ph |
| 82. | CCl | CH | C≡-C-2-Pyridyl |
| 83. | CCl | CH | C≡C-3-Pyridyl |
| 84. | CCl | CH | C≡C-4-Pyridyl |
| 85. | CCl | CH | C≡-C-2-furanyl |
| 86. | CCl | CH | C≡C-3-furanyl |
| 87. | CCl | CH | C≡C-2-thienyl |
| 88. | CCl | CH | C≡C-3-thienyl |
| 89. | CCl | CH | CH=CH-cycPr |
| 90. | CCl | CH | CH=CH-iPr |
| 91. | CCl | CH | CH=CH-nPr |
| 92. | CCl | CH | CH=CH-Bu |
| 93. | CCl | CH | CH=CH-iBu |
| 94. | CCl | CH | CH=CH-tBu |
| 95. | CCl | CH | CH=CH-Et |
| 96. | CCl | CH | CH=CH-Me |
| 97. | CCl | CH | CH=CH-Ph |
| 98. | CCl | CH | CH=CH-2-Pyridyl |
| 99. | CCl | CH | CH=CH-3-Pyridyl |
| 100. | CCl | CH | CH=CH-4-Pyridyl |
| 101. | CCl | CH | CH=CH-2-furanyl |
| 102. | CCl | CH | CH=CH-3-furanyl |
| 103. | CCl | CH | CH=CH-2-thienyl |
| 104. | CCl | CH | CH=CH-3-thienyl |
| 105. | CCl | CH | CH₂CH₂CH₂CH₂CH₃ |
| 106. | CCl | CH | CH₂CH₂CH(CH₃)₂ |
| 107. | CCl | CH | CH₂CH₂CH₂CH₃ |
| 108. | CCl | CH | CH₂CH₂CH₃ |
| 109. | CCl | CH | CH₂CH₂-cycPr |
| 110. | CCl | CH | CH₂CH₂-(1-CH₃-cycPr) |
| 111. | CCl | CH | CH₂CH₂-tBu |
| 112. | CCl | CH | CH₂CH₂-cycBu |
| 113. | CCl | CH | CH₂CH₂-(1-CH₃-cycBu) |
| 114. | CCl | CH | CH₂CH₂-2-Pyridyl |
| 115. | CCl | CH | CH₂CH₂-3-Pyridyl |
| 116. | CCl | CH | CH₂CH₂-4-Pyridyl |
| 117. | CCl | CH | CH₂CH₂-2-furanyl |
| 118. | CCl | CH | CH₂CH₂-3-furanyl |
| 119. | CCl | CH | CH₂CH₂-2-thienyl |

TABLE 2*-continued

| | | | |
|---|---|---|---|
| 120. | CCl | CH | CH$_2$CH$_2$-3-thienyl |
| 121. | CCl | CH | CH$_2$C≡C-cycPr |
| 122. | CCl | CH | CH$_2$C≡C-2-furanyl |
| 123. | CCl | CH | CH$_2$CH=CH-cycPr |
| 124. | CCl | CH | CH$_2$CH=CH-2-furanyl |
| 125. | CCl | CH | CH=CHCH$_2$-cycPr |
| 126. | CCl | CH | CH=CHCH$_2$-2-furanyl |
| 127. | CCl | CH | OCH$_2$C=C(CH$_3$)$_2$ |
| 128. | CCl | CH | E-OCH$_2$C=CHCH$_3$ |
| 129. | CCl | CH | Z-OCH$_2$C=CHCH$_3$ |
| 130. | CCl | CH | OCH$_2$CH$_3$ |
| 131. | CCl | CH | OCH$_2$CH$_2$CH$_3$ |
| 132. | CCl | CH | OCH$_2$C=C(Cl)$_2$ |
| 133. | CCl | CH | OCH$_2$C=CH$_2$ |
| 134. | CCl | CH | OCH$_2$C≡CCH$_3$ |
| 135. | CCl | CH | OCH$_2$CH$_2$CH$_3$ |
| 136. | CCl | CH | OCH$_2$-cycPr |
| 137. | CCl | CH | OCH$_2$-(1-CH$_3$-cycPr) |
| 138. | CCl | CH | OCH$_2$-cycBu |
| 139. | CCl | CH | OCH$_2$-(1-CH$_3$-cycBu) |
| 140. | CCl | CH | OCH$_2$-Phenyl |
| 141. | CCl | CH | OCH$_2$CH$_2$-cycPr |
| 142. | CCl | CH | OCH$_2$CH=cycPr |
| 143. | CH | CCl | C≡C-cycPr |
| 144. | CH | CCl | C≡C-(1-CH$_3$-cycPr) |
| 145. | CH | CCl | C≡C-iPr |
| 146. | CH | CCl | C≡C-nPr |
| 147. | CH | CCl | C≡C-Bu |
| 148. | CH | CCl | C≡C-iBu |
| 149. | CH | CCl | C≡C-tBu |
| 150. | CH | CCl | C≡C-Et |
| 151. | CH | CCl | C≡C-Me |
| 152. | CH | CCl | C≡C-Ph |
| 153. | CH | CCl | C≡C-2-Pyridyl |
| 154. | CH | CCl | C≡C-3-Pyridyl |
| 155. | CH | CCl | C≡C-4-Pyridyl |
| 156. | CH | CCl | C≡C-2-furanyl |
| 157. | CH | CCl | C≡C-3-furanyl |
| 158. | CH | CCl | C≡C-2-thienyl |
| 159. | CH | CCl | C≡C-3-thienyl |
| 160. | CH | CCl | CH=CH-cycPr |
| 161. | CH | CCl | CH=CH-iPr |
| 162. | CH | CCl | CH=CH-nPr |
| 163. | CH | CCl | CH=CH-Bu |
| 164. | CH | CCl | CH=CH-iBu |
| 165. | CH | CCl | CH=CH-tBu |
| 166. | CH | CCl | CH=CH-Et |
| 167. | CH | CCl | CH=CH-Me |
| 168. | CH | CCl | CH=CH-Ph |
| 169. | CH | CCl | CH=CH-2-Pyridyl |
| 170. | CH | CCl | CH=CH-3-Pyridyl |
| 171. | CH | CCl | CH=CH-4-Pyridyl |
| 172. | CH | CCl | CH=CH-2-furanyl |
| 173. | CH | CCl | CH=CH-3-furanyl |
| 174. | CH | CCl | CH=CH-2-thienyl |
| 175. | CH | CCl | CH=CH-3-thienyl |
| 176. | CH | CCl | CH$_2$CH$_2$CH$_2$CH$_2$CH$_3$ |
| 177. | CH | CCl | CH$_2$CH$_2$CH(CH$_3$)$_2$ |
| 178. | CH | CCl | CH$_2$CH$_2$CH$_2$CH$_3$ |
| 179. | CH | CCl | CH$_2$CH$_2$CH$_3$ |
| 180. | CH | CCl | CH$_2$CH$_2$-cycPr |
| 181. | CH | CCl | CH$_2$CH$_2$-(1-CH$_3$-cycPr) |
| 182. | CH | CCl | CH$_2$CH$_2$-tBu |
| 183. | CH | CCl | CH$_2$CH$_2$-cycBu |
| 184. | CH | CCl | CH$_2$CH$_2$-(1-CH$_3$-cycBu) |
| 185. | CH | CCl | CH$_2$CH$_2$-2-Pyridyl |
| 186. | CH | CCl | CH$_2$CH$_2$-3-Pyridyl |
| 187. | CH | CCl | CH$_2$CH$_2$-4-Pyridyl |
| 188. | CH | CCl | CH$_2$CH$_2$-2-furanyl |
| 189. | CH | CCl | CH$_2$CH$_2$-3-furanyl |
| 190. | CH | CCl | CH$_2$CH$_2$-2-thienyl |
| 191. | CH | CCl | CH$_2$CH$_2$-3-thienyl |
| 192. | CH | CCl | CH$_2$C≡C-cycPr |
| 193. | CH | CCl | CH$_2$C≡C-2-furanyl |
| 194. | CH | CCl | CH$_2$CH=CH-cycPr |
| 195. | CH | CCl | CH$_2$CH=CH-2-furanyl |
| 196. | CH | CCl | CH=CHCH$_2$-cycPr |
| 197. | CH | CCl | CH=CHCH$_2$-2-furanyl |
| 198. | CH | CCl | OCH$_2$C=C(CH$_3$)$_2$ |
| 199. | CH | CCl | E-OCH$_2$C=CHCH$_3$ |
| 200. | CH | CCl | Z-OCH$_2$C=CHCH$_3$ |
| 201. | CH | CCl | OCH$_2$CH$_3$ |
| 202. | CH | CCl | OCH$_2$CH$_2$CH$_3$ |
| 203. | CH | CCl | OCH$_2$C=C(Cl)$_2$ |
| 204. | CH | CCl | OCH$_2$C=CH$_2$ |
| 205. | CH | CCl | OCH$_2$C≡CCH$_3$ |
| 206. | CH | CCl | OCH$_2$CH$_2$CH$_3$ |
| 207. | CH | CCl | OCH$_2$-cycPr |
| 208. | CH | CCl | OCH$_2$-(1-CH$_3$-cycPr) |
| 209. | CH | CCl | OCH$_2$-cycBu |
| 210. | CH | CCl | OCH$_2$-(1-CH$_3$-cycBu) |
| 211. | CH | CCl | OCH$_2$-Phenyl |
| 212. | CH | CCl | OCH$_2$CH$_2$-cycPr |
| 213. | CH | CCl | OCH$_2$CH=cycPr |
| 214. | CCl | CCl | C≡C-cycPr |
| 215. | CCl | CCl | C≡C-(1-CH$_3$-cycPr) |
| 216. | CCl | CCl | C≡C-iPr |
| 217. | CCl | CCl | C≡C-nPr |
| 218. | CCl | CCl | C≡C-Bu |
| 219. | CCl | CCl | C≡C-iBu |
| 220. | CCl | CCl | C≡C-tBu |
| 221. | CCl | CCl | C≡C-Et |
| 222. | CCl | CCl | C≡C-Me |
| 223. | CCl | CCl | C≡C-Ph |
| 224. | CCl | CCl | C≡C-2-Pyridyl |
| 225. | CCl | CCl | C≡C-3-Pyridyl |
| 226. | CCl | CCl | C≡C-4-Pyridyl |
| 227. | CCl | CCl | C≡C-2-furanyl |
| 228. | CCl | CCl | C≡C-3-furanyl |
| 229. | CCl | CCl | C≡C-2-thienyl |
| 230. | CCl | CCl | C≡C-3-thienyl |
| 231. | CCl | CCl | CH=CH-cycPr |
| 232. | CCl | CCl | CH=CH-iPr |
| 233. | CCl | CCl | CH=CH-nPr |
| 234. | CCl | CCl | CH=CH-Bu |
| 235. | CCl | CCl | CH=CH-iBu |
| 236. | CCl | CCl | CH=CH-tBu |
| 237. | CCl | CCX | CH=CH-Et |
| 238. | CCl | CCl | CH=CH-Me |
| 239. | CCl | CCl | CH=CH-Ph |
| 240. | CCl | CCl | CH=CH-2-Pyridyl |
| 241. | CCl | CCl | CH=CH-3-Pyridyl |
| 242. | CCl | CCl | CH=CH-4-Pyridyl |
| 243. | CCl | CCl | CH=CH-2-furanyl |
| 244. | CCl | CCl | CH=CH-3-furanyl |
| 245. | CCl | CCl | CH=CH-2-thienyl |
| 246. | CCl | CCl | CH=CH-3-thienyl |
| 247. | CCl | CCl | CH$_2$CH$_2$CH$_2$CH$_2$CH$_3$ |
| 248. | CCl | CCl | CH$_2$CH$_2$CH(CH$_3$)$_2$ |
| 249. | CCl | CCl | CH$_2$CH$_2$CH$_2$CH$_3$ |
| 250. | CCl | CCl | CH$_2$CH$_2$CH$_3$ |
| 251. | CCl | CCl | CH$_2$CH$_2$-cycPr |
| 252. | CCl | CCl | CH$_2$CH$_2$-(1-CH$_3$-cycPr) |
| 253. | CCl | CCl | CH$_2$CH$_2$-tBu |
| 254. | CCl | CCl | CH$_2$CH$_2$-cycBu |
| 255. | CCl | CCl | CH$_2$CH$_2$-(1-CH$_3$-cycBu) |
| 256. | CCl | CCl | CH$_2$CH$_2$-2-Pyridyl |
| 257. | CCl | CCl | CH$_2$CH$_2$-3-Pyridyl |
| 258. | CCl | CCl | CH$_2$CH$_2$-4-Pyridyl |
| 259. | CCl | CCl | CH$_2$CH$_2$-2-furanyl |
| 260. | CCl | CCl | CH$_2$CH$_2$-3-furanyl |
| 261. | CCl | CCl | CH$_2$CH$_2$-2-thienyl |
| 262. | CCl | CCl | CH$_2$CH$_2$-3-thienyl |
| 263. | CCl | CCl | CH$_2$C≡C-cycPr |
| 264. | CCl | CCl | CH$_2$C≡C-2-furanyl |
| 265. | CCl | CCl | CH$_2$CH=CH-cycPr |
| 266. | CCi | CCl | CH$_2$CH=CH-2-furanyl |
| 267. | CCl | CCl | CH=CHCH$_2$-cycPr |
| 268. | CCl | CCl | CH=CHCH$_2$-2-furanyl |
| 269. | CCl | CCl | OCH$_2$C=C(CH$_3$)$_2$ |
| 270. | CCl | CCl | E-OCH$_2$C=CHCH$_3$ |
| 271. | CCl | CCl | Z-OCH$_2$C=CHCH$_3$ |
| 272. | CCl | CCl | OCH$_2$CH$_3$ |
| 273. | CCl | CCl | OCH$_2$CH$_2$CH$_3$ |
| 274. | CCl | CCl | OCH$_2$C=C(Cl)$_2$ |
| 275. | CCl | CCl | OCH$_2$C=CH$_2$ |
| 276. | CCl | CCl | OCH$_2$C≡CCH$_3$ |
| 277. | CCl | CCl | OCH$_2$CH$_2$CH$_3$ |

TABLE 2*-continued

| | | | |
|---|---|---|---|
| 278. | CCl | CCl | OCH$_2$-cycPr |
| 279. | CCl | CCl | OCH$_2$-(1-CH$_3$-cycPr) |
| 280. | CCl | CCl | OCH$_2$-cycBu |
| 281. | CCl | CCl | OCH$_2$-(1-CH$_3$-cycBu) |
| 282. | CCl | CCl | OCH$_2$-Phenyl |
| 283. | CCl | CCl | OCH$_2$CH$_2$-cycPr |
| 284. | CCl | CCl | OCH$_2$CH=cycPr |
| 285. | CF | CH | C≡C-cycPr |
| 286. | CF | CH | C≡C-(1-CH$_3$-cycPr) |
| 287. | CF | CH | C≡C-iPr |
| 288. | CF | CH | C≡C-nPr |
| 289. | CF | CH | C≡C-Bu |
| 290. | CF | CH | C≡C-iBu |
| 291. | CF | CH | C≡C-tBu |
| 292. | CF | CH | C≡C-Et |
| 293. | CF | CH | C≡C-Me |
| 294. | CF | CH | C≡C-Ph |
| 295. | CF | CH | C≡C-2-Pyridyl |
| 296. | CF | CH | C≡C-3-Pyridyl |
| 297. | CF | CH | C≡C-4-Pyridyl |
| 298. | CF | CH | C≡C-2-furanyl |
| 299. | CF | CH | C≡C-3-furanyl |
| 300. | CF | CH | C≡C-2-thienyl |
| 301. | CF | CH | C≡C-3-thienyl |
| 302. | CF | CH | CH=CH-cycPr |
| 303. | CF | CH | CH=CH-iPr |
| 304. | CF | CH | CH=CH-nPr |
| 305. | CF | CH | CH=CH-Bu |
| 306. | CF | CH | CH=CH-iBu |
| 307. | CF | CH | CH=CH-tBu |
| 308. | CF | CH | CH=CH-Et |
| 309. | CF | CH | CH=CH-Me |
| 310. | CF | CH | CH=CH-Ph |
| 311. | CF | CH | CH=CH-2-Pyridyl |
| 312. | CF | CH | CH=CH-3-Pyridyl |
| 313. | CF | CH | C≡C-4-Pyridyl |
| 314. | CF | CH | C≡C-2-furanyl |
| 315. | CF | CH | C≡C-3-furanyl |
| 316. | CF | CH | C≡C-2-thienyl |
| 317. | CF | CH | C≡C-3-thienyl |
| 318. | CF | CH | CH$_2$CH$_2$CH$_2$CH$_2$CH$_3$ |
| 319. | CF | CH | CH$_2$CH$_2$CH(CH$_3$)$_2$ |
| 320. | CF | CH | CH$_2$CH$_2$CH$_2$CH$_3$ |
| 321. | CF | CH | CH$_2$CH$_2$CH$_3$ |
| 322. | CF | CH | CH$_2$CH$_2$-cycPr |
| 323. | CF | CH | CH$_2$CH$_2$-(1-CH$_3$-cycPr) |
| 324. | CF | CH | CH$_2$CH$_2$-tBu |
| 325. | CF | CH | CH$_2$CH$_2$-cycBu |
| 326. | CF | CH | CH$_2$CH$_2$-(1-CH$_3$-cycBu) |
| 327. | CF | CH | CH$_2$CH$_2$-2-Pyridyl |
| 328. | CF | CH | CH$_2$CH$_2$-3-Pyridyl |
| 329. | CF | CH | CH$_2$CH$_2$-4-Pyridyl |
| 330. | CF | CH | CH$_2$CH$_2$-2-furanyl |
| 331. | CF | CH | CH$_2$CH$_2$-3-furanyl |
| 332. | CF | CH | CH$_2$CH$_2$-2-thienyl |
| 333. | CF | CH | CH$_2$CH$_2$-3-thienyl |
| 334. | CF | CH | CH$_2$C≡C-cycPr |
| 335. | CF | CH | CH$_2$C≡C-2-furanyl |
| 336. | CF | CH | CH$_2$CH=CH-cycPr |
| 337. | CF | CH | CH$_2$CH=CH-2-furanyl |
| 338. | CF | CH | CH=CHCH$_2$-cycPr |
| 339. | CF | CH | CH=CHCH$_2$-2-furanyl |
| 340. | CF | CH | OCH$_2$C=C(CH$_3$)$_2$ |
| 341. | CF | CH | E-OCH$_2$C=CHCH$_3$ |
| 342. | CF | CH | Z-OCH$_2$C=CHCH$_3$ |
| 343. | CF | CH | OCH$_2$CH$_3$ |
| 344. | CF | CH | OCH$_2$CH$_2$CH$_3$ |
| 345. | CF | CH | OCH$_2$C=C(Cl)$_2$ |
| 346. | CF | CH | OCH$_2$C=CH$_2$ |
| 347. | CF | CH | OCH$_2$C≡CCH$_3$ |
| 348. | CF | CH | OCH$_2$CH$_2$CH$_3$ |
| 349. | CF | CH | OCH$_2$-cycPr |
| 350. | CF | CH | OCH$_2$-(1-CH$_3$-cycPr) |
| 351. | CF | CH | OCH$_2$-cycBu |
| 352. | CF | CH | OCH$_2$-(1-CH$_3$-cycBu) |
| 353. | CF | CH | OCH$_2$-Phenyl |
| 354. | CF | CH | OCH$_2$CH$_2$-cycPr |
| 355. | CF | CH | OCH$_2$CH=cycPr |
| 356. | CH | CF | C≡C-cycPr |
| 357. | CH | CF | C≡C-(1-CH$_3$-cycPr) |
| 358. | CH | CF | C≡C-iPr |
| 359. | CH | CF | C≡C-nPr |
| 360. | CH | CF | C≡C-Bu |
| 361. | CH | CF | C≡C-iBu |
| 362. | CH | CF | C≡C-tBu |
| 363. | CH | CF | C≡C-Et |
| 364. | CH | CF | C≡C-Me |
| 365. | CH | CF | C≡C-Ph |
| 366. | CH | CF | C≡C-2-Pyridyl |
| 367. | CH | CF | C≡C-3-Pyridyl |
| 368. | CH | CF | C≡C-4-Pyridyl |
| 369. | CH | CF | C≡C-2-furanyl |
| 370. | CH | CF | C≡C-3-furanyl |
| 371. | CH | CF | C≡C-2-thienyl |
| 372. | CH | CF | C≡C-3-thienyl |
| 373. | CH | CF | CH=CH-cycPr |
| 374. | CH | CF | CH=CH-iPr |
| 375. | CH | CF | CH=CH-nPr |
| 376. | CH | CF | CH=CH-Bu |
| 377. | CH | CF | CH=CH-iBu |
| 378. | CH | CF | CH=CH-tBu |
| 379. | CH | CF | CH=CH-Et |
| 380. | CH | CF | CH=CH-Me |
| 381. | CH | CF | CH=CH-Ph |
| 382. | CH | CF | CH=CH-2-Pyridyl |
| 383. | CH | CF | CH=CH-3-Pyridyl |
| 384. | CH | CF | CH=CH-4-Pyridyl |
| 385. | CH | CF | CH=CH-2-furanyl |
| 386. | CH | CF | CH=CH-3-furanyl |
| 387. | CH | CF | CH=CH-2-thienyl |
| 388. | CH | CF | CH=CH-3-thienyl |
| 389. | CH | CF | CH$_2$CH$_2$CH$_2$CH$_2$CH$_3$ |
| 390. | CH | CF | CH$_2$CH$_2$CH(CH$_3$)$_2$ |
| 391. | CH | CF | CH$_2$CH$_2$CH$_2$CH$_3$ |
| 392. | CH | CF | CH$_2$CH$_2$CH$_3$ |
| 393. | CH | CF | CH$_2$CH$_2$-cycPr |
| 394. | CH | CF | CH$_2$CH$_2$-(1-CH$_3$-cycPr) |
| 395. | CH | CF | CH$_2$CH$_2$-tBu |
| 396. | CH | CF | CH$_2$CH$_2$-cycBu |
| 397. | CH | CF | CH$_2$CH$_2$-(1-CH$_3$-cycBu) |
| 398. | CH | CF | CH$_2$CH$_2$-2-Pyridyl |
| 399. | CH | CF | CH$_2$CH$_2$-3-Pyridyl |
| 400. | CH | CF | CH$_2$CH$_2$-4-Pyridyl |
| 401. | CH | CF | CH$_2$CH$_2$-2-furanyl |
| 402. | CH | CF | CH$_2$CH$_2$-3-furanyl |
| 403. | CH | CF | CH$_2$CH$_2$-2-thienyl |
| 404. | CH | CF | CH$_2$CH$_2$-3-thienyl |
| 405. | CH | CF | CH$_2$C≡C-cycPr |
| 406. | CH | CF | CH$_2$C≡C-2-furanyl |
| 407. | CH | CF | CH$_2$CH=CH-cycPr |
| 408. | CH | CF | CH$_2$CH=CH-2-furanyl |
| 409. | CH | CF | CH=CHCH$_2$-cycPr |
| 410. | CH | CF | CH=CHCH$_2$-2-furanyl |
| 411. | CH | CF | OCH$_2$C=C(CH$_3$)$_2$ |
| 412. | CH | CF | E-OCH$_2$C=CHCH$_3$ |
| 413. | CH | CF | Z-OCH$_2$C=CHCH$_3$ |
| 414. | CH | CF | OCH$_2$CH$_3$ |
| 415. | CH | CF | OCH$_2$CH$_2$CH$_3$ |
| 416. | CH | CF | OCH$_2$C=C(Cl)$_2$ |
| 417. | CH | CF | OCH$_2$C=CH$_2$ |
| 418. | CH | CF | OCH$_2$C≡CCH$_3$ |
| 419. | CH | CF | OCH$_2$CH$_2$CH$_3$ |
| 420. | CH | CF | OCH$_2$-cycPr |
| 421. | CH | CF | OCH$_2$-(1-CH$_3$-cycPr) |
| 422. | CH | CF | OCH$_2$-cycBu |
| 423. | CH | CF | OCH$_2$-(1-CH$_3$-cycBu) |
| 424. | CH | CF | OCH$_2$-Phenyl |
| 425. | CH | CF | OCH$_2$CH$_2$-cycPr |
| 426. | CH | CF | OCH$_2$CH=cycPr |
| 427. | CF | CF | C≡C-cycPr |
| 428. | CF | CF | C≡C-(1-CH$_3$-cycPr) |
| 429. | CF | CF | C≡C-iPr |
| 430. | CF | CF | C≡C-nPr |
| 431. | CF | CF | C≡C-Bu |
| 432. | CF | CF | C≡C-iBu |
| 433. | CF | CF | C≡C-tBu |
| 434. | CF | CF | C≡C-Et |
| 435. | CF | CF | C≡C-Me |

TABLE 2*-continued

| | | | |
|---|---|---|---|
| 436. | CF | CF | C≡C-Ph |
| 437. | CF | CF | C≡C-2-Pyridyl |
| 438. | CF | CF | C≡C-3-Pyridyl |
| 439. | CF | CF | C≡C-4-Pyridyl |
| 440. | CF | CF | C≡C-2-furanyl |
| 441. | CF | CF | C≡C-3-furanyl |
| 442. | CF | CF | C≡C-2-thienyl |
| 443. | CF | CF | C≡C-3-thienyl |
| 444. | CF | CF | CH=CH-cycPr |
| 445. | CF | CF | CH=CH-iPr |
| 446. | CF | CF | CH=CH-nPr |
| 447. | CF | CF | CH=CH-Bu |
| 448. | CF | CF | CH=CH-iBu |
| 449. | CF | CF | CH=CH-tBu |
| 450. | CF | CF | CH=CH-Et |
| 451. | CF | CF | CH=CH-Me |
| 452. | CF | CF | CH=CH-Ph |
| 453. | CF | CF | CH=CH-2-Pyridyl |
| 454. | CF | CF | CH=CH-3-Pyridyl |
| 455. | CF | CF | CH=CH-4-Pyridyl |
| 456. | CF | CF | CH=CH-2-furanyl |
| 457. | CF | CF | CH=CH-3-furanyl |
| 458. | CF | CF | CH=CH-2-thienyl |
| 459. | CF | CF | CH=CH-3-thienyl |
| 460. | CF | CF | $CH_2CH_2CH_2CH_2CH_3$ |
| 461. | CF | CF | $CH_2CH_2CH(CH_3)_2$ |
| 462. | CF | CF | $CH_2CH_2CH_2CH_3$ |
| 463. | CF | CF | $CH_2CH_2CH_3$ |
| 464. | CF | CF | $CH_2CH_2$-cycPr |
| 465. | CF | CF | $CH_2CH_2$-(1-$CH_3$-cycPr) |
| 466. | CF | CF | $CH_2CH_2$-tBu |
| 467. | CF | CF | $CH_2CH_2$-cycBu |
| 468. | CF | CF | $CH_2CH_2$-(1-$CH_3$-cycBu) |
| 469. | CF | CF | $CH_2CH_2$-2-Pyridyl |
| 470. | CF | CF | $CH_2CH_2$-3-Pyridyl |
| 471. | CF | CF | $CH_2CH_2$-4-Pyridyl |
| 472. | CF | CF | $CH_2CH_2$-2-furanyl |
| 473. | CF | CF | $CH_2CH_2$-3-furanyl |
| 474. | CF | CF | $CH_2CH_2$-2-thienyl |
| 475. | CF | CF | $CH_2CH_2$-3-thienyl |
| 476. | CF | CF | $CH_2C≡C$-cycPr |
| 477. | CF | CF | $CH_2C≡C$-2-furanyl |
| 478. | CF | CF | $CH_2CH=CH$-cycPr |
| 479. | CF | CF | $CH_2CH=CH$-2-furanyl |
| 480. | CF | CF | $CH=CHCH_2$-cycPr |
| 481. | CF | CF | $CH=CHCH_2$-2-furanyl |
| 482. | CF | CF | $OCH_2C=C(CH_3)_2$ |
| 483. | CF | CF | E-$OCH_2C=CHCH_3$ |
| 484. | CF | CF | Z-$OCH_2C=CHCH_3$ |
| 485. | CF | CF | $OCH_2CH_3$ |
| 486. | CF | CF | $OCH_2CH_2CH_3$ |
| 487. | CF | CF | $OCH_2C=C(Cl)_2$ |
| 488. | CF | CF | $OCH_2C=CH_2$ |
| 489. | CF | CF | $OCH_2C≡CCH_3$ |
| 490. | CF | CF | $OCH_2CH_2CH_3$ |
| 491. | CF | CF | $OCH_2$-cycPr |
| 492. | CF | CF | $OCH_2$-(1-$CH_3$-cycPr) |
| 493. | CF | CF | $OCH_2$-cycBu |
| 494. | CF | CF | $OCH_2$-(1-$CH_3$-cycBu) |
| 495. | CF | CF | $OCH_2$-Phenyl |
| 496. | CF | CF | $OCH_2CH_2$-cycPr |
| 497. | CF | CF | $OCH_2CH=$cycPr |
| 498. | CCl | CF | C≡C-cycPr |
| 499. | CCl | CF | C≡C-(1-$CH_3$-cycPr) |
| 500. | CCl | CF | C≡C-iPr |
| 501. | CCl | CF | C≡C-nPr |
| 502. | CCl | CF | C≡C-Bu |
| 503. | CCl | CF | C≡C-iBu |
| 504. | CCl | CF | C≡C-tBu |
| 505. | CCl | CF | C≡C-Et |
| 506. | CCl | CF | C≡C-Me |
| 507. | CCl | CF | C≡C-Ph |
| 508. | CCl | CF | C≡C-2-Pyridyl |
| 509. | CCl | CF | C≡C-3-Pyridyl |
| 510. | CCl | CF | C≡C-4-Pyridyl |
| 511. | CCl | CF | C≡C-2-furanyl |
| 512. | CCl | CF | C≡C-3-furanyl |
| 513. | CCl | CF | C≡C-2-thienyl |
| 514. | CCl | CF | C≡C-3-thienyl |
| 515. | CCl | CF | CH=CH-cycPr |
| 516. | CCl | CF | CH=CH-iPr |
| 517. | CCl | CF | CH=CH-nPr |
| 518. | CCl | CF | CH=CH-Bu |
| 519. | CCl | CF | CH=CH-iBu |
| 520. | CCl | CF | CH=CH-tBu |
| 521. | CCl | CF | CH=CH-Et |
| 522. | CCl | CF | CH=CH-Me |
| 523. | CCl | CF | CH=CH-Ph |
| 524. | CCl | CF | CH=CH-2-Pyridyl |
| 525. | CCl | CF | CH=CH-3-Pyridyl |
| 526. | CCl | CF | CH=CH-4-Pyridyl |
| 527. | CCl | CF | CH=CH-2-furanyl |
| 528. | CCl | CF | CH=CH-3-furanyl |
| 529. | CCl | CF | CH=CH-2-thienyl |
| 530. | CCl | CF | CH=CH-3-thienyl |
| 531. | CCl | CF | $CH_2CH_2CH_2CH_2CH_3$ |
| 532. | CCl | CF | $CH_2CH_2CH(CH_3)_2$ |
| 533. | CCl | CF | $CH_2CH_2CH_2CH_3$ |
| 534. | CCl | CF | $CH_2CH_2CH_3$ |
| 535. | CCl | CF | $CH_2CH_2$-cycPr |
| 536. | CCl | CF | $CH_2CH_2$-(1-$CH_3$-cycPr) |
| 537. | CCl | CF | $CH_2CH_2$-tBu |
| 538. | CCl | CF | $CH_2CH_2$-cycBu |
| 539. | CCl | CF | $CH_2CH_2$-(1-$CH_3$-cycBu) |
| 540. | CCl | CF | $CH_2CH_2$-2-Pyridyl |
| 541. | CCl | CF | $CH_2CH_2$-3-Pyridyl |
| 542. | CCl | CF | $CH_2CH_2$-4-Pyridyl |
| 543. | CCl | CF | $CH_2CH_2$-2-furanyl |
| 544. | CCl | CF | $CH_2CH_2$-3-furanyl |
| 545. | CCl | CF | $CH_2CH_2$-2-thienyl |
| 546. | CCl | CF | $CH_2CH_2$-3-thienyl |
| 547. | CCl | CF | $CH_2C≡C$-cycPr |
| 548. | CCl | CF | $CH_2C≡C$-2-furanyl |
| 549. | CCl | CF | $CH_2CH=CH$-cycPr |
| 550. | CCl | CF | $CH_2CH=CH$-2-furanyl |
| 551. | CCl | CF | $CH=CHCH_2$-cycPr |
| 552. | CCl | CF | $CH=CHCH_2$-2-furanyl |
| 553. | CCl | CF | $OCH_2C=C(CH_3)_2$ |
| 554. | CCl | CF | E-$OCH_2C=CHCH_3$ |
| 555. | CCl | CF | Z-$OCH_2C=CHCH_3$ |
| 556. | CCl | CF | $OCH_2CH_3$ |
| 557. | CCl | CF | $OCH_2CH_2CH_3$ |
| 558. | CCl | CF | $OCH_2C=C(Cl)_2$ |
| 559. | CCl | CF | $OCH_2C=CH_2$ |
| 560. | CCl | CF | $OCH_2C≡CCH_3$ |
| 561. | CCl | CF | $OCH_2CH_2CH_3$ |
| 562. | CCl | CF | $OCH_2$-cycPr |
| 563. | CCl | CF | $OCH_2$-(1-$CH_3$-cycPr) |
| 564. | CCl | CF | $OCH_2$-cycBu |
| 565. | CCl | CF | $OCH_2$-(1-$CH_3$-cycBu) |
| 566. | CCl | CF | $OCH_2$-Phenyl |
| 567. | CCl | CF | $OCH_2CH_2$-cycPr |
| 568. | CCl | CF | $OCH_2CH=$cycPr |
| 569. | CF | CCl | C≡C-cycPr |
| 570. | CF | CCl | C≡C-(1-$CH_3$-cycPr) |
| 571. | CF | CCl | C≡C-iPr |
| 572. | CF | CCl | C≡C-nPr |
| 573. | CF | CCl | C≡C-Bu |
| 574. | CF | CCl | C≡C-iBu |
| 575. | CF | CCl | C≡C-tBu |
| 576. | CF | CCl | C≡C-Et |
| 577. | CF | CCl | C≡C-Me |
| 578. | CF | CCl | C≡C-Ph |
| 579. | CF | CCl | C≡C-2-Pyridyl |
| 580. | CF | CCl | C≡C-3-Pyridyl |
| 581. | CF | CCl | C≡C-4-Pyridyl |
| 582. | CF | CCl | C≡C-2-furanyl |
| 583. | CF | CCl | C≡C-3-furanyl |
| 584. | CF | CCl | C≡C-2-thienyl |
| 585. | CF | CCl | C≡C-3-thienyl |
| 586. | CF | CCl | CH=CH-cycPr |
| 587. | CF | CCl | CH=CH-iPr |
| 588. | CF | CCl | CH=CH-nPr |
| 589. | CF | CCl | CH=CH-Bu |
| 590. | CF | CCl | CH=CH-iBu |
| 591. | CF | CCl | CH=CH-tBu |
| 592. | CF | CCl | CH=CH-Et |
| 593. | CF | CCl | CH=CH-Me |

TABLE 2*-continued

| | | | |
|---|---|---|---|
| 594. | CF | CCl | CH=CH-Ph |
| 595. | CF | CCl | CH=CH-2-Pyridyl |
| 596. | CF | CCl | CH=CH-3-Pyridyl |
| 597. | CF | CCl | CH=CH-4-Pyridyl |
| 598. | CF | CCl | CH=CH-2-furanyl |
| 599. | CF | CCl | CH=CH-3-furanyl |
| 600. | CF | CCl | CH=CH-2-thienyl |
| 601. | CF | CCl | CH=CH-3-thienyl |
| 602. | CF | CCl | CH$_2$CH$_2$CH$_2$CH$_2$CH$_3$ |
| 603. | CF | CCl | CH$_2$CH$_2$CH(CH$_3$)$_2$ |
| 604. | CF | CCl | CH$_2$CH$_2$CH$_2$CH$_3$ |
| 605. | CF | CCl | CH$_2$CH$_2$CH$_3$ |
| 606. | CF | CCl | CH$_2$CH$_2$-cycPr |
| 607. | CF | CCl | CH$_2$CH$_2$-(1-CH$_3$-cycPr) |
| 608. | CF | CCl | CH$_2$CH$_2$-tBu |
| 609. | CF | CCl | CH$_2$CH$_2$-cycBu |
| 610. | CF | CCl | CH$_2$CH$_2$-(1-CH$_3$-cycBu) |
| 611. | CF | CCl | CH$_2$CH$_2$-2-Pyridyl |
| 612. | CF | CCl | CH$_2$CH$_2$-3-Pyridyl |
| 613. | CF | CCl | CH$_2$CH$_2$-4-Pyridyl |
| 614. | CF | CCl | CH$_2$CH$_2$-2-furanyl |
| 615. | CF | CCl | CH$_2$CH$_2$-3-furanyl |
| 616. | CF | CCl | CH$_2$CH$_2$-2-thienyl |
| 617. | CF | CCl | CH$_2$CH$_2$-3-thienyl |
| 618. | CF | CCl | CH$_2$C≡C-cycPr |
| 619. | CF | CCl | CH$_2$C≡C-2-furanyl |
| 620. | CF | CCl | CH$_2$CH=CH-cycPr |
| 621. | CF | CCl | CH$_2$CH=CH-2-furanyl |
| 622. | CF | CCl | CH=CHCH$_2$-cycPr |
| 623. | CF | CCl | CH=CHCH$_2$-2-furanyl |
| 624. | CF | CCl | OCH$_2$C=C(CH$_3$)$_2$ |
| 625. | CF | CCl | E-OCH$_2$C=CHCH$_3$ |
| 626. | CF | CCl | Z-OCH$_2$C=CHCH$_3$ |
| 627. | CF | CCl | OCH$_2$CH$_3$ |
| 628. | CF | CCl | OCH$_2$CH$_2$CH$_3$ |
| 629. | CF | CCl | OCH$_2$C=C(Cl)$_2$ |
| 630. | CF | CCl | OCH$_2$C=CH$_2$ |
| 631. | CF | CCl | OCH$_2$C≡CCH$_3$ |
| 632. | CF | CCl | OCH$_2$CH$_2$CH$_3$ |
| 633. | CF | CCl | OCH$_2$-cycPr |
| 634. | CF | CCl | OCH$_2$-(1-CH$_3$-cycPr) |
| 635. | CF | CCl | OCH$_2$-cycBu |
| 636. | CF | CCl | OCH$_2$-(1-CH$_3$-cycBu) |
| 637. | CF | CCl | OCH$_2$-Phenyl |
| 638. | CF | CCl | OCH$_2$CH$_2$-cycPr |
| 639. | CF | CCl | OCH$_2$CH=cycPr |
| 640. | C(OMe) | CH | C≡C-cycPr |
| 641. | C(OMe) | CH | C≡C-(1-CH$_3$-cycPr) |
| 642. | C(OMe) | CH | C≡C-iPr |
| 643. | C(OMe) | CH | C≡C-nPr |
| 644. | C(OMe) | CH | C≡C-Bu |
| 645. | C(OMe) | CH | C≡C-iBu |
| 646. | C(OMe) | CH | C≡C-tBu |
| 647. | C(OMe) | CH | C≡C-Et |
| 648. | C(OMe) | CH | C≡C-Me |
| 649. | C(OMe) | CH | C≡C-Ph |
| 650. | C(OMe) | CH | C≡C-2-Pyridyl |
| 651. | C(OMe) | CH | C≡C-3-Pyridyl |
| 652. | C(OMe) | CH | C≡C-4-Pyridyl |
| 653. | C(OMe) | CH | C≡C-2-furanyl |
| 654. | C(OMe) | CH | C≡C-3-furanyl |
| 655. | C(OMe) | CH | C≡C-2-thienyl |
| 656. | C(OMe) | CH | C≡C-3-thienyl |
| 657. | C(OMe) | CH | CH=CH-cycPr |
| 658. | C(OMe) | CH | CH=CH-iPr |
| 659. | C(OMe) | CH | CH=CH-nPr |
| 660. | C(OMe) | CH | CH=CH-Bu |
| 661. | C(OMe) | CH | CH=CH-iBu |
| 662. | C(OMe) | CH | CH=CH-tBu |
| 663. | C(OMe) | CH | CH=CH-Et |
| 664. | C(OMe) | CH | CH=CH-Me |
| 665. | C(OMe) | CH | CH=CH-Ph |
| 666. | C(OMe) | CH | CH=CH-2-Pyridyl |
| 667. | C(OMe) | CH | CH=CH-3-Pyridyl |
| 668. | C(OMe) | CH | CH=CH-4-Pyridyl |
| 669. | C(OMe) | CH | CH=CH-2-furanyl |
| 670. | C(OMe) | CH | CH=CH-3-furanyl |
| 671. | C(OMe) | CH | CH=CH-2-thienyl |
| 672. | C(OMe) | CH | CH=CH-3-thienyl |
| 673. | C(OMe) | CH | CH$_2$CH$_2$CH$_2$CH$_2$CH$_3$ |
| 674. | C(OMe) | CH | CH$_2$CH$_2$CH(CH$_3$)$_2$ |
| 675. | C(OMe) | CH | CH$_2$CH$_2$CH$_2$CH$_3$ |
| 676. | C(OMe) | CH | CH$_2$CH$_2$CH$_3$ |
| 677. | C(OMe) | CH | CH$_2$CH$_2$-cycPr |
| 678. | C(OMe) | CH | CH$_2$CH$_2$-(1-CH$_3$-cycPr) |
| 679. | C(OMe) | CH | CH$_2$CH$_2$-tBu |
| 680. | C(OMe) | CH | CH$_2$CH$_2$-cycBu |
| 681. | C(OMe) | CH | CH$_2$CH$_2$-(1-CH$_3$-cycBu) |
| 682. | C(OMe) | CH | CH$_2$CH$_2$-2-Pyridyl |
| 683. | C(OMe) | CH | CH$_2$CH$_2$-3-Pyridyl |
| 684. | C(OMe) | CH | CH$_2$CH$_2$-4-Pyridyl |
| 685. | C(OMe) | CH | CH$_2$CH$_2$-2-furanyl |
| 686. | C(OMe) | CH | CH$_2$CH$_2$-3-furanyl |
| 687. | C(OMe) | CH | CH$_2$CH$_2$-2-thienyl |
| 688. | C(OMe) | CH | CH$_2$CH$_2$-3-thienyl |
| 689. | C(OMe) | CH | CH$_2$C≡C-cycPr |
| 690. | C(OMe) | CH | CH$_2$C≡C-2-furanyl |
| 691. | C(OMe) | CH | CH$_2$CH=CH-cycPr |
| 692. | C(OMe) | CH | CH$_2$CH=CH-2-furanyl |
| 693. | C(OMe) | CH | CH=CHCH$_2$-cycPr |
| 694. | C(OMe) | CH | CH=CHCH$_2$-2-furanyl |
| 695. | C(OMe) | CH | OCH$_2$C=C(CH$_3$)$_2$ |
| 696. | C(OMe) | CH | E-OCH$_2$C=CHCH$_3$ |
| 697. | C(OMe) | CH | Z-OCH$_2$C=CHCH$_3$ |
| 698. | C(OMe) | CH | OCH$_2$CH$_3$ |
| 699. | C(OMe) | CH | OCH$_2$CH$_2$CH$_3$ |
| 700. | C(OMe) | CH | OCH$_2$C=C(Cl)$_2$ |
| 701. | C(OMe) | CH | OCH$_2$C=CH$_2$ |
| 702. | C(OMe) | CH | OCH$_2$C≡CCH$_3$ |
| 703. | C(OMe) | CH | OCH$_2$CH$_2$CH$_3$ |
| 704. | C(OMe) | CH | OCH$_2$-cycPr |
| 705. | C(OMe) | CH | OCH$_2$-(1-CH$_3$-cycPr) |
| 706. | C(OMe) | CH | OCH$_2$-cycBu |
| 707. | C(OMe) | CH | OCH$_2$-(1-CH$_3$-cycBu) |
| 708. | C(OMe) | CH | OCH$_2$-Phenyl |
| 709. | C(OMe) | CH | OCH$_2$CH$_2$-cycPr |
| 710. | C(OMe) | CH | OCH$_2$CH=cycPr |
| 711. | CH | C(OMe) | C≡C-cycPr |
| 712. | CH | C(OMe) | C≡C-(1-CH$_3$-cycPr) |
| 713. | CH | C(OMe) | C≡C-iPr |
| 714. | CH | C(OMe) | C≡C-nPr |
| 715. | CH | C(OMe) | C≡C-Bu |
| 716. | CH | C(OMe) | C≡C-iBu |
| 717. | CH | C(OMe) | C≡C-tBu |
| 718. | CH | C(OMe) | C≡C-Et |
| 719. | CH | C(OMe) | C≡C-Me |
| 720. | CH | C(OMe) | C≡C-Ph |
| 721. | CH | C(OMe) | C≡C-2-Pyridyl |
| 722. | CH | C(OMe) | C≡C-3-Pyridyl |
| 723. | CH | C(OMe) | C≡C-4-Pyridyl |
| 724. | CH | C(OMe) | C≡C-2-furanyl |
| 725. | CH | C(OMe) | C≡C-3-furanyl |
| 726. | CH | C(OMe) | C≡C-2-thienyl |
| 727. | CH | C(OMe) | C≡C-3-thienyl |
| 728. | CH | C(OMe) | CH=CH-cycPr |
| 729. | CH | C(OMe) | CH=CH-iPr |
| 730. | CH | C(OMe) | CH=CH-nPr |
| 731. | CH | C(OMe) | CH=CH-Bu |
| 732. | CH | C(OMe) | CH=CH-iBu |
| 733. | CH | C(OMe) | CH=CH-tBu |
| 734. | CH | C(OMe) | CH=CH-Et |
| 735. | CH | C(OMe) | CH=CH-Me |
| 736. | CH | C(OMe) | CH=CH-Ph |
| 737. | CH | C(OMe) | CH=CH-2-Pyridyl |
| 738. | CH | C(OMe) | CH=CH-3-Pyridyl |
| 739. | CH | C(OMe) | CH=CH-4-Pyridyl |
| 740. | CH | C(OMe) | CH=CH-2-furanyl |
| 741. | CH | C(OMe) | CH=CH-3-furanyl |
| 742. | CH | C(OMe) | CH=CH-2-thienyl |
| 743. | CH | C(OMe) | CH=CH-3-thienyl |
| 744. | CH | C(OMe) | CH$_2$CH$_2$CH$_2$CH$_2$CH$_3$ |
| 745. | CH | C(OMe) | CH$_2$CH$_2$CH(CH$_3$)$_2$ |
| 746. | CH | C(OMe) | CH$_2$CH$_2$CH$_2$CH$_3$ |
| 747. | CH | C(OMe) | CH$_2$CH$_2$CH$_3$ |
| 748. | CH | C(OMe) | CH$_2$CH$_2$-cycPr |
| 749. | CH | C(OMe) | CH$_2$CH$_2$-(1-CH$_3$-cycPr) |
| 750. | CH | C(OMe) | CH$_2$CH$_2$-tBu |
| 751. | CH | C(OMe) | CH$_2$CH$_2$-cycBu |

TABLE 2*-continued

| | | |
|---|---|---|
| 752. | CH | C(OMe) | CH$_2$CH$_2$-(1-CH$_3$-cycBu) |
| 753. | CH | C(OMe) | CH$_2$CH$_2$-2-Pyridyl |
| 754. | CH | C(OMe) | CH$_2$CH$_2$-3-Pyridyl |
| 755. | CH | C(OMe) | CH$_2$CH$_2$-4-Pyridyl |
| 756. | CH | C(OMe) | CH$_2$CH$_2$-2-furanyl |
| 757. | CH | C(OMe) | CH$_2$CH$_2$-3-furanyl |
| 758. | CH | C(OMe) | CH$_2$CH$_2$-2-thienyl |
| 759. | CH | C(OMe) | CH$_2$CH$_2$-3-thienyl |
| 760. | CH | C(OMe) | CH$_2$C≡C-cycPr |
| 761. | CH | C(OMe) | CH$_2$C≡C-2-furanyl |
| 762. | CH | C(OMe) | CH$_2$CH═CH-cycPr |
| 763. | CH | C(OMe) | CH$_2$CH═CH-2-furanyl |
| 764. | CH | C(OMe) | CH═CHCH$_2$-cycPr |
| 765. | CH | C(OMe) | CH═CHCH$_2$-2-furanyl |
| 766. | CH | C(OMe) | OCH$_2$C═C(CH$_3$)$_2$ |
| 767. | CH | C(OMe) | E-OCH$_2$C═CHCH$_3$ |
| 768. | CH | C(OMe) | Z-OCH$_2$C═CHCH$_3$ |
| 769. | CH | C(OMe) | OCH$_2$CH$_3$ |
| 770. | CH | C(OMe) | OCH$_2$CH$_2$CH$_3$ |
| 771. | CH | C(OMe) | OCH$_2$C═C(Cl)$_2$ |
| 772. | CH | C(OMe) | OCH$_2$C═CH$_2$ |
| 773. | CH | C(OMe) | OCH$_2$C≡CCH$_3$ |
| 774. | CH | C(OMe) | OCH$_2$CH$_2$CH$_3$ |
| 775. | CH | C(OMe) | OCH$_2$-cycPr |
| 776. | CH | C(OMe) | OCH$_2$-(1-CH$_3$-cycPr) |
| 777. | CH | C(OMe) | OCH$_2$-cycBu |
| 778. | CH | C(OMe) | OCH$_2$-(1-CH$_3$-cycBu) |
| 779. | CH | C(OMe) | OCH$_2$-Phenyl |
| 780. | CH | C(OMe) | OCH$_2$CH$_2$-cycPr |
| 781. | CH | C(OMe) | OCH$_2$CH═cycPr |
| 782. | —COCH2OC— | | C≡C-cycPr |
| 783. | —COCH2OC— | | C≡C-(1-CH$_3$-cycPr) |
| 784. | —COCH2OC— | | C≡C-iPr |
| 785. | —COCH2OC— | | C≡C-nPr |
| 786. | —COCH2OC— | | C≡C-Bu |
| 787. | —COCH2OC— | | C≡C-iBu |
| 788. | —COCH2OC— | | C≡C-tBu |
| 789. | —COCH2OC— | | C≡C-Et |
| 790. | —COCH2OC— | | C≡C-Me |
| 791. | —COCH2OC— | | C≡C-Ph |
| 792. | —COCH2OC— | | C≡C-2-Pyridyl |
| 793. | —COCH2OC— | | C≡C-3-Pyridyl |
| 794. | —COCH2OC— | | C≡C-4-Pyridyl |
| 795. | —COCH2OC— | | C≡C-2-furanyl |
| 796. | —COCH2OC— | | C≡C-3-furanyl |
| 797. | —COCH2OC— | | C≡C-2-thienyl |
| 798. | —COCH2OC— | | C≡C-3-thienyl |
| 799. | —COCH2OC— | | CH═CH-cycPr |
| 800. | —COCH2OC— | | CH═CH-iPr |
| 801. | —COCH2OC— | | CH═CH-nPr |
| 802. | —COCH2OC— | | CH═CH-Bu |
| 803. | —COCH2OC— | | CH═CH-iBu |
| 804. | —COCH2OC— | | CH═CH-tBu |
| 805. | —COCH2OC— | | CH═CH-Et |
| 806. | —COCH2OC— | | CH═CH-Me |
| 807. | —COCH2OC— | | CH═CH-Ph |
| 808. | —COCH2OC— | | CH═CH-2-Pyridyl |
| 809. | —COCH2OC— | | CH═CH-3-Pyridyl |
| 810. | —COCH2OC— | | CH═CH-4-Pyridyl |
| 811. | —COCH2OC— | | CH═CH-2-furanyl |
| 812. | —COCH2OC— | | CH═CH-3-furanyl |
| 813. | —COCH2OC— | | CH═CH-2-thienyl |
| 814. | —COCH2OC— | | CH═CH-3-thienyl |
| 815. | —COCH2OC— | | CH$_2$CH$_2$CH$_2$CH$_2$CH$_3$ |
| 816. | —COCH2OC— | | CH$_2$CH$_2$CH(CH$_3$)$_2$ |
| 817. | —COCH2OC— | | CH$_2$CH$_2$CH$_2$CH$_3$ |
| 818. | —COCH2OC— | | CH$_2$CH$_2$CH$_3$ |
| 819. | —COCH2OC— | | CH$_2$CH$_2$-cycPr |
| 820. | —COCH2OC— | | CH$_2$CH$_2$-(1-CH$_3$-cycPr) |
| 821. | —COCH2OC— | | CH$_2$CH$_2$-tBu |
| 822. | —COCH2OC— | | CH$_2$CH$_2$-cycBu |
| 823. | —COCH2OC— | | CH$_2$CH$_2$-(1-CH$_3$-cycBu) |
| 824. | —COCH2OC— | | CH$_2$CH$_2$-2-Pyridyl |
| 825. | —COCH2OC— | | CH$_2$CH$_2$-3-Pyridyl |
| 826. | —COCH2OC— | | CH$_2$CH$_2$-4-Pyridyl |
| 827. | —COCH2OC— | | CH$_2$CH$_2$-2-furanyl |
| 828. | —COCH2OC— | | CH$_2$CH$_2$-3-furanyl |
| 829. | —COCH2OC— | | CH$_2$CH$_2$-2-thienyl |
| 830. | —COCH2OC— | | CH$_2$CH$_2$-3-thienyl |
| 831. | —COCH2OC— | | CH$_2$C≡C-cycPr |
| 832. | —COCH2OC— | | CH$_2$C≡C-2-furanyl |
| 833. | —COCH2OC— | | CH$_2$CH═CH-cycPr |
| 834. | —COCH2OC— | | CH$_2$CH═CH-2-furanyl |
| 835. | —COCH2OC— | | CH═CHCH$_2$-cycPr |
| 836. | —COCH2OC— | | CH═CHCH$_2$-2-furanyl |
| 837. | —COCH2OC— | | OCH$_2$C═C(CH$_3$)$_2$ |
| 838. | —COCH2OC— | | E-OCH$_2$C═CHCH$_3$ |
| 839. | —COCH2OC— | | Z-OCH$_2$C═CHCH$_3$ |
| 840. | —COCH2OC— | | OCH$_2$CH$_3$ |
| 841. | —COCH2OC— | | OCH$_2$CH$_2$CH$_3$ |
| 842. | —COCH2OC— | | OCH$_2$C═C(Cl)$_2$ |
| 843. | —COCH2OC— | | OCH$_2$C═CH$_2$ |
| 844. | —COCH2OC— | | OCH$_2$C≡CCH$_3$ |
| 845. | —COCH2OC— | | OCH$_2$CH$_2$CH$_3$ |
| 846. | —COCH2OC— | | OCH$_2$-cycPr |
| 847. | —COCH2OC— | | OCH$_2$-(1-CH$_3$-cycPr) |
| 848. | —COCH2OC— | | OCH$_2$-cycBu |
| 849. | —COCH2OC— | | OCH$_2$-(1-CH$_3$-cycBu) |
| 850. | —COCH2OC— | | OCH$_2$-Phenyl |
| 851. | —COCH2OC— | | OCH$_2$CH$_2$-cycPr |
| 852. | —COCH2OC— | | OCH$_2$CH═cycPr |

*Unless otherwise noted, stereochemistry is (+/−) and in R$^2$, all double bonds are cis and trans.

Utility

The compounds of this invention possess reverse transcriptase inhibitory activity, in particular, HIV inhibitory efficacy. The compounds of formula (I) possess HIV reverse transcriptase inhibitory activity and are therefore useful as antiviral agents for the treatment of HIV infection and associated diseases. The compounds of formula (I) possess HIV reverse transcriptase inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral clone replication and/or HIV reverse transcriptase, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV reverse transcriptase, the compounds of the present invention may also be useful as diagnostic reagents in diagnostic assays for the detection of HIV reverse transcriptase. Thus, inhibition of the reverse transcriptase activity in an assay (such as the assays described herein) by a compound of the present invention would be indicative of the presence of HIV reverse transcriptase and HIV virus.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

HIV RNA Assay

DNA Plasmids and In Vitro RNA Transcripts

Plasmid pDAB 72 containing both gag and pol sequences of BH10 (bp 113–1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from the $A_{260}$.

Probes

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCTTGCCCATACTA 3') was complementary to nucleotides 889–912 of HXB2 and the pol biotinylated capture probe (5'-biotin-CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5' CCCAGTATTTGTCTACAGCCT-TCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 µM stocks in 2×SSC (0.3 M NaCl, 0.03 M sodium citrate), 0.05 M Tris pH 8.8, 1 mg/mL BSA. The biotinylated capture probes were prepared as 100 µM stocks in water.

Streptavidin Coated Plates

Streptavidin coated plates were obtained from Du Pont Biotechnology Systems (Boston, Mass.).

Cells and Virus Stocks

MT-2 and MT-4 cells were maintained in RPMI 1640 supplemented with 5% fetal calf serum (FCS) for MT-2 cells or 10% FCS for MT-4 cells, 2 mM L-glutamine and 50 µg/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1(RF) stocks were $1-3\times10^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at $5\times10^5$ cells/mL in RPMI 1640, 5% FCS for bulk infections or at $2\times10^6$/mL in Dulbecco's modified Eagles medium with 5% FCS for infection in microtiter plates. Virus was added and culture continued for 3 days at 37° C.

HIV RNA Assay

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 µL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20.) A second hybridization of reporter probe to the immobilized complex of capture probe and hybridized target RNA was carried out in the washed streptavidin coated well by addition of 120 µl of a hybridization cocktail containing 4×SSC, 0.66% Triton× 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 µL of 0.2 mM 4-methylumbelliferyl phosphate (MUBP, JBL Scientific) in buffer δ (2.5 M diethanolamine pH 8.9 (JBL Scientific), 10 mM $MgCl_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 µL) were added to a final concentration of $5\times10^5$ per mL ($1\times10^5$ per well). Cells were incubated with compounds for 30 minutes at 37° C. in a $CO_2$ incubator. For evaluation of antiviral potency, an appropriate dilution of HIV-1 (RF) virus stock (50 µL) was added to culture wells containing cells and dilutions of the test compounds. The final volume in each well was 200 µL. Eight wells per plate were left uninfected with 50 µL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 µL of medium/well was removed from the HIV infected plates. Thirty seven µL of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 µL of this diluted mixture was transferred to a streptavidin coated microtiter plate. HIV RNA was quantitated as described above. A standard curve, prepared by adding known amounts of pDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 μg/mL. $IC_{90}$ values of other antiviral compounds, both more and less potent than ddC, were reproducible using several stocks of HIV-1 (RF) when this procedure was followed. This concentration of virus corresponded to ~3×10⁵ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 μg/mL. Finally, the plateau level of viral RNA produced by an effective reverse transcriptase inhibitor should be less than 10% of the level achieved in an uninhibited infection.

For antiviral potency tests, all manipulations in microtiter plates, following the initial addition of 2×concentrated compound solution to a single row of wells, were performed using a Perkin Elmer/Cetus ProPette.

Compounds tested in the above assay are considered to be active if they exhibit an $IC_{90}$ of $\leq 20$ μM. Preferred compounds of the present invention have $IC_{90}$'s of $\leq 5$ μM. More preferred compounds of the present invention have $IC_{90}$'s of $\leq 0.5$ μM. Even more preferred compounds of the present invention have $IC_{90}$'s of $\leq 0.05$ μM. Still more preferred compounds of the present invention have $IC_{90}$'s of $\leq 0.005$ μM.

Using the methodology described above, a number of compounds of the present invention were found to exhibit an $IC_{90}$ of $\leq 20$ μM, thereby confirming the utility of the compounds of the present invention as effective HIV inhibitors.

Protein Binding and Mutant Resistance

In order to characterize NNRTI analogs for their clinical efficacy potential the effect of plasma proteins on antiviral potency and measurements of antiviral potency against wild type and mutant variants of HIV which carry amino acid changes in the known binding site for NNRTIs were examined. The rationale for this testing strategy is two fold:

1. Many drugs are extensively bound to plasma proteins. Although the binding affinity for most drugs for the major components of human plasma, namely, human serum albumin (HSA) or alpha-1-acid glycoprotein (AAG), is low, these major components are present in high concentration in the blood. Only free or unbound drug is available to cross the infected cell membrane for interaction with the target site (i.e., HIV-1 reverse transcriptase, HIV-1 RT). Therefore, the effect of added HSA+AAG on the antiviral potency in tissue culture more closely reflects the potency of a given compound in the clinical setting. The concentration of compound required for 90% inhibition of virus replication as measured in a sensitive viral RNA-based detection method is designated the IC90. The fold increase in apparent IC90 for test compounds in the presence or added levels of HSA and AAG that reflect in vivo concentrations (45 mg/ml HSA, 1 mg/ml AAG) was then calculated. The lower the fold increase, the more compound will be available to interact with the target site.

2. The combination of the high rate of virus replication in the infected individual and the poor fidelity of the viral RT results in the production of a quasi-species or mixtures of HIV species in the infected individual. These species will include a majority wild type species, but also mutant variants of HIV and the proportion of a given mutant will reflect its relative fitness and replication rate. Because mutant variants including mutants with changes in the amino acid sequence of the viral RT likely pre-exist in the infected individual's quasi-species, the overall potency observed in the clinical setting will reflect the ability of a drug to inhibit not only wild type HIV-1, but mutant variants as well. We thus have constructed, in a known genetic background, mutant variants of HIV-1 which carry amino acid substitutions at positions thought to be involved in NNRTI binding, and measured the ability of test compounds to inhibit replication of these mutant viruses. The concentration of compound required for 90% inhibition of virus replication as measured in a sensitive viral RNA-based detection method is designated the IC90. It is desirable to have a compound which has high activity against a variety of mutants.

Dosage and Formulation

The antiviral compounds of this invention can be administered as treatment for viral infections by any means that produces contact of the active agent with the agent's site of action, i.e., the viral reverse transcriptase, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences,* supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of Components (a) and (b)

Each therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the revserse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

What is claimed:
1. A compound of formula I:

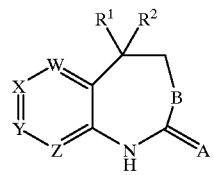

or a stereoisomer or pharmaceutically acceptable salt form thereof, wherein:
A is O or S;
B is $NR^8$;
W is $CR^3$;
X is $CR^{3a}$;
Y is $CR^{3b}$;
Z is $CR^{3c}$;
$R^1$ is selected from the group $C_{1-3}$ alkyl substituted with 0–7 halogen and cyclopropyl;
$R^2$ is selected from the group —$R^{2c}$, —$OR^{2c}$, —$OCHR^{2a}R^{2b}$, —$OCH_2CHR^{2a}R^{2b}$, —$O(CH_2)_2CHR^{2a}R^{2b}$, —$OCHR^{2a}C=C—R^{2b}$, —$OCHR^{2a}C=R^{2c}$, 13 $OCHR^{2a}C\equiv C—R^{2b}$, —$SR^{2c}$, —$SCHR^{2a}R^{2b}$, —$SCH_2CHR^{2a}R^{2b}$, —$S(CH_2)_2CHR^{2a}R^{2b}$, —$SCHR^{2a}C=C—R^{2b}$, —$SCHR^{2a}C=R^{2c}$, —$SCHR^{2a}C\equiv C—R^{2b}$, —$NR^{2a}R^{2c}$, —$NHCHR^{2a}R^{2b}$, —$NHCH_2CHR^{2a}R^{2b}$, —$NH(CH_2)_2CHR^{2a}R^{2b}$, —$NHCHR^{2a}C=C—R^{2b}$, —$NHCHR^{2a}C=R^{2c}$, and —$NHCHR^{2a}C\equiv C—R^{2b}$;
$R^{2a}$ is selected from the group H, $CH_3$, $CH_2CH_3$, $CH(CH_3)_2$, and $CH_2CH_2CH_3$;
$R^{2b}$ is H or $R^{2c}$;
$R^{2c}$ is selected from the group $C_{1-6}$ alkyl substituted with 0–2 $R^4$, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, phenyl substituted with 0–2 $R^{3d}$, and 3–6 membered heterocyclic group containing 1–3 heteroatoms selected from the group O, N, and S, substituted with 0–2 $R^{3d}$;
alternatively, the group —$NR^{2a}R^{2c}$ represents a 4–7 membered cyclic amine, wherein 0–1 carbon atoms are replaced by O or $NR^5$;
$R^3$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring containing 1–4 heteroatoms selected from the group O, N, and S;
$R^{3a}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring containing 1–4 heteroatoms selected from the group O, N, and S;
alternatively, $R^3$ and $R^{3a}$ together form —$OCH_2O$—;
$R^{3b}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;
alternatively, $R^{3a}$ and $R^{3b}$ together form —$OCH_2O$—;
$R^{3c}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3b}$ and R$^{3c}$ together form —OCH$_2$O—;

R$^{3d}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3e}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3f}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3g}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, C$_{3-10}$ carbocycle substituted with 0–3 R$^{3f}$ and a 5–10 membered heterocyclic group containing 1–3 heteroatoms selected from the group O, N, and S, substituted with 0–3 R$^{3f}$; and, R$^4$ is selected from the group F, Cl, Br, I, C$_{1-6}$ alkyl substituted with 0–2 R$^{3e}$, C$_{3-10}$ carbocycle substituted with 0–2 R$^{3e}$, phenyl substituted with 0–5 R$^{3e}$, and a 5–10 membered heterocyclic group containing 1–3 heteroatoms selected from the group O, N, and S, substituted with 0–2 R$^{3e}$;

R$^5$ and R$^{5a}$ are independently selected from the group H and C$_{1-4}$ alkyl;

alternatively, R$^5$ and R$^{5a}$, together with the nitrogen to which they are attached, combine to form a 5–6 membered ring containing 0–1 O or N atoms;

R$^6$ is selected from the group H, OH, C$_{1-4}$ alkyl, C$_{1-4}$ alkoxy, and NR$^5$R$^{5a}$;

R$^7$ is selected from the group C$_{1-3}$ alkyl and C$_{1-3}$ alkoxy;

R$^8$ is selected from the group H, OR$^9$, SR$^9$, NR$^5$R$^9$, C$_{1-6}$ alkyl substituted with 0–3 R$^{3g}$, C$_{2-6}$ alkenyl substituted with 0–3 R$^{3g}$, C$_{2-6}$ alkynyl substituted with 0–3 R$^{3g}$, C$_{3-5}$ cycloalkyl substituted with 0–2 R$^{3f}$, phenyl substituted with 0–5 R$^{3f}$, and a 5–6 membered heterocyclic group containing 1–3 heteroatoms selected from the group O, N, and S, substituted with 0–2 R$^{3f}$;

R$^9$ is selected from the group C$_{3-10}$ carbocycle substituted with 0–5 R$^{3f}$ and a 5–10 membered heterocyclic group containing 1–3 heteroatoms selected from the group O, N, and S, substituted with 0–2 R$^{3f}$; and, R$^{10}$ is selected from the group C$_{1-4}$ alkyl and phenyl.

2. A compound according to claim 1, wherein:

B is NR$^8$;

R$^1$ is selected from the group C$_{1-3}$ alkyl substituted with 1–7 halogen and cyclopropyl;

R$^2$ is selected from the group —R$^{2c}$, —OR$^{2c}$, —OCHR$^{2a}$R$^{2b}$, —OCH$_2$CHR$^{2a}$R$^{2b}$, —O(CH$_2$)$_2$CHR$^{2a}$R$^{2b}$, —OCHR$^{2a}$C=C—R$^{2b}$, —OCHR$^{2a}$C=R$^{2c}$, OCHR$^{2a}$C≡C—R$_{2b}$, —SR$^{2c}$, —SCHR$^{2a}$R$^{2b}$, —SCH$_2$CHR$^{2a}$R$^{2b}$, —S(CH$_2$)$_2$CHR$^{2a}$R$^{2b}$, —SCHR$^{2a}$C=C—R$^{2b}$, —SCHR$^{2a}$C=R$^{2c}$, and —SCHR$^{2a}$C≡C—R$^{2b}$;

R$^{2a}$ is selected from the group H, CH$_3$, CH$_2$CH$_3$, CH(CH$_3$)$_2$, and CH$_2$CH$_2$CH$_3$;

R$^{2b}$ is H or R$^{2c}$;

R$^{2c}$ is selected from the group C$_{1-5}$ alkyl substituted with 0–2 R$^4$, C$_{2-5}$ alkenyl substituted with 0–2 R$^4$, C$_{2-5}$ alkynyl substituted with 0–1 R$^4$, C$_{3-6}$ cycloalkyl substituted with 0–2 R$^{3d}$, and phenyl substituted with 0–2 R$^{3d}$;

R$^3$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

R$^{3a}$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, and NHC(O)NR$^5$R$^{5a}$;

alternatively, R$^{3a}$ and R$^{3b}$ together form —OCH$_2$O—;

R$^4$ is selected from the group Cl, F, C$_{1-4}$ alkyl substituted with 0–2 R$^{3e}$, C$_{3-5}$ carbocycle substituted with 0–2 R$^{3e}$, phenyl substituted with 0–5 R$^{3e}$, and a 5–6 membered heterocyclic group containing 1–3 heteroatoms selected from the group O, N, and S, substituted with 0–2 R$^{3e}$;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$;

R$^7$ is selected from the group CH$_3$, C$_2$H$_5$, CH(CH$_3$)$_2$, OCH$_3$, OC$_2$H$_5$, and OCH(CH$_3$)$_2$; and, R$^8$ is selected from the group H, cyclopropyl, CH$_3$, C$_2$H$_5$, and CH(CH$_3$)$_2$.

3. A compound according to claim 2, wherein:

R$^1$ is selected from the group CF$_3$, C$_2$F$_5$, and cyclopropyl;

R$^2$ is selected from the group —R$^{2c}$, —OR$^{2c}$, —OCHR$^{2a}$R$^{2b}$, —OCH$_2$CHR$^{2a}$R$^{2b}$, —OCHR$^{2a}$C=C—R$^{2b}$, —OCHR$^{2a}$C=R$^{2c}$, —OCHR$^{2a}$C≡C—R$^{2b}$, —SR$^{2c}$, —SCHR$^{2a}$R$^{2b}$, —SCH$_2$CHR$^{2a}$R$^{2b}$, —SCHR$^{2a}$C=C—R$^{2b}$, —SCHR$^{2a}$C=R$^{2c}$, and —SCHR$^{2a}$C≡C—R$^{2b}$;

R$^{2a}$ is selected from the group H, CH$_3$, CH$_2$CH$_3$, CH(CH$_3$)$_2$, and CH$_2$CH$_2$CH$_3$;

R$^{2b}$ is H or R$^{2c}$;

R$^{2c}$ is selected from the group C$_{1-3}$ alkyl substituted with 0–2 R$^4$, C$_{2-3}$ alkenyl substituted with 0–2 R$^4$, C$_{2-3}$ alkynyl substituted with 0–1 R$^4$, and C$_{3-6}$ cycloalkyl substituted with 0–2 R$^{3d}$;

R$^3$, at each occurrence, is independently selected from the group H, C$_{1-3}$ alkyl, OH, C$_{1-3}$ alkoxy, F, Cl, Br, I, NR$^5$R$^{5a}$, NO$_2$, —CN, C(O)R$^6$, NHC(O)R$^7$, and NHC(O)NR$^5$R$^{5a}$;

alternatively, R$^3$ and R$^{3a}$ together form —OCH$_2$O—;

R$^{3b}$ is H;

R$^{3c}$ is H;

R$^{3e}$, at each occurrence, is independently selected from the group H, C$_{1-4}$ alkyl, —OH, C$_{1-4}$ alkoxy, OCF$_3$, F, Cl, —NR$^5$R$^{5a}$, —C(O)R$^6$, and —SO$_2$NR$^5$R$^{5a}$;

87

R⁴ is selected from the group Cl, F, C$_{1-4}$ alkyl substituted with 0–1 R$^{3e}$, C$_{3-5}$ carbocycle substituted with 0–2 R$^{3e}$, phenyl substituted with 0–2 R$^{3e}$, and a 5–6 membered heterocyclic group containing 1–3 heteroatoms selected from the group O, N, and S, substituted with 0–1 R$^{3e}$;

R⁵ and R$^{5a}$ are independently selected from the group H, CH₃ and C₂H₅;

R⁶ is selected from the group H, OH, CH₃, C₂H₅, OCH₃, OC₂H₅, and NR⁵R$^{5a}$;

R⁷ is selected from the group CH₃, C₂H₅, OCH₃, and OC₂H₅; and,

R⁸ is selected from the group H, cyclopropyl, CH₃, and C₂H₅.

4. A compound according to claim 3, wherein:

R¹ is CF₃;

R² is selected from the group —R$^{2c}$, —OR$^{2c}$, —OCH₂R$^{2b}$, —OCH₂CH₂R$^{2b}$, —OCH₂C=C—R$^{2b}$, —OCH₂C≡C—R$^{2b}$, —SR$^{2c}$, —SCH₂R$^{2b}$, —SCH₂CH₂R$^{2b}$, —SCH₂C=C—R$^{2b}$, and —SCH₂C≡C—R$^{2b}$;

R$^{2b}$ is H or R$^{2c}$;

R$^{2c}$ is selected from the group methyl substituted with 0–2 R⁴, ethyl substituted with 0–2 R⁴, propyl substituted with 0–2 R⁴, ethenyl substituted with 0–2 R⁴, 1-propenyl substituted with 0–2 R⁴, 2-propenyl substituted with 0–2 R⁴, ethynyl substituted with 0–2 R⁴, 1-propynyl substituted with 0–2 R⁴, 2-propynyl substituted with 0–2 R⁴, and cyclopropyl substituted with 0–1 R$^{3d}$;

R³, at each occurrence, is independently selected from the group C$_{1-3}$ alkyl, OH, C$_{1-3}$ alkoxy, F, Cl, NR⁵R$^{5a}$, NO₂, —CN, and C(O)R⁶;

alternatively, R³ and R$^{3a}$ together form —OCH₂O—;

R$^{3d}$, at each occurrence, is independently selected from the group CH₃, —OH, OCH₃, OCF₃, F, Cl, and —NR⁵R$^{5a}$;

R$^{3e}$, at each occurrence, is independently selected from the group CH₃, —OH, OCH₃, OCF₃, F, Cl, and —NR⁵R$^{5a}$;

R⁴ is selected from the group Cl, F, CH₃, CH₂CH₃, cyclopropyl substituted with 0–1 R$^{3e}$, 1-methylcyclopropyl substituted with 0–1 R$^{3e}$, cyclobutyl substituted with 0–1 R$^{3e}$, phenyl substituted with 0–2 R$^{3e}$, and a 5–6 membered heterocyclic group containing 1–3 heteroatoms selected from the group O, N, and S, substituted with 0–1 R$^{3e}$, wherein the heterocyclic group is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl;

R⁵ and R$^{5a}$ are independently selected from the group H, CH₃ and C₂H₅;

R⁶ is selected from the group H, OH, CH₃, C₂H₅, OCH₃, OC₂H₅, and NR⁵R$^{5a}$;

R⁷ is selected from the group CH₃, C₂H₅, OCH₃, and OC₂H₅; and,

R⁸ is selected from the group H, cyclopropyl, and C₂H₅.

5. A compound according to claim 4, wherein the compound is of formula Ia:

88

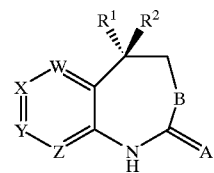

6. A compound according to claim 4, wherein the compound is of formula Ib:

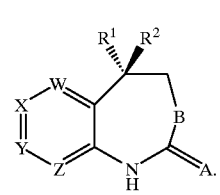

7. A compound according to claim 1, wherein the compound is selected from the group:

7-Chloro-5-(2-cyclopropylethynyl)-1,5-dihydro-5-(trifluoromethyl)-1,3-benzodiazepin-2-one;

6,7-difluoro-5-(2-cyclopropylethynyl)-1,5-dihydro-5-(trifluoromethyl)-1,3-benzodiazepin-2-one;

7-Chloro-5-(2-cyclopropylethenyl)-1,5-dihydro-5-(trifluoromethyl)-1,3-benzodiazepin-2-one;

7-Chloro-5-(2-cyclopropylethynyl)-1,5-dihydro-5-(trifluoromethyl)-1,3-benzodiazepin-2-thione;

7-Chloro-5-(2-n-butyl)-1,5-dihydro-5-(trifluoromethyl)-1,3-benzodiazepin-2-one;

7-Chloro-5-(2-cyclopropylethynyl)-1,5-dihydro-3-methyl-5-(trifluoromethyl)-1,3-benzodiazepin-2-one;

7-Chloro-5-(2-cyclopropylethynyl)-1,5-dihydro-3-ethyl-5-(trifluoromethyl)-1,3-benzodiazepin-2-one;

7-Chloro-5-(2-cyclopropylethynyl)-1,5-dihydro-3-cyclopropyl-5-(trifluoromethyl)-1,3-benzodiazepin-2-one;

7-Chloro-5-cyclopropylmethyloxy-1,5-dihydro-3-methyl-5-(trifluoromethyl)-1,3-benzodiazepin-2-one;

7-Chloro-5-(3-methyl-2-butenyloxy)-1,5-dihydro-3-methyl-5-(trifluoromethyl)-1,3-benzodiazepin-2-one;

7-Chloro-5-(3-allyloxy)-1,5-dihydro-3-methyl-5-(trifluoromethyl)-1,3-benzodiazepin-2-one;

7-Chloro-5-(3,3-dichloro-2-propenyloxy)-1,5-dihydro-3-methyl-5-(trifluoromethyl)-1,3-benzodiazepin-2-one;

7-Chloro-5-(2-propynyloxy)-1,5-dihydro-3-methyl-5-(trifluoromethyl)-1,3-benzodiazepin-2-one;

7-Chloro-5-(2-fluoro-6-methoxybenzyloxy)-1,5-dihydro-3-methyl-5-(trifluoromethyl)-1,3-benzodiazepin-2-one;

7-Chloro-5-(cyclopropylmethyloxy)-1,5-dihydro-5-(trifluoromethyl)-1,3-benzodiazepin-2-one;

(S)-7-Chloro-5-(cyclopropylmethyloxy)-1,5-dihydro-5-(trifluoromethyl)-1,3-benzodiazepin-2-one;

7-Chloro-3-cyclopropyl-5-(cyclopropylmethoxy)-1,5-dihydro-5-(trifluoromethyl)-1,3-benzodiazepin-2-one;

(S)-7-Chloro-3-cyclopropyl-5-(cyclopropylmethoxy)-1,5-dihydro-5-(trifluoromethyl)-1,3-benzodiazepin-2-one;

7-Chloro-3-cyclopropyl-5-propyloxy-1,5-dihydro-5-(trifluoromethyl)-1,3-benzodiazepin-2-one;

7-Chloro-3-cyclopropyl-5-propylthio-1,5-dihydro-5-(trifluoromethyl)-1,3-benzodiazepin-2-one;

7-Chloro-3-cyclopropyl-5-allylthio-1,5-dihydro-5-(trifluoromethyl)-1,3-benzodiazepin-2-one;

7-Chloro-3-cyclopropyl-5-allyloxy-1,5-dihydro-5-(trifluoromethyl)-1,3-benzodiazepin-2-one;

7-Chloro-3-cyclopropyl-5-(3-methyl-2-butenyloxy)-1,5-dihydro-5-(trifluoromethyl)-1,3-benzodiazepin-2-one;

7-Chloro-3-cyclopropyl-5-cyclobutylmethyloxy-1,5-dihydro-5-(trifluoromethyl)-1,3-benzodiazepin-2-one;

7-Chloro-3-cyclopropyl-5-(1-methylcyclopropyl)methyloxy-1,5-dihydro-5-(trifluoromethyl)-1,3-benzodiazepin-2-one;

7-Chloro-3-cyclopropyl-5-(2-pyridyl)methyloxy-1,5-dihydro-5-(trifluoromethyl)-1,3-benzodiazepin-2-one;

7-Chloro-3-isopropyl-5-cyclopropylmethyloxy-1,5-dihydro-5-(trifluoromethyl)-1,3-benzodiazepin-2-one;

7-Chloro-3-cyclobutyl-5-cyclopropylmethyloxy-1,5-dihydro-5-(trifluoromethyl)-1,3-benzodiazepin-2-one;

7-Chloro-5-(cyclopropylmethoxy)-1,5-dihydro-3-ethyl-5-(trifluoromethyl)-1,3-benzodiazepin-2-one;

(S)-7-Chloro-5-(cyclopropylmethyloxy)-1,5-dihydro-3-ethyl-5-(trifluoromethyl)-1,3-benzodiazepin-2-one;

7-Chloro-3-ethyl-5-(3-methyl-2-butenyloxy)-1,5-dihydro-5-(trifluoromethyl)-1,3-benzodiazepin-2-one;

7-Chloro-3-ethyl-5-allylthio-1,5-dihydro-5-(trifluoromethyl)-1,3-benzodiazepin-2-one;

7-Chloro-3-ethyl-5-cyclobutylmethyloxy-1,5-dihydro-5-(trifluoromethyl)-1,3-benzodiazepin-2-one;

7-Chloro-3-ethyl-5-cyclopropylmethylthio-1,5-dihydro-5-(trifluoromethyl)-1,3-benzodiazepin-2-one;

7-Chloro-3-ethyl-5-(1-methylcyclopropyl)methyloxy-1,5-dihydro-5-(trifluoromethyl)-1,3-benzodiazepin-2-one;

7-Chloro-3-propyl-5-cyclopropylmethyloxy-1,5-dihydro-5-(trifluoromethyl)-1,3-benzodiazepin-2-one;

7-Fluoro-5-(cyclopropylmethoxy)-1,5-dihydro-5-(trifluoromethyl)-1,3-benzodiazepin-2-one;

7-Fluoro-3-ethyl-5-cyclopropylmethyloxy-1,5-dihydro-5-(trifluoromethyl)-1,3-benzodiazepin-2-one;

7-Fluoro-5-(cyclobutylmethoxy)-1,5-dihydro-5-(trifluoromethyl)-1,3-benzodiazepin-2-one;

7-Fluoro-3-ethyl-5-cyclobutylmethyloxy-1,5-dihydro-5-(trifluoromethyl)-1,3-benzodiazepin-2-one;

7-Chloro-5-[2-(1-methylcyclopropyl)ethynyl]-1,5-dihydro-5-(trifluoromethyl)-1,3-benzodiazepin-2-one;

7-Chloro-5-cyclobutylmethyloxy-1,5-dihydro-5-(trifluoromethyl)-1,3-benzodiazepin-2-one;

7-Chloro-5-(3-methyl-2-butenyloxy)-1,5-dihydro-5-(trifluoromethyl)-1,3-benzodiazepin-2-one;

7-Chloro-5-(phenylmethyloxy)-1,5-dihydro-5-(trifluoromethyl)-1,3-benzodiazepin-2-one;

7-Chloro-5-[(2-pyridyl)methyloxy]-1,5-dihydro-5-(trifluoromethyl)-1,3-benzodiazepin-2-one;

7-Chloro-5-[(1-methylcyclopropyl)methoxy]-1,5-dihydro-5-(trifluoromethyl)-1,3-benzodiazepin-2-one;

7-Chloro-5-(3-methylphenyloxy)-1,5-dihydro-5-(trifluoromethyl)-1,3-benzodiazepin-2-one;

7-Chloro-5-(cyclopropylmethylthio)-1,5-dihydro-5-(trifluoromethyl)-1,3-benzodiazepin-2-one;

7-Chloro-5-(propylthio)-1,5-dihydro-5-(trifluoromethyl)-1,3-benzodiazepin-2-one; and, 7-Chloro-5-(2-propenylthio)-1,5-dihydro-5-(trifluoromethyl)-1,3-benzodiazepin-2-one;

or a pharmaceutically acceptable salt form thereof.

8. A compound according to claim 1, wherein the compound is selected from the group:

(S)-7-Chloro-5-(2-cyclopropylethynyl)-1,5-dihydro-5-(trifluoromethyl)-1,3-benzodiazepin-2-one;

(S)-6,7-difluoro-5-(2-cyclopropylethynyl)-1,5-dihydro-5-(trifluoromethyl)-1,3-benzodiazepin-2-one;

(S)-7-Chloro-5-(2-cyclopropylethenyl)-1,5-dihydro-5-(trifluoromethyl)-1,3-benzodiazepin-2-one;

(S)-7-Chloro-5-(2-cyclopropylethynyl)-1,5-dihydro-5-(trifluoromethyl)-1,3-benzodiazepin-2-thione;

(S)-7-Chloro-5-(2-n-butyl)-1,5-dihydro-5-(trifluoromethyl)-1,3-benzodiazepin-2-one;

(S)-7-Chloro-5-(2-cyclopropylethynyl)-1,5-dihydro-3-methyl-5-(trifluoromethyl)-1,3-benzodiazepin-2-one;

(S)-7-Chloro-5-(2-cyclopropylethynyl)-1,5-dihydro-3-ethyl-5-(trifluoromethyl)-1,3-benzodiazepin-2-one;

(S)-7-Chloro-5-(2-cyclopropylethynyl)-1,5-dihydro-3-cyclopropyl-5-(trifluoromethyl)-1,3-benzodiazepin-2-one;

(S)-7-Chloro-5-cyclopropylmethyloxy-1,5-dihydro-3-methyl-5-(trifluoromethyl)-1,3-benzodiazepin-2-one;

(S)-7-Chloro-5-(3-methyl-2-butenyloxy)-1,5-dihydro-3-methyl-5-(trifluoromethyl)-1,3-benzodiazepin-2-one;

(S)-7-Chloro-5-(3-allyloxy)-1,5-dihydro-3-methyl-5-(trifluoromethyl)-1,3-benzodiazepin-2-one;

(S)-7-Chloro-5-(3,3-dichloro-2-propenyloxy)-1,5-dihydro-3-methyl-5-(trifluoromethyl)-1,3-benzodiazepin-2-one;

(S)-7-Chloro-5-(2-propynyloxy)-1,5-dihydro-3-methyl-5-(trifluoromethyl)-1,3-benzodiazepin-2-one;

(S)-7-Chloro-5-(2-fluoro-6-methoxybenzyloxy)-1,5-dihydro-3-methyl-5-(trifluoromethyl)-1,3-benzodiazepin-2-one;

(S)-7-Chloro-5-(cyclopropylmethyloxy)-1,5-dihydro-5-(trifluoromethyl)-1,3-benzodiazepin-2-one;

(S)-7-Chloro-5-(cyclopropylmethyloxy)-1,5-dihydro-5-(trifluoromethyl)-1,3-benzodiazepin-2-one;

(S)-7-Chloro-3-cyclopropyl-5-(cyclopropylmethoxy)-1,5-dihydro-5-(trifluoromethyl)-1,3-benzodiazepin-2-one;

(S)-7-Chloro-3-cyclopropyl-5-(cyclopropylmethoxy)-1,5-dihydro-5-(trifluoromethyl)-1,3-benzodiazepin-2-one;

(S)-7-Chloro-3-cyclopropyl-5-propyloxy-1,5-dihydro-5-(trifluoromethyl)-1,3-benzodiazepin-2-one;

(S)-7-Chloro-3-cyclopropyl-5-propylthio-1,5-dihydro-5-(trifluoromethyl)-1,3-benzodiazepin-2-one;

(S)-7-Chloro-3-cyclopropyl-5-allylthio-1,5-dihydro-5-(trifluoromethyl)-1,3-benzodiazepin-2-one;

(S)-7-Chloro-3-cyclopropyl-5-allyloxy-1,5-dihydro-5-(trifluoromethyl)-1,3-benzodiazepin-2-one;

(S)-7-Chloro-3-cyclopropyl-5-(3-methyl-2-butenyloxy)-1,5-dihydro-5-(trifluoromethyl)-1,3-benzodiazepin-2-one;

(S)-7-Chloro-3-cyclopropyl-5-cyclobutylmethyloxy-1,5-dihydro-5-(trifluoromethyl)-1,3-benzodiazepin-2-one;

(S)-7-Chloro-3-cyclopropyl-5-(1-methylcyclopropyl)methyloxy-1,5-dihydro-5-(trifluoromethyl)-1,3-benzodiazepin-2-one;

(S)-7-Chloro-3-cyclopropyl-5-(2-pyridyl)methyloxy-1,5-dihydro-5-(trifluoromethyl)-1,3-benzodiazepin-2-one;

(S)-7-Chloro-3-isopropyl-5-cyclopropylmethyloxy-1,5-dihydro-5-(trifluoromethyl)-1,3-benzodiazepin-2-one;

(S)-7-Chloro-3-cyclobutyl-5-cyclopropylmethyloxy-1,5-dihydro-5-(trifluoromethyl)-1,3-benzodiazepin-2-one;

(S)-7-Chloro-5-(cyclopropylmethoxy)-1,5-dihydro-3-ethyl-5-(trifluoromethyl)-1,3-benzodiazepin-2-one;

(S)-7-Chloro-5-(cyclopropylmethyloxy)-1,5-dihydro-3-ethyl-5-(trifluoromethyl)-1,3-benzodiazepin-2-one;

(S)-7-Chloro-3-ethyl-5-(3-methyl-2-butenyloxy)-1,5-dihydro-5-(trifluoromethyl)-1,3-benzodiazepin-2-one;

(S)-7-Chloro-3-ethyl-5-allylthio-1,5-dihydro-5-(trifluoromethyl)-1,3-benzodiazepin-2-one;

(S)-7-Chloro-3-ethyl-5-cyclobutylmethyloxy-1,5-dihydro-5-(trifluoromethyl)-1,3-benzodiazepin-2-one;

(S)-7-Chloro-3-ethyl-5-cyclopropylmethylthio-1,5-dihydro-5-(trifluoromethyl)-1,3-benzodiazepin-2-one;

(S)-7-Chloro-3-ethyl-5-(1-methylcyclopropyl)methyloxy-1,5-dihydro-5-(trifluoromethyl)-1,3-benzodiazepin-2-one;

(S)-7-Chloro-3-propyl-5-cyclopropylmethyloxy-1,5-dihydro-5-(trifluoromethyl)-1,3-benzodiazepin-2-one;

(S)-7-Fluoro-5-(cyclopropylmethoxy)-1,5-dihydro-5-(trifluoronethyl)-1,3-benzodiazepin-2-one;
(S)-7-Fluoro-3-ethyl-5-cyclopropylmethyloxy-1,5-dihydro-5-(trifluoromethyl)-1,3-benzodiazepin-2-one;
(S)-7-Fluoro-5-(cyclobutylmethoxy)-1,5-dihydro-5-(trifluoromethyl)-1,3-benzodiazepin-2-one;
(S)-7-Fluoro-3-ethyl-5-cyclobutylmethyloxy-1,5-dihydro-5-(trifluoromethyl)-1,3-benzodiazepin-2-one;
(S)-7-Chloro-5-[2-(1-methylcyclopropyl)ethynyl]-1,5-dihydro-5-(trifluoromethyl)-1,3-benzodiazepin-2-one;
(S)-7-Chloro-5-cyclobutylmethyloxy-1,5-dihydro-5-(trifluoromethyl)-1,3-benzodiazepin-2-one;
(S)-7-Chloro-5-(3-methyl-2-butenyloxy)-1,5-dihydro-5-(trifluoromethyl)-1,3-benzodiazepin-2-one;
(S)-7-Chloro-5-(phenylmethyloxy)-1,5-dihydro-5-(trifluoromethyl)-1,3-benzodiazepin-2-one;
(S)-7-Chloro-5-[(2-pyridyl)methyloxy]-1,5-dihydro-5-(trifluoromethyl)-1,3-benzodiazepin-2-one;
(S)-7-Chloro-5-[(1-methylcyclopropyl)methyoxy]-1,5-dihydro-5-(trifluoromethyl)-1,3-benzodiazepin-2-one;
(S)-7-Chloro-5-(3-methylphenyloxy)-1,5-dihydro-5-(trifluoromethyl)-1,3-benzodiazepin-2-one;
(S)-7-Chloro-5-(cyclopropylmethylthio)-1,5-dihydro-5-(trifluoromethyl)-1,3-benzodiazepin-2-one;
(S)-7-Chloro-5-(propylthio)-1,5-dihydro-5-(trifluoromethyl)-1,3-benzodiazepin-2-one; and,
(S)-7-Chloro-5-(2-propenylthio)-1,5-dihydro-5-(trifluoromethyl)-1,3-benzodiazepin-2-one;
or a pharmaceutically acceptable salt form thereof.

9. A compound according to claim 1, wherein the compound is selected from the group:
(R)-7-Chloro-5-(2-cyclopropylethynyl)-1,5-dihydro-5-(trifluoromethyl)-1,3-benzodiazepin-2-one;
(R)-6,7-difluoro-5-(2-cyclopropylethynyl)-1,5-dihydro-5-(trifluoromethyl)-1,3-benzodiazepin-2-one;
(R)-7-Chloro-5-(2-cyclopropylethenyl)-1,5-dihydro-5-(trifluoromethyl)-1,3-benzodiazepin-2-one;
(R)-7-Chloro-5-(2-cyclopropylethynyl)-1,5-dihydro-5-(trifluoromethyl)-1,3-benzodiazepin-2-thione;
(R)-7-Chloro-5-(2-n-butyl)-1,5-dihydro-5-(trifluoromethyl)-1,3-benzodiazepin-2-one;
(R)-7-Chloro-5-(2-cyclopropylethynyl)-1,5-dihydro-3-methyl-5-(trifluoromethyl)-1,3-benzodiazepin-2-one;
(R)-7-Chloro-5-(2-cyclopropylethynyl)-1,5-dihydro-3-ethyl-5-(trifluoromethyl)-1,3-benzodiazepin-2-one;
(R)-7-Chloro-5-(2-cyclopropylethynyl)-1,5-dihydro-3-cyclopropyl-5-(trifluoromethyl)-1,3-benzodiazepin-2-one;
(R)-7-Chloro-5-cyclopropylmethyloxy-1,5-dihydro-3-methyl-5-(trifluoromethyl)-1,3-benzodiazepin-2-one;
(R)-7-Chloro-5-(3-methyl-2-butenyloxy)-1,5-dihydro-3-methyl-5-(trifluoromethyl)-1,3-benzodiazepin-2-one;
(R)-7-Chloro-5-(3-allyloxy)-1,5-dihydro-3-methyl-5-(trifluoromethyl)-1,3-benzodiazepin-2-one;
(R)-7-Chloro-5-(3,3-dichloro-2-propenyloxy)-1,5-dihydro-3-methyl-5-(trifluoromethyl)-1,3-benzodiazepin-2-one;
(R)-7-Chloro-5-(2-propynyloxy)-1,5-dihydro-3-methyl-5-(trifluoromethyl)-1,3-benzodiazepin-2-one;
(R)-7-Chloro-5-(2-fluoro-6-methoxybenzyloxy)-1,5-dihydro-3-methyl-5-(trifluoromethyl)-1,3-benzodiazepin-2-one;
(R)-7-Chloro-5-(cyclopropylmethyloxy)-1,5-dihydro-5-(trifluoromethyl)-1,3-benzodiazepin-2-one;
(R)-7-Chloro-5-(cyclopropylmethyloxy)-1,5-dihydro-5-(trifluoromethyl)-1,3-benzodiazepin-2-one;
(R)-7-Chloro-3-cyclopropyl-5-(cyclopropylmethoxy)-1,5-dihydro-5-(trifluoromethyl)-1,3-benzodiazepin-2-one;
(R)-7-Chloro-3-cyclopropyl-5-(cyclopropylmethoxy)-1,5-dihydro-5-(trifluoromethyl)-1,3-benzodiazepin-2-one;
(R)-7-Chloro-3-cyclopropyl-5-propyloxy-1,5-dihydro-5-(trifluoromethyl)-1,3-benzodiazepin-2-one;
(R)-7-Chloro-3-cyclopropyl-5-propylthio-1,5-dihydro-5-(trifluoromethyl)-1,3-benzodiazepin-2-one;
(R)-7-Chloro-3-cyclopropyl-5-allylthio-1,5-dihydro-5-(trifluoromethyl)-1,3-benzodiazepin-2-one;
(R)-7-Chloro-3-cyclopropyl-5-allyloxy-1,5-dihydro-5-(trifluoromethyl)-1,3-benzodiazepin-2-one;
(R)-7-Chloro-3-cyclopropyl-5-(3-methyl-2-butenyloxy)-1,5-dihydro-5-(trifluoromethyl)-1,3-benzodiazepin-2-one;
(R)-7-Chloro-3-cyclopropyl-5-cyclobutylmethyloxy-1,5-dihydro-5-(trifluoromethyl)-1,3-benzodiazepin-2-one;
(R)-7-Chloro-3-cyclopropyl-5-(1-methylcyclopropyl)methyloxy-1,5-dihydro-5-(trifluoromethyl)-1,3-benzodiazepin-2-one;
(R)-7-Chloro-3-cyclopropyl-5-(2-pyridyl)methyloxy-1,5-dihydro-5-(trifluoromethyl)-1,3-benzodiazepin-2-one;
(R)-7-Chloro-3-isopropyl-5-cyclopropylmethyloxy-1,5-dihydro-5-(trifluoromethyl)-1,3-benzodiazepin-2-one;
(R)-7-Chloro-3-cyclobutyl-5-cyclopropylmethyloxy-1,5-dihydro-5-(trifluoromethyl)-1,3-benzodiazepin-2-one;
(R)-7-Chloro-5-(cyclopropylmethoxy)-1,5-dihydro-3-ethyl-5-(trifluoromethyl)-1,3-benzodiazepin-2-one;
(R)-7-Chloro-5-(cyclopropylmethyloxy)-1,5-dihydro-3-ethyl-5-(trifluoromethyl)-1,3-benzodiazepin-2-one;
(R)-7-Chloro-3-ethyl-5-(3-methyl-2-butenyloxy)-1,5-dihydro-5-(trifluoromethyl)-1,3-benzodiazepin-2-one;
(R)-7-Chloro-3-ethyl-5-allylthio-1,5-dihydro-5-(trifluoromethyl)-1,3-benzodiazepin-2-one;
(R)-7-Chloro-3-ethyl-5-cyclobutylmethyloxy-1,5-dihydro-5-(trifluoromethyl)-1,3-benzodiazepin-2-one;
(R)-7-Chloro-3-ethyl-5-cyclopropylmethylthio-1,5-dihydro-5-(trifluoromethyl)-1,3-benzodiazepin-2-one;
(R)-7-Chloro-3-ethyl-5-(1-methylcyclopropyl)methyloxy-1,5-dihydro-5-(trifluoromethyl)-1,3-benzodiazepin-2-one;
(R)-7-Chloro-3-propyl-5-cyclopropylmethyloxy-1,5-dihydro-5-(trifluoromethyl)-1,3-benzodiazepin-2-one;
(R)-7-Fluoro-5-(cyclopropymethoxy)-1,5-dihydro-5-(trifluoromethyl)-1,3-benzodiazepin-2-one;
(R)-7-Fluoro-3-ethyl-5-cyclopropylmethyloxy-1,5-dihydro-5-(trifluoromethyl)-1,3-benzodiazepin-2-one;
(R)-7-Fluoro-5-(cyclobutylmethoxy)-1,5-dihydro-5-(trifluoromethyl)-1,3-benzodiazepin-2-one;
(R)-7-Fluoro-3-ethyl-5-cyclobutylmethyloxy-1,5-dihydro-5-(trifluoromethyl)-1,3-benzodiazepin-2-one;
(R)-7-Chloro-5-[2-(1-methylcyclopropyl)ethynyl]-1,5-dihydro-5-(trifluoromethyl)-1,3-benzodiazepin-2-one;
(R)-7-Chloro-5-cyclobutylmethyloxy-1,5-dihydro-5-(trifluoromethyl)-1,3-benzodiazepin-2-one;
(R)-7-Chloro-5-(3-methyl-2-butenyloxy)-1,5-dihydro-5-(trifluoromethyl)-1,3-benzodiazepin-2-one;
(R)-7-Chloro-5-(phenylmethyloxy)-1,5-dihydro-5-(trifluoromethyl)-1,3-benzodiazepin-2-one;
(R)-7-Chloro-5-[(2-pyridyl)methyloxy]-1,5-dihydro-5-(trifluoromethyl)-1,3-benzodiazepin-2-one;

(R)-7-Chloro-5-[(1-methylcyclopropyl)methyoxy]-1,5-dihydro-5-(trifluoromethyl)-1,3-benzodiazepin-2-one;
(R)-7-Chloro-5-(3-methylphenyloxy)-1,5-dihydro-5-(trifluoromethyl)-1,3-benzodiazepin-2-one;
(R)-7-Chloro-5-(cyclopropylmethylthio)-1,5-dihydro-5-(trifluoromethyl)-1,3-benzodiazepin-2-one;
(R)-7-Chloro-5-(propylthio)-1,5-dihydro-5-(trifluoromethyl)-1,3-benzodiazepin-2-one; and,
(R)-7-Chloro-5-(2-propenylthio)-1,5-dihydro-5-(trifluoromethyl)-1,3-benzodiazepin-2-one;
or a pharmaceutically acceptable salt form thereof.

10. A pharmaceutical composition comprising a pharmaceutically acceptable carrier and a therapeutically effective amount of a compound according to claim 1 or pharmaceutically acceptable salt form thereof.

11. A method of treating HIV infection which comprises administering to a host in need of such treatment a therapeutically effective amount of a compound according to claim 1 or pharmaceutically acceptable salt form thereof.

* * * * *